United States Patent [19]
Anderson et al.

[11] Patent Number: 5,843,439
[45] Date of Patent: Dec. 1, 1998

[54] THERAPEUTIC APPLICATION OF CHIMERIC AND RADIOLABELED ANTIBODIES TO HUMAN B LYMPHOCYTE RESTRICTED DIFFERENTIATION ANTIGEN FOR TREATMENT OF B CELL LYMPHOMA

[76] Inventors: Darrell R. Anderson, 1851 Navajo Pl., Escondido, Calif. 92029; Nabil Hanna, 3255 Fortuna Ranch Rd., Olivenhain; John E. Leonard, 1960 Avenida Joaquin, Encinitas, both of Calif. 92024; Roland A. Newman, 4311 Robbins St.; Mitchell E. Reff, 4166 Combe Way, both of San Diego, Calif. 92122; William H. Rastetter, 16067 Puerta Del Sol, Rancho Sante Fe, Calif. 92067

[21] Appl. No.: 478,967

[22] Filed: Jun. 7, 1995

Related U.S. Application Data

[60] Division of Ser. No. 149,099, Nov. 3, 1993, and a continuation-in-part of Ser. No. 978,891, Nov. 13, 1992, abandoned.

[51] Int. Cl.⁶ .......................... A61K 39/00; A61K 39/395; A61K 51/00; C07K 16/30
[52] U.S. Cl. ...................... 424/133.1; 424/143.1; 424/144.1; 424/153.1; 424/155.1; 424/173.1; 424/174.1; 424/1.49; 424/800; 424/801; 424/93.7; 530/387.3; 530/388.22; 530/388.73; 530/388.8; 530/389.7; 530/391.3; 530/804; 530/867; 435/328; 435/334; 435/343.1; 435/344; 435/354

[58] Field of Search ................. 424/133.1, 143.1, 424/144.1, 153.1, 155.1, 173.1, 174.1, 1.49, 800, 801, 93.7; 435/69.6, 70.21, 172.2, 240.27, 328, 334, 343.1, 344, 354; 530/387.3, 388.22, 388.73, 388.8, 389.7, 391.3, 809, 867; 935/89, 104, 107

[56] References Cited

U.S. PATENT DOCUMENTS 5,500,362  3/1996  Robinson et al. ................ 435/7.23

FOREIGN PATENT DOCUMENTS

0451216 B1  10/1991  European Pat. Off. .
0682040 A1  11/1995  European Pat. Off. .

OTHER PUBLICATIONS

Anderson et al., The Second Annual IBC Int. Conference on Antibody Engineering, Dec. 16–18, 1991.
Grosshard et al., Blood, 80:863–878, 1992.

*Primary Examiner*—Ronald B. Schwadron
*Attorney, Agent, or Firm*—Burns, Doane Swecker & Mathis, LLP

[57] ABSTRACT

Disclosed herein are therapeutic treatment protocols designed for the treatment of B cell lymphoma. These protocols are based upon therapeutic strategies which include the use of administration of immunologically active mouse/human chimeric anti-CD20 antibodies, radiolabeled anti-CD20 antibodies, and cooperative strategies comprising the use of chimeric anti-CD20 antibodies and radiolabeled anti-CD20 antibodies.

7 Claims, 21 Drawing Sheets

```
   LINKER #1 15bp|                      SV40 ORIGIN=332bp
GACGTCGCGG CCGCTCTAGG CCTCCAAAAA AGCCTCCTCA CTACTTCTGG AATAGCTCAG   60

AGGCCGAGGC GGCCTCGGCC TCTGCATAAA TAAAAAAAAT TAGTCAGCCA TGCATGGGGC  120

GGAGAATGGG CGGAACTGGG CGGAGTTAGG GGCGGGATGG GCGGAGTTAG GGGCGGGACT  180

ATGGTTGCTG ACTAATTGAG ATGCATGCTT TGCATACTTC TGCCTGCTGG GGAGCCTGGG  240

GACTTTCCAC ACCTGGTTGC TGACTAATTG AGATGCATGC TTTGCATACT TCTGCCTGCT  300
                                                  |LINKER #2=13bp|
GGGGAGCCTG GGACTTTCC ACACCCTAAC TGACACACAT TCCACAGAAT TAATTCCCCT   360
                                            347 8         360  1
AGTTATTAAT AGTAATCAAT TACGGGGTCA TTAGTTCATA GCCCATATAT GGAGTTCCGC  420

GTTACATAAC TTACGGTAAA TGGCCCGCCT GGCTGACCGC CCAACGACCC CCGCCCATTG  480
                          CMV PROMOTER-ENHANCER=567bp
ACGTCAATAA TGACGTATGT TCCCATAGTA ACGCCAATAG GGACTTTCCA TTGACGTCAA  540

TGGGTGGACT ATTTACGGTA AACTGCCCAC TTGGCAGTAC ATCAAGTGTA TCATATGCCA  600

AGTACGCCCC CTATTGACGT CAATGACGGT AAATGGCCCG CCTGGCATTA TGCCCAGTAC  660

ATGACCTTAT GGGACTTTCC TACTTGGCAG TACATCTACG TATTAGTCAT CGCTATTACC  720

ATGGTGATGC GGTTTTGGCA GTACATCAAT GGGCGTGGAT AGCGGTTTGA CTCACGGGGA  780

TTTCCAAGTC TCCACCCCAT TGACGTCAAT GGGAGTTTGT TTTGGCACCA AAATCAACGG  840

GACTTTCCAA AATGTCGTAA CAACTCCGCC CCATTGACGC AAATGGGCGG TAGGCGTGTA  900
                     |LINKER #3=76bp|
CGGTGGGAGG TCTATATAAG CAGAGCTGGG TACGTGAACC GTCAGATCGC CTGGAGACGC  960
                             727 8                LEADER=60bp
   Bgl II
CATCACAGAT CTCTCACCAT GAGGGTCCCC GCTCAGCTCC TGGGGCTCCT GCTGCTCTGG 1020
           978 9
              +1  |101 102                107 |108
CTCCCAGGTG CACGATGTGA TGGTACCAAG GTGGAAATCA AACGTACGGT GGCTGCACCA 1080
           1038 9                           1062 3 Bsi WI

TCTGTCTTCA TCTTCCCGCC ATCTGATGAG CAGTTGAAAT CTGGAACTGC CTCTGTTGTG 1140

TGCCTGCTGA ATAACTTCTA TCCCAGAGAG GCCAAAGTAC AGTGGAAGGT GGATAACGCC 1200
     HUMAN KAPPA CONSTANT 324bp 107 AMINO ACID & STOP CODON
CTCCAATCGG GTAACTCCCA GGAGAGTGTC ACAGAGCAGG ACAGCAAGGA CAGCACCTAC 1260

AGCCTCAGCA GCACCCTGAC GCTGAGCAAA GCAGACTACG AGAAACACAA AGTCTACGCC 1320

TGCGAAGTCA CCCATCAGGG CCTGAGCTCG CCCGTCACAA AGAGCTTCAA CAGGGGAGAG 1380
 STOP
 LIGHT
 CHAIN | Eco RI           LINKER #4=85bp
TGTTGAATTC AGATCCGTTA ACGGTTACCA ACTACCTAGA CTGGATTCGT GACAACATGC 1440
 1386 7
GGCCGTGATA TCTACGTATG ATCAGCCTCG ACTGTGCCTT CTAGTTGCCA GCCATCTGTT 1500
                                   1471 2
```

*FIG. 2A*

```
GTTTGCCCCT CCCCCGTGCC TTCCTTGACC CTGGAAGGTG CCACTCCCAC TGTCCTTTCC 1560
                       BGH poly A=231bp
TAATAAAATG AGGAAATTGC ATCGCATTGT CTGAGTAGGT GTCATTCTAT TCTGGGGGGT 1620

GGGGTGGGGC AGGACAGCAA GGGGGAGGAT TGGGAAGACA ATAGCAGGCA TGCTGGGGAT 1680
                               LINKER #5=15bp
GCGGTGGGCT CTATGGAACC AGCTGGGGCT CGACAGCTAT GCCAAGTACG CCCCCTATTG 1740
                    1702  3          1717  8

ACGTCAATGA CGGTAAATGG CCCGCCTGGC ATTATGCCCA GTACATGACC TTATGGGACT 1800

TTCCTACTTG GCAGTACATC TACGTATTAG TCATCGCTAT TACCATGGTG ATGCGGTTTT 1860
                       CMV PROMOTER-ENHANCER=334bp
GGCAGTACAT CAATGGGCGT GGATAGCGGT TTGACTCACG GGGATTTCCA AGTCTCCACC 1920

CCATTGACGT CAATGGGAGT TTGTTTTGGC ACCAAAATCA ACGGGACTTT CCAAAATGTC 1980

GTAACAACTC CGCCCCATTG ACGCAAATGG GCGGTAGGCG TGTACGGTGG GAGGTCTATA 2040
     LINKER #6=7bp                                        Sal I
TAAGCAGAGC TGGGTACGTC CTCACATTCA GTGATCAGCA CTGAACACAG ACCCGTCGAC 2100
      2051  2 2058  9       LEADER=51bp        Mlu I 2151  2 Nhe I
ATGGGTTGGA GCCTCATCTT GCTCTTCCTT GTCGCTGTTG CTACGCGTGT CGCTAGCACC 2160
START HEAVY CHAIN                                -5 -4 -3 114 115

AAGGGCCCAT CGGTCTTCCC CCTGGCACCC TCCTCCAAGA GCACCTCTGG GGGCACAGCG 2220

GCCCTGGGCT GCCTGGTCAA GGACTACTTC CCCGAACCGG TGACGGTGTC GTGGAACTCA 2280

GGCGCCCTGA CCAGCGGCGT GCACACCTTC CCGGCTGTCC TACAGTCCTC AGGACTCTAC 2340
                       HUMAN GAMMA 1 CONSTANT
TCCCTCAGCA GCGTGGTGAC CGTGCCCTCC AGCAGCTTGG GCACCCAGAC CTACATCTGC 2400
                993bp=330 AMINO ACID & STOP CODON
AACGTGAATC ACAAGCCCAG CAACACCAAG GTGGACAAGA AAGCAGAGCC CAAATCTTGT 2460

GACAAAACTC ACACATGCCC ACCGTGCCCA GCACCTGAAC TCCTGGGGGG ACCGTCAGTC 2520

TTCCTCTTCC CCCCAAAACC CAAGGACACC CTCATGATCT CCCGGACCCC TGAGGTCACA 2580

TGCGTGGTGG TGGACGTGAG CCACGAAGAC CCTGAGGTCA AGTTCAACTG GTACGTGGAC 2640

GGCGTGGAGG TGCATAATGC CAAGACAAAG CCGCGGGAGG AGCAGTACAA CAGCACGTAC 2700

CGTGTGGTCA GCGTCCTCAC CGTCCTGCAC CAGGACTGGC TGAATGGCAA GGACTACAAG 2760

TGCAAGGTCT CCAACAAAGC CCTCCCAGCC CCCATCGAGA AAACCATCTC CAAAGCCAAA 2820

GGGCAGCCCC GAGAACCACA GGTGTACACC CTGCCCCCAT CCCGGGATGA GCTGACCAGG 2880

AACCAGGTCA GCCTGACCTG CCTGGTCAAA GGCTTCTATC CCAGCGACAT CGCCGTGGAG 2940

TGGGAGAGCA ATGGGCAGCC GGAGAACAAC TACAAGACCA CGCCTCCCGT GCTGGACTCC 3000
```

FIG. 2B

```
GACGGCTCCT TCTTCCTCTA CAGCAAGCTC ACCGTGGACA AGAGCAGGTG GCAGCAGGGG 3060

AACGTCTTCT CATGCTCCGT GATGCATGAG GCTCTGCACA ACCACTACAC GCAGAAGAGC 3120
           STOP HEAVY CHAIN  |Bam HI           LINKER #7=81bp
CTCTCCCTGT CTCCGGGTAA ATGAGGATCC GTTAACGGTT ACCAACTACC TAGACTGGAT 3180
                     3144 5

TCGTGACAAC ATGCGGCCGT GATATCTACG TATGATCAGC CTCGACTGTG CCTTCTAGTT 3240
                                           3225  6

GCCAGCCATC TGTTGTTTGC CCCTCCCCCG TGCCTTCCTT GACCCTGGAA GGTGCCACTC 3300
         BOVINE GROWTH HORMONE POLYADENYLATION REGION=231bp
CCACTGTCCT TTCCTAATAA AATGAGGAAA TTGCATCGCA TTGTCTGAGT AGGTGTCATT 3360

CTATTCTGGG GGGTGGGGTG GGGCAGGACA GCAAGGGGGA GGATTGGGAA GACAATAGCA 3420
                                                   LINKER #8=34bp
GGCATGCTGG GGATGCGGTG GGCTCTATGG AACCAGCTGG GGCTCGACAG CGCTGGATCT 3480
                                 3456 7
CCCGATCCCC AGCTTTGCTT CTCAATTTCT TATTTGCATA ATGAGAAAAA AAGGAAAATT 3540
3490 1

AATTTTAACA CCAATTCAGT AGTTGATTGA GCAAATGCGT TGCCAAAAAG GATGCTTTAG 3600
             MOUSE BETA GLOBIN MAJOR PROMOTER=366bp
AGACAGTGTT CTCTGCACAG ATAAGGACAA ACATTATTCA GAGGGAGTAC CCAGAGCTGA 3660

GACTCCTAAG CCAGTGAGTG GCACAGCATT CTAGGGAGAA ATATGCTTGT CATCACCGAA 3720

GCCTGATTCC GTAGAGCCAC ACCTTGGTAA GGGCCAATCT GCTCACACAG GATAGAGAGG 3780

GCAGGAGCCA GGGCAGAGCA TATAAGGTGA GGTAGGATCA GTTGCTCCTC ACATTTGCTT 3840
              | LINKER #9=19bp       | 5' UNTRANSLATED DHFR=82bp
CTGACATAGT TGTGTTGGGA GCTTGGATAG CTTGACAGC TCAGGGCTGC GATTTCGCGC 3900
           3856 7              3875 6
                                                  |START DHFR
CAAACTTGAC GGCAATCCTA GCGTGAAGGC TGGTAGGATT TTATCCCCGC TGCCATATG 3960
                                                   3957 8
GTTCGACCAT TGAACTGCAT CGTCGCCGTG TCCCAAAATA TGGGGATTGG CAAGAACGGA 4020

GACCTACCCT GGCCTCCGCT CAGGAACGAG TTCAAGTACT TCCAAAGAAT GACCACAACC 4080

TCTTCAGTGG AAGGTAAACA GAATCTGGTG ATTATGGGTA GGAAAACCTG GTTCTCCATT 4140
           MOUSE DHFR=564bp=187 AMINO ACID & STOP CODON
CCTGAGAAGA ATCGACCTTT AAAGGACAGA ATTAATATAG TTCTCAGTAG AGAACTCAAA 4200

GAACCACCAC GAGGAGCTCA TTTTCTTGCC AAAAGTTTGG ATGATGCCTT AAGACTTATT 4260

GAACAACCGG AATTGGCAAG TAAAGTAGAC ATGGTTTGGA TAGTCGGAGG CAGTTCTGTT 4320

TACCAGGAAG CCATGAATCA ACCAGGCCAC CTTAGACTCT TTGTGACAAG GATCATGCAG 4380

GAATTTGAAA GTGACACGTT TTTCCCAGAA ATTGATTTGG GGAAATATAA ACTTCTCCCA 4440

GAATACCCAG GCGTCCTCTC TGAGGTCCAG GAGGAAAAAG GCATCAAGTA TAAGTTTGAA 4500
```

*FIG. 2C*

```
                            STOP DHFR
GTCTACGAGA AGAAAGAC TA A CAGGAAGAT GCTTTCAAGT TCTCTGCTCC CCTCCTAAAG  4560
                   4521  2
    3' UNTRANSLATED DHFR=82bp                    LINKER #10=10bp
TCATGCATTT TTATAAGACC ATGGGACTTT TGCTGGCTTT AGA TCAGC  T CGA CTGT  C  4620
                                           4603  4     4613  4
TTCTAGTTGC CAGCCATCTG TTGTTTGCCC CTCCCCCGTG CCTTCCTTGA CCCTGGAAGG  4680
      BOVINE GROWTH HORMONE POLYADENYLATION REGION=231bp
TGCCACTCCC ACTGTCCTTT CCTAATAAAA TGAGGAAATT GCATCGCATT GTCTGAGTAG  4740

GTGTCATTCT ATTCTGGGGG GTGGGGTGGG GCAGGACAGC AAGGGGGAGG ATTGGGAAGA  4800
                                           | LINKER #11=17bp
CAATAGCAGG CATGCTGGGG ATGCGGTGGG CTCTATGGAA CCAG CTGGGG CTCGAGCTAC  4860
                                               4844  5
T AGCTTTGCT TCTCAATTTC TTATTTGCAT AATGAGAAAA AAAGGAAAAT TAATTTTAAC  4920

ACCAATTCAG TAGTTGATTG AGCAAATGCG TTGCCAAAAA GGATGCTTTA GAGACAGTGT  4980
         MOUSE BETA GLOBIN MAJOR PROMOTER=366bp
TCTCTGCACA GATAAGGACA AACATTATTC AGAGGGAGTA CCCAGAGCTG AGACTCCTAA  5040

GCCAGTGAGT GGCACAGCAT TCTAGGGAGA AATATGCTTG TCATCACCGA AGCCTGATTC  5100

CGTAGAGCCA CACCTTGGTA AGGGCCAATC TGCTCACACA GGATAGAGAG GGCAGGAGCC  5160

AGGGCAGAGC ATATAAGGTG AGGTAGGATC AGTTGCTCCT CACATTTGCT TCTGACATAG  5220
          |   LINKER #12=21bp     |START NEO
TTGTGT T GGG AGCTTGGATC GATCCTC TAT G GTTGAACAA GATGGATTGC ACGCAGGTTC  5280
     5227  8                   5248  9
TCCGGCCGCT TGGGTGGAGA GGCTATTCGG CTATGACTGG GCACAACAGA CAATCGGCTG  5340

CTCTGATGCC GCCGTGTTCC GGCTGTCAGC GCAGGGGCGC CCGGTTCTTT TTGTCAAGAC  5400
             NEOMYCIN PHOSPHOTRANSFERASE
CGACCTGTCC GGTGCCCTGA ATGAACTGCA GGACGAGGCA GCGCGGCTAT CGTGGCTGGC  5460
         795bp=264 AMINO ACIDS & STOP CODON
CACGACGGGC GTTCCTTGCG CAGCTGTGCT CGACGTTGTC ACTGAAGCGG GAAGGGACTG  5520

GCTGCTATTG GGCGAAGTGC CGGGGCAGGA TCTCCTGTCA TCTCACCTTG CTCCTGCCGA  5580

GAAAGTATCC ATCATGGCTG ATGCAATGCG GCGGCTGCAT ACGCTTGATC CGGCTACCTG  5640

CCCATTCGAC CACCAAGCGA AACATCGCAT CGAGCGAGCA CGTACTCGGA TGGAAGCCGG  5700

TCTTGTCGAT CAGGATGATC TGGACGAAGA GCATCAGGGG CTCGCGCCAG CCGAACTGTT  5760

CGCCAGGCTC AAGGCGCGCA TGCCCGACGG CGAGGATCTC GTCGTGACCC ATGGCGATGC  5820

CTGCTTGCCG AATATCATGG TGGAAAATGG CCGCTTTTCT GGATTCATCG ACTGTGGCCG  5880

GCTGGGTGTG GCGGACCGCT ATCAGGACAT AGCGTTGGCT ACCCGTGATA TTGCTGAAGA  5940

GCTTGGCGGC GAATGGGCTG ACCGCTTCCT CGTGCTTTAC GGTATCGCCG CTTCCCGATTC 6000
```

*FIG. 2D*

```
                                            STOP NEO
GCAGCGCATC GCCTTCTATC GCCTTCTTGA CGAGTTCTTC TGAGCGGGAC TCTGGGGTTC 6060
                                            6043 4
GAAATGACCG ACCAAGCGAC GCCCAACCTG CCATCACGAG ATTTCGATTC CACCGCCGCC 6120
                    3' UNTRANSLATED NEO=173bp
TTCTATGAAA GGTTGGGCTT CGGAATCGTT TTCCGGGACG CCGGCTGGAT GATCCTCCAG 6180
CGCGGGGATC TCATGCTGGA GTTCTTCGCC CACCCCAACT TGTTTATTGC AGCTTATAAT 6240
                                       6216 7
GGTTACAAAT AAAGCAATAG CATCACAAAT TTCACAAATA AAGCATTTTT TTCACTGCAT 6300
           SV40 POLY A EARLY=133bp         LINKER #13=19bp
TCTAGTTGTG GTTTGTCCAA ACTCATCAAT CTATCTTATC ATGTCTGGAT CGCGGCCGCG 6360
                                            6349 50
ATCCCGTCGA GAGCTTGGCG TAATCATGGT CATAGCTGTT TCCTGTGTGA AATTGTTATC 6420
   6368 9
CGCTCACAAT TCCACACAAC ATACGAGCCG GAAGCATAAA GTGTAAAGCC TGGGGTGCCT 6480
AATGAGTGAG CTAACTCACA TTAATTGCGT TGCGCTCACT GCCCGCTTTC CAGTCGGGAA 6540
ACCTGTCGTG CCAGCTGCAT TAATGAATCG GCCAACGCGC GGGGAGAGGC GGTTTGCGTA 6600
                              PVC 19
TTGGGCGCTC TTCCGCTTCC TCGCTCACTG ACTCGCTGCG CTCGGTCGTT CGGCTGCGGC 6660
GAGCGGTATC AGCTCACTCA AAGGCGGTAA TACGGTTATC CACAGAATCA GGGGATAACG 6720
CAGGAAAGAA CATGTGAGCA AAAGGCCAGC AAAAGGCCAG GAACCGTAAA AAGGCCGCGT 6780
          6792=BACTERIAL ORIGIN OF REPLICATION
TGCTGGCGTT TTTCCATAGG CTCCGCCCCC CTGACGAGCA TCACAAAAAT CGACGCTCAA 6840
GTCAGAGGTG GCGAAACCCG ACAGGACTAT AAAGATACCA GGCGTTTCCC CCTGGAAGCT 6900
CCCTCGTGCG CTCTCCTGTT CCGACCCTGC CGCTTACCGG ATACCTGTCC GCCTTTCTCC 6960
CTTCGGGAAG CGTGGCGCTT TCTCAATGCT CACGCTGTAG GTATCTCAGT TCGGTGTAGG 7020
TCGTTCGCTC CAAGCTGGGC TGTGTGCACG AACCCCCCGT TCAGCCCGAC CGCTGCGCCT 7080
TATCCGGTAA CTATCGTCTT GAGTCCAACC CGGTAAGACA CGACTTATCG CCACTGGCAG 7140
CAGCCACTGG TAACAGGATT AGCAGAGCGA GGTATGTAGG CGGTGCTACA GAGTTCTTGA 7200
AGTGGTGGCC TAACTACGGC TACACTAGAA GGACAGTATT TGGTATCTGC GCTCTGCTGA 7260
AGCCAGTTAC CTTCGGAAAA AGAGTTGGTA GCTCTTGATC CGGCAAACAA ACCACCGCTG 7320
GTAGCGGTGG TTTTTTTGTT TGCAAGCAGC AGATTACGCG CAGAAAAAAA GGATCTCAAG 7380
AAGATCCTTT GATCTTTTCT ACGGGGTCTG ACGCTCAGTG AACGAAAAC TCACGTTAAG 7440
GGATTTTGGT CATGAGATTA TCAAAAAGGA TCTTCACCTA GATCCTTTTA AATTAAAAAT 7500
```

*FIG. 2E*

```
                                        STOP BETA LACTAMASE
GAAGTTTTAA ATCAATCTAA AGTATATATG AGTAAACTTG GTCTGACAGT TACCAATGCT 7560
                                                      7550
TAATCAGTGA GGCACCTATC TCAGCGATCT GTCTATTTCG TTCATCCATA GTTGCCTGAC 7620

TCCCCGTCGT GTAGATAACT ACGATACGGG AGGGCTTACC ATCTGGCCCC AGTGCTGCAA 7680

TGATACCGCG AGACCCACGC TCACCGGCTC CAGATTTATC AGCAATAAAC CAGCCAGCCG 7740
                         BETA LACTAMASE=861bp
GAAGGGCCGA GCGCAGAAGT GGTCCTGCAA CTTTATCCGC CTCCATCCAG TCTATTAATT 7800
            286 AMINO ACID & STOP CODON
GTTGCCGGGA AGCTAGAGTA AGTAGTTCGC CAGTTAATAG TTTGCGCAAC GTTGTTGCCA 7860

TTGCTACAGG CATCGTGGTG TCACGCTCGT CGTTTGGTAT GGCTTCATTC AGCTCCGGTT 7920

CCCAACGATC AAGGCGAGTT ACATGATCCC CCATGTTGTG CAAAAAAGCG GTTAGCTCCT 7980

TCGGTCCTCC GATCGTTGTC AGAAGTAAGT TGGCCGCAGT GTTATCACTC ATGGTTATGG 8040

CAGCACTGCA TAATTCTCTT ACTGTCATGC CATCCGTAAG ATGCTTTTCT GTGACTGGTG 8100

AGTACTCAAC CAAGTCATTC TGAGAATAGT GTATGCGGCG ACCGAGTTGC TCTTGCCCGG 8160

CGTCAATACG GGATAATACC GCGCCACATA GCAGAACTTT AAAAGTGCTC ATCATTGGAA 8220

AACGTTCTTC GGGGCGAAAA CTCTCAAGGA TCTTACCGCT GTTGAGATCC AGTTCGATGT 8280

AACCCACTCG TGCACCCAAC TGATCTTCAG CATCTTTTAC TTTCACCAGC GTTTCTGGGT 8340

GAGCAAAAAC AGGAAGGCAA AATGCCGCAA AAAAGGGAAT AAGGGCGACA CGGAAATGTT 8400
          START BETA LACTAMASE
GAATACTCAT ACTCTTCCTT TTTCAATATT ATTGAAGCAT TTATCAGGGT TATTGTCTCA 8460
        8410
TGAGCGGATA CATATTTGAA TGTATTTAGA AAAATAAACA AATAGGGGTT CCGCGCACAT 8520

TTCCCCGAAA AGTGCCACCT
```

FIG. 2F

```
           LINKER #1=15bp
       GACGTCGCGG CCGCTCTAGG CCTCCAAAAA AGCCTCCTCA CTACTTCTGG AATAGCTCAG    60
                  15 6
       AGGCCGAGGC GGCCTCGGCC TCTGCATAAA TAAAAAAAAT TAGTCACCCA TGCATGGGGC   120
                       SV40 ORIGIN=332bp
       GGAGAATGGG CGGAACTGGG CGGAGTTAGG GGCGGGATGG GCGGAGTTAG GGGCGGGACT   180

ATGGTTGCTG ACTAATTGAG ATGCATGCTT TGCATACTTC TGCCTGCTGG GGAGCCTGGG   240

GACTTTCCAC ACCTGGTTGC TGACTAATTG AGATGCATGC TTTGCATACT TCTGCCTGCT   300

LINKER #2=13bp
       GGGGAGCCTG GGGACTTTCC ACACCCTAAC TGACACACAT TCCACAGAAT TAATTCCCCT   360
                                                       347 8
       AGTTATTAAT AGTAATCAAT TACGGGGTCA TTAGTTCATA GCCCATATAT GGAGTTCCGC   420

GTTACATAAC TTACGGTAAA TGGCCCGCCT GGCTGACCGC CCAACGACCC CCGCCCATTG   480

ACGTCAATAA TGACGTATGT TCCCATAGTA ACGCCAATAG GGACTTTCCA TTGACGTCAA   540
                       CVM PROMOTER-ENHANCER=567bp
       TGGGTGGACT ATTTACGGTA AACTGCCCAC TTGGCAGTAC ATCAAGTGTA TCATATGCCA   600

AGTACGCCCC CTATTGACGT CAATGACGGT AAATGGCCCG CCTGGCATTA TGCCCAGTAC   660

ATGACCTTAT GGGACTTTCC TACTTGGCAG TACATCTACG TATTAGTCAT CGCTATTACC   720

ATGGTGATGC GGTTTTGGCA GTACATCAAT GGGCGTGGAT AGCGGTTTGA CTCACGGGGA   780

TTTCCAAGTC TCCACCCCAT TGACGTCAAT GGGAGTTTGT TTTGGCACCA AAATCAACGG   840

GACTTTCCAA AATGTCGTAA CAACTCCGCC CCATTGACGC AAATGGGCGG TAGGCGTGTA   900
                                LINKER #3=7bp
       CGGTGGGAGG TCTATATAAG CAGAGCTGGG TACGTGAACC GTCAGATCGC CTGGAGACGC   960
                                927 8   934 5
           Bgl 2          START LIGHT CHAIN      NATURAL LEADER=66bp
       CATCACAGAT CTCTCACTAT GGATTTTCAG GTGCAGATTA TCAGCTTCCT GCTAATCAGT  1020
                        978 9

GCTTCAGTCA TAATGTCCAG AGGACAAATT GTTCTCTCCC AGTCTCCAGC AATCCTGTCT  1080
                             1044 5 +1
       GCATCTCCAG GGGAGAAGGT CACAATGACT TGCAGGGCCA GCTGAAGTGT AAGTTACATC  1140

CACTGGTTCC AGCAGAAGCC AGGATCCTCC CCCAAACCCT GGATTTATGC CACATCCAAC  1200
                         LIGHT CHAIN VARIABLE REGION 318bp 106 AMINO ACID
       CTGGCTTCTG GAGTCCCTGT TCGCTTCAGT GGCAGTGGGT CTGGGACTTC TTACTCTCTC  1260

ACCATCAGCA GAGTGGAGGC TGAAGATGCT GCCACTTATT ACTGCCAGCA GTGGACTAGT  1320
                                                         BsiWI
       AACCCACCCA CGTTCGGAGG GGGGACCAAG CTGGAAATCA AACGTACGGT GGCTGCACCA  1380
                                                         1362 3
       TCTGTCTTCA TCTTCCCGCC ATCTGATGAG CAGTTGAAAT CTGGAACTGC CTCTGTTGTG  1440

TGCCTGCTGA ATAACTTCTA TCCCAGAGAG GCCAAAGTAC AGTGGAAGGT GGATAACGCC  1500
```

FIG. 3A

HUMAN KAPPA CONSTANT=324bp=107 AMINO ACID & STOP CODON
```
CTCCAATCGG GTAACTCCCA GGAGAGTGTC ACAGAGCAGG ACAGCAAGGA CAGCACCTAC 1560

AGCCTCAGCA GCACCCTGAC GCTGAGCAAA GCAGACTACG AGAAACACAA AGTCTACGCC 1620

TGCGAAGTCA CCCATCAGGG CCTGAGCTCG CCCGTCACAA AGAGCTTCAA CAGGGGAGAG 1680
```
STOP
LIGHT
CHAIN Eco RI                LINKER #4=81bp
```
TGTTGAATTC AGATCCGTTA ACGGTTACCA ACTACCTAGA CTGGATTCGT GACAACATGC 1740
  1646 7

GGCCGTGATA TCTACGTATG ATCAGCCTCG ACTGTGCCTT CTAGTTGCCA GCCATCTGTT 1800
                              1771 2

GTTTGCCCCT CCCCCGTGCC TTCCTTGACC CTGGAAGGTG CCACTCCCAC TGTCCTTTCC 1860

TAATAAAATG AGGAAATTGC ATCGCATTGT CTGAGTAGGT GTCATTCTAT TCTGGGGGGT 1920
```
BOVINE GROWTH HORMONE POLYADENYLATION REGION=231bp
```
GGGGTGGGGC AGGACAGCAA GGGGGAGGAT TGGGAAGACA ATAGCAGGCA TGCTGGGGAT 1980
```
            LINKER #5=15bp
```
GCGGTGGGCT CTATGGAACC AGCTGGGGCT CGACAGCTAT GCCAAGTACG CCCCCTATTG 2040
                      2002 3        2017 8

ACGTCAATGA CGGTAAATGG CCCGCCTGGC ATTATGCCCA GTACATGACC TTATGGGACT 2100

TTCCTACTTG GCAGTACATC TACGTATTAG TCATCGCTAT TACCATGGTG ATGCGGTTTT 2160
```
CMV PROMOTER-ENHANCER=334bp
```
GGCAGTACAT CAATGGGCGT GGATAGCGGT TTGACTCACG GGGATTTCCA AGTCTCCACC 2220

CCATTGACGT CAATGGGAGT TTGTTTTGGC ACCAAAATCA ACGGGACTTT CCAAAATGTC 2280

GTAACAACTC CGCCCCATTG ACGCAAATGG GCGGTAGGCG TGTACGGTGG GAGGTCTATA 2340
```
    LINKER #6=7bp                                           Sal I
```
TAAGCAGAGC TGGGTACGTC CTCACATTCA GTGATCAGCA CTGAACACAG ACCCGTCGAC 2400
START      2351 2 2358 9
```
HEAVY CHAIN          SYNTHETIC & NATURAL LEADER    Mlu I    2457 8
```
ATGGGTTGGA GCCTCATCTT GCTCTTCCTT GTCGCTGTTG CTACGCGTGT CCTGTCCCAG 2460
2401                                              -5 -4 -3 -2 -1 +1

GTACAACTGC AGCAGCCTGG GGCTGAGCTG GTGAAGCCTG GGCCTCAGT GAAGATGTCC 2520

TGCAAGGCTT CTGGCTACAC ATTTACCAGT TACAATATGC ACTGGGTAAA ACAGACACCT 2580
```
HEAVY CHAIN VARIABLE=363bp=121 AMINO ACID
```
GGTCGGGGCC TGGAATGGAT TGGAGCTATT TATCCCGGAA ATGGTGATAC TTCCTACAAT 2640

CAGAAGTTCA AAGGCAAGGC CACATTGACT GCAGACAAAT CCTCCAGCAC AGCCTACATG 2700

CAGCTCAGCA GCCTGACATC TGAGGACTCT GCGGTCTATT ACTGTGCAAG ATCGACTTAC 2760

TACGGCGGTG ACTGGTACTT CAATGTCTGG GGCGCAGGGA CCACGGTCAC CGTCTCTGCA 2820
```
Nhe I
```
GCTAGCACCA AGGGCCCATC GGTCTTCCCC CTGGCACCCT CCTCCAAGAG CACCTCTGGG 2880

GGCACAGCGG CCCTGGGCTG CCTGGTCAAG GACTACTTCC CCGAACCGGT GACGGTGTCG 2940
```
HUMAN GAMMA 1 CONSTANT=993bp
```
TGGAACTCAG GCGCCCTGAC CAGCGGCGTG CACACCTTCC CGGCTGTCCT ACAGTCCTCA 3000
```

FIG. 3B

```
                     330 AMINO ACID & STOP CODON
GGACTCTACT CCCTCAGCAG CGTGGTGACC GTGCCCTCCA GCAGCTTGGG CACCCAGACC 3060

TACATCTGCA ACGTGAATCA CAAGCCCAGC AACACCAAGG TGGACAAGAA AGCAGAGCCC 3120

AAATCTTGTG ACAAAACTCA CACATGCCCA CCGTGCCCAG CACCTGAACT CCTGGGGGGA 3180

CCGTCAGTCT TCCTCTTCCC CCCAAAACCC AAGGACACCC TCATGATCTC CCGGACCCCT 3240

GAGGTCACAT GCGTGGTGGT GGACGTGAGC CACGAAGACC CTGAGGTCAA GTTCAACTGG 3300

TACGTGGACG GCGTGGAGGT GCATAATGCC AAGACAAAGC CGCGGGAGGA GCAGTACAAC 3360

AGCACGTACC GTGTGGTCAG CGTCCTCACC GTCCTGCACC AGGACTGGCT GAATGGCAAG 3420

GAGTACAAGT GCAAGGTCTC CAACAAAGCC CTCCCAGCCC CCATCGAGAA AACCATCTCC 3480

AAAGCCAAAG GGCAGCCCCG AGAACCACAG GTGTACACCC TGCCCCCATC CCGGGATGAG 3540

CTGACCAAGA ACCAGGTCAG CCTGACCTGC CTGGTCAAAG GCTTCTATCC CAGCGACATC 3600

GCCGTGGAGT GGGAGAGCAA TGGGCAGCCG GAGAACAACT ACAAGACCAC GCCTCCCGTG 3660

CTGGACTCCG ACGGCTCCTT CTTCCTCTAC AGCAAGCTCA CCGTGGACAA GAGCAGGTGG 3720

CAGCAGGGGA ACGTCTTCTC ATGCTCCGTG ATGCATGAGG CTCTGCACAA CCACTACACG 3780
                STOP HEAVY CHAIN  Bam HI    LINKER #7=81bp
CAGAAGAGCC TCTCCCTGTC TCCGGGTAAA TGAGGATCCG TTAACGGTTA CCAACTACCT 3840
                              3813 4
AGACTGGATT CGTGACAACA TGCGGCCGTG ATATCTACGT ATGATCAGCC TCGACTGTGC 3900
                                                       3894 5
CTTCTAGTTG CCAGCCATCT GTTGTTTGCC CCTCCCCCGT GCCTTCCTTG ACCCTGGAAG 3960

GTGCCACTCC CACTGTCCTT TCCTAATAAA ATGAGGAAAT TGCATCGCAT TGTCTGAGTA 4020
        BOVINE GROWTH HORMONE POLYADENYLATION REGION=231bp
GGTGTCATTC TATTCTGGGG GGTGGGGTGG GGCAGGACAG CAAGGGGGAG GATTGGGAAG 4080
                                            LINKER #8=34bp
ACAATAGCAG GCATGCTGGG GATGCGGTGG GCTCTATGGA ACCAGCTGGG GCTCGACAGC 4140
                                             4125 6
GCTGGATCTC CCGATCCCCA GCTTTGCTTC TCAATTTCTT ATTTGCATAA TGAGAAAAAA 4200

AGGAAAATTA ATTTTAACAC CAATTCAGTA GTTGATTGAG CAAATGCGTT GCCAAAAAGG 4260
             MOUSE BETA GLOBIN MAJOR PROMOTER=366bp
ATGCTTTAGA GACAGTGGTC TCTGCACAGA TAAGGACAAA CATTATTCAG AGGGAGTACC 4320

CAGAGCTGAG ACTCCTAAGC CAGTGAGTGG CACAGCATTC TAGGGAGAAA TATGCTTGTC 4380

ATCACCGAAG CCTGATTCCG TAGAGCCACA CCTTGGTAAG GGCCAATCTG CTCACACAGG 4440

ATAGAGAGGG CAGGAGCCAG GGCAGAGCAT ATAAGGTGAG GTAGGATCAG TTGCTCCTCA 4500
```

*FIG. 3C*

```
                            LINKER #9=19bP   5' UNTRANSLATED DHFR=82bp
CATTTGCTTC TGACATAGTT GTGTTGGGAG CTTGGATAGC TTGGACAGCT CAGGGCTGCG  4560
                           4525 6            4544 5

ATTTCGCGCC AAACTTGACG GCAATCCTAG CGTGAAGGCT GGTAGGATTT TATCCCCGCT  4620
          START DHFR
GCCATCATGG TTCGACCATT GAACTGCATC GTCGCCGTGT CCCAAAATAT GGGGATTGGC  4680
     4626 7

AAGAACGGAG ACCTACCCTG GCCTCCGCTC AGGAACGAGT TCAAGTACTT CCAAAGAATG  4740

ACCACAACCT CTTCAGTGGA AGGTAAACAG AATCTGGTGA TTATGGGTAG GAAAACCTGG  4800
              DHFR=564bp=187 AMINO ACID & STOP CODON
TTCTCCATTC CTGAGAAGAA TCGACCTTTA AAGGACAGAA TTAATATAGT TCTCAGTAGA  4860

GAACTCAAAG AACCACCACG AGGAGCTCAT TTTCTTGCCA AAAGTTTGGA TGATGCCTTA  4920

AGACTTATTG AACAACCGGA ATTGGCAAGT AAAGTAGACA TGGTTTGGAT AGTCGGAGGC  4980

AGTTCTGTTT ACCAGGAAGC CATGAATCAA CCAGGCCACC TTAGACTCTT TGTGACAAGG  5040

ATCATGCAGG AATTTGAAAG TGACACGTTT TTCCCAGAAA TTGATTTGGG GAAATATAAA  5100

CTTCTCCCAG AATACCCAGG CGTCCTCTCT GAGGTCCAGG AGGAAAAAGG CATCAAGTAT  5160
                        STOP DHFR    3' UNTRANSLATED DHFR=82bp
AAGTTTGAAG TCTACGAGAA GAAAGACTAA CAGGAAGATG CTTTCAAGTT CTCTGCTCCC  5220
                          5140 1                              LINKER #10
CTCCTAAAGC TATGCATTTT TATAAGACCA TGGGACTTTT GCTGGCTTTA GATCAGCCTC  5280
=10bp                                                       5272 3
GACTGTGCCT TCTAGTTGCC AGCCATCTGT TGTTTGCCCC TCCCCCGTGC CTTCCTTGAC  5340
       BOVINE GROWTH HORMONE POLYADENYLATION=231bp
CCTGGAAGGT GCCACTCCCA CTGTCCTTTC CTAATAAAAT GAGGAAATTG CATCGCATTG  5400

TCTGAGTAGG TGTCATTCTA TTCTGGGGGG TGGGGTGGGG CAGGACAGCA AGGGGGAGGA  5460
                                                             LINKER #11
TTGGGAAGAC AATAGCAGGC ATGCTGGGGA TGCGGTGGGC TCTATGGAAC CAGCTGGGGC  5520
 =17bp                                                      5513 4
TCGAGCTACT AGCTTTGCTT CTCAATTTCT TATTTGCATA ATGAGAAAAA AAGGAAAATT  5580
       5530 1
AATTTTAACA CCAATTCAGT AGTTGATTGA GCAAATGCGT TGCCAAAAAG GATGCTTTAG  5640
            MOUSE BETA GLOBIN MAJOR PROMOTER=366bp
AGACAGTGTT CTCTGCACAG ATAAGGACAA CTAGGGAGAA ATATGCTTGT CATCACCGAA  5700

GACTCCTAAG CCAGTGAGTG GCACAGCATT CTAGGGAGAA ATATGCTTGT CATCACCGAA  5760

GCCTGATTCC GTAGAGCCAC ACCTTGGTAA GGGCCAATCT GCTCACACAG GATAGAGAGG  5820

GCAGGAGCCA GGGCAGAGCA TATAAGGTGA GGTAGGATCA GTTGCTCCTC ACATTTGCTT  5880
               LINKER #12=21bp    START NEO
CTGACATAGT TGTGTTGGGA GCTTGGATCG ATCCTCTATG GTTGAACAAG ATGGATTGCA  5940
          5896 7               5917 8
CGCAGGTTCT CCGGCCGCTT GGGTGGAGAG GCTATTCGGC TATGACTGGG CACAACAGAC  6000
```

FIG. 3D

```
AATCGGCTGC TCTGATGCCG CCGTGTTCCG GCTGTCAGCG CAGGGGCGCC CGGTTCTTTT 6060
       NEOMYCIN PHOSPHOTRANSFERASE=795bP=264 AMINO ACID & STOP CODON
TGTCAAGACC GACCTGTCCG GTGCCCTGAA TGAACTGCAG GACGAGGCAG CGCGGCTATC 6120
GTGGCTGGCC ACGACGGGCG TTCCTTGCGC AGCTGTGCTC GACGTTGTCA CTGAAGCGGG 6180
AAGGGACTGG CTGCTATTGG GCGAAGTGCC GGGGCAGGAT CTCCTGTCAT CTCACCTTGC 6240
TCCTGCCGAG AAAGTATCCA TCATGGCTGA TGCAATGCGG CGGCTGCATA CGCTTGATCC 6300
GGCTACCTGC CCATTCGACC ACCAAGCGAA ACATCGCATC GAGCGAGCAC GTACTCGGAT 6360
GGAAGCCGGT CTTGTCGATC AGGATGATCT GGACGAAGAG CATCAGGGGC TCGCGCCAGC 6420
CGAACTGTTC GCCAGGCTCA AGGCGCGCAT GCCCGACGGC GAGGATCTCG TCGTGACCCA 6480
TGGCGATGCC TGCTTGCCGA ATATCATGGT GGAAAATGGC CGCTTTTCTG GATTCATCGA 6540
CTGTGGCCGG CTGGGTGTGG CGGACCGCTA TCAGGACATA GCGTTGGCTA CCCGTGATAT 6600
TGCTGAAGAG CTTGGCGGCG AATGGGCTGA CCGCTTCCTC GTGCTTTACG GTATCGCCGC 6660
                                          STOP NEO|
TCCCGATTCG CAGCGCATCG CCTTCTATCG CCTTCTTGAC GAGTTCTTCT GAGCGGGACT 6720
                                                  6712 3
CTGGGGTTCG AAATGACCGA CCAAGCGACG CCCAACCTGC CATCACGAGA TTTCGATTCC 6780
                     3' UNTRANSLATED NEO=173bp
ACCGCCGCCT TCTATGAAAG GTTGGGCTTC GGAATCGTTT TCCGGGACGC CGGCTGGATG 6840
ATCCTCCAGC GCGGGGATCT CATGCTGGAG TTCTTCGCCC ACCCCAACTT GTTTATTGCA 6900
                                            6885 6
GCTTATAATG GTTACAAATA AAGCAATAGC ATCACAAATT TCACAAATAA AGCATTTTTT 6960
              SV40 EARLY POLYADENYLATION REGION=133bp
TCACTGCATT CTAGTTGTGG TTTGTCCAAA CTCATCAATC TATCTTATCA TGTCTGGATC 7020
     LINKER #13=19bp                                       7018 9
GCGGCCGCGA TCCCGTCGAG AGCTTGGCGT AATCATGGTC ATAGCTGTTT CCTGTGTGAA 7080
           7037 8
                                 PUC 19
ATTGTTATCC GCTCACAATT CCACACAACA TACGAGCCGG AAGCATAAAG TGTAAAGCCT 7140
GGGGTGCCTA ATGAGTGAGC TAACTCACAT TAATTGCGTT GCGCTCACTG CCCGCTTTCC 7200
AGTCGGGAAA CCTGTCGTGC CAGCTGCATT AATGAATCGG CCAACGCGCG GGGAGAGGCG 7260
GTTTGCGTAT TGGGCGCTCT TCCGCTTCCT CGCTCACTGA CTCGCTGCGC TCGGTCGTTC 7320
GGCTGCGGCG AGCGGTATCA GCTCACTCAA AGGCGGTAAT ACGGTTATCC ACAGAATCAG 7380
GGGATAACGC AGGAAAGAAC ATGTGAGCAA AAGGCCAGCA AAAGGCCAGG AACCGTAAAA 7440
             7461=BACTERIAL ORIGIN OF REPLICATION
AGGCCGCGTT GCTGGCGTTT TTCCATAGGC TCCGCCCCCC TGACGAGCAT CACAAAAATC 7500
```

FIG. 3E

```
GACGCTCAAG TCAGAGGTGG CGAAACCCGA CAGGACTATA AAGATACCAG GCGTTTCCCC 7560
CTGGAAGCTC CCTCGTGCGC TCTCCTGTTC CGACCCTGCC GCTTACCGGA TACCTGTCCG 7620
CCTTTCTCCC TTCGGGAAGC GTGGCGCTTT CTCAATGCTC ACGCTGTAGG TATCTCAGTT 7680
CGGTGTAGGT CGTTCGCTCC AAGCTGGGCT GTGTGCACGA ACCCCCCGTT CAGCCCGACC 7740
GCTGCGCCTT ATCCGGTAAC TATCGTCTTG AGTCCAACCC GGTAAGACAC GACTTATCGC 7800
CACTGGCAGC AGCCACTGGT AACAGGATTA GCAGAGCGAG GTATGTAGGC GGTGCTACAG 7860
AGTTCTTGAA GTGGTGGCCT AACTACGGCT ACACTAGAAG GACAGTATTT GGTATCTGCG 7920
CTCTGCTGAA GCCAGTTACC TTCGGAAAAA GAGTTGGTAG CTCTTGATCC GGCAAACAAA 7980
CCACCGCTGG TAGCGGTGGT TTTTTTGTTT GCAAGCAGCA GATTACGCGC AGAAAAAAAG 8040
GATCTCAAGA AGATCCTTTG ATCTTTTCTA CGGGGTCTGA CGCTCAGTGG AACGAAAACT 8100
CACGTTAAGG GATTTTGGTC ATGAGATTAT CAAAAAGGAT CTTCACCTAG ATCCTTTTAA 8160
                                                          |STOP
ATTAAAAATG AAGTTTTAAA TCAATCTAAA GTATATATGA GTAAACTTGG TCTGACAGTT 8220
|BETA LACTAMASE|
ACCAATGCTT AATCAGTGAG GCACCTATCT CAGCGATCTG TCTATTTCGT TCATCCATAG 8280
TTGCCTGACT CCCCGTCGTG TAGATAACTA CGATACGGGA GGGCTTACCA TCTGGCCCCA 8340
GTGCTGCAAT GATACCGCGA GACCCACGCT CACCGGCTCC AGATTTATCA GCAATAAACC 8400
          BETA LACTAMASE=861bp=286 AMINO ACID & STOP CODON
AGCCAGCCGG AAGGGCCGAG CGCAGAAGTG GTCCTGCAAC TTTATCCGCC TCCATCCAGT 8460
CTATTAATTG TTGCCGGGAA GCTAGAGTAA GTAGTTCGCC AGTTAATAGT TTGCGCAACG 8520
TTGTTGCCAT TGCTACAGGC ATCGTGGTGT CACGCTCGTC GTTTGGTATG GCTTCATTCA 8580
GCTCCGGTTC CCAACGATCA AGGCGAGTTA CATGATCCCC CATGTTGTGC AAAAAAGCGG 8640
TTAGCTCCTT CGGTCCTCCG ATCGTTGTCA GAAGTAAGTT GGCCGCAGTG TTATCACTCA 8700
TGGTTATGGC AGCACTGCAT AATTCTCTTA CTGTCATGCC ATCCGTAAGA TGCTTTTCTG 8760
TGACTGGTGA GTACTCAACC AAGTCATTCT GAGAATAGTG TATGCGGCGA CCGAGTTGCT 8820
CTTGCCCGGC GTCAATACGG GATAATACCG CGCCACATAG CAGAACTTTA AAAGTGCTCA 8880
TCATTGGAAA ACGTTCTTCG GGGCGAAAAC TCTCAAGGAT CTTACCGCTG TTGAGATCCA 8940
GGTCGATGTA ACCCACTCGT GCACCCAACT GATCTTCAGC ATCTTTTACT TTCACCAGCG 9000
TTTCTGGGTG AGCAAAAACA GGAAGGCAAA ATGCCGCAAA AAAGGGAATA AGGGCGACAC 9060
                   | START BETA LACTAMASE
GGAAATGTTG AATACTCATA CTCTTCCTTT TTCAATATTA TTGAAGCATT TATCAGGGTT 9120
ATTGTCTCAT GAGCGGATAC ATATTTGAAT GTATTTAGAA AAATAAACAA ATAGGGGTTC 9180
CGCGCACATT TCCCCGAAAA GTGCCACCT
```

FIG. 3F

```
                                          LEADER
                    -20                        -15                        -10
FRAME 1  Met Asp Phe Gln Val Gln Ile Ile Ser Phe Leu Leu Ile Ser Ala Ser Val
         ATG GAT TTT CAG GTG CAG ATT ATC AGC TTC CTG CTA ATC AGT GCT TCA GTC
                 987         996         1005        1014        1023

-5                    -1 | +1    FR1                              10
Ile Met Ser Arg Gly | Gln Ile Val Leu Ser Gln Ser Pro Ala Ile Leu Ser Ala Ser
ATA ATG TCC AGA GGA |CAA ATT GTT CTC TCC CAG TCT CCA GCA ATC CTG TCT GCA TCT
            1038        1047        1056        1065        1074        1033

20              23 |24     CDR1    27/ 29 30            34
Pro Gly Glu Lys Val Thr Met Thr Cys |Arg Ala Ser Ser Ser Val Ser Tyr Ile His
CCA GGG GAG AAG GTC ACA ATG ACT TGC|AGG GCC AGC TCA AGT GTA AGT TAC ATC CAC
        1095        1104        1113        1122        1131        1140

35     FR2                 40                  45                  49 | 50     CDR2
Trp Phe Gln Gln Lys Pro Gly Ser Ser Pro Lys Pro Trp Ile Tyr |Ala Thr Ser Asn
TGG TTC CAG CAG AAG CCA GGA TCC TCC CCC AAA CCC TGG ATT TAT|GCC ACA TCC AAC
        1152        1161        1170        1179        1188        1197

55  56| 57          60      FR3         65                  70
Leu Ala Ser |Gly Val Pro Val Arg Phe Ser Gly Ser Gly Ser Gly Thr Ser Tyr Ser
CTG GCT TCT|GGA GTC CCT GTT CGC TTC AGT GGC AGT GGG TCT GGG ACT TCT TAC TCT
        1209        1218        1227        1236        1245        1254

75                  80                  85              88 | 89  90
Leu Thr Ile Ser Arg Val Glu Ala Glu Asp Ala Ala Thr Tyr Tyr Cys |Gln Gln Trp
CTC ACC ATC AGC AGA GTG GAG GCT GAA GAT GCT GCC ACT TAT TAC TGC|CAG CAG TGG
        1266        1275        1284        1293        1302        1311

CDR3    95          97 |98      100     FR4         105         107 |
Thr Ser Asn Pro Pro Thr |Phe Gly Gly Gly Thr Lys Leu Glu Ile Lys |
ACT AGT AAC CCA CCC ACG|TTC GGA GGG GGG ACC AAG CTG GAA ATC AAA|
        1323        1332        1341        1350        1359
```

*FIG. 4*

LEADER

```
          -19                    -15                      -10                           -5
FRAME 1   Met Gly Trp Ser Leu Ile Leu Leu Phe Leu Val Ala Val Ala Thr Arg Val
          ATG GGT TGG AGC CTC ATC TTG CTC TTC CTT GTC GCT GTT GCT ACG CGT GTC
                   2409        2418        2427        2436        2445

-1  +1      FR1                                   10                  15
          Leu Ser Gln Val Gln Leu Gln Gln Pro Gly Ala Glu Leu Val Lys Ala Gly Ala Ser
          CTG TCC CAG GTA CAA CTG CAG CAG CCT GGG GCT GAG CTG GTG AAG CCT GGG GCC TCA
                   2460        2469        2478        2487        2496        2505

20                      25                       30  31   CDR1      35  36
          Val Lys Met Ser Cys Lys Ala Ser Gly Tyr Thr Phe Thr Ser Tyr Asn Met His Trp
          GTG AAG ATG TCC TGC AAG GCT TCT GGC TAC ACA TTT ACC AGT TAC AAT ATG CAC TGG
                   2517        2526        2536        2544              2553        2562

40  FR2                          45                   49  50       52 52A 53  54
          Val Lys Gln Thr Pro Gly Arg Gly Leu Glu Trp Ile Gly Ala Ile Tyr Pro Gly Asn
          GTA AAA CAG ACA CCT GGT CGG GGC CTG GAA TGG ATT GGA GCT ATT TAT CCC GGA AAT
                   2574        2583        2592        2601        2610        2619

55             CDR2          60                       65  66   FR3          70
          Gly Asp Thr Ser Tyr Asn Gln Lys Phe Lys Gly Lys Ala Thr Leu Thr Ala Asp Lys
          GGT GAT ACT TCC TAC AAT CAG AAG TTC AAA GGC AAG GCC ACA TTG ACT GCA GAC AAA
                   2631        2640        2649        2658        2667        2676

75                      80      82  82A 82B 82C 83           85
          Ser Ser Ser Thr Ala Tyr Met Gln Leu Ser Ser Leu Thr Ser Glu Asp Ser Ala Val
          TCC TCC AGC ACA GCC TAC ATG CAG CTC AGC AGC CTG ACA TCT GAG GAC TCT GCG GTC
                   2688        2697        2706        2715        2724        2733

90                      94  95      CDR3          100 100A 100B 100C 100D 101  102 103
          Tyr Tyr Cys Ala Arg Ser Thr Tyr Tyr Gly Gly Asp Trp Tyr Phe Asn Val Trp Gly
          TAT TAC TGT GCA AGA TCG ACT TAC TAC GGC GGT GAC TGG TAC TTC AAT GTC TGG GGC
                   2745        2754        2763        2772        2781        2790

105 FR4                  110                 113
          Ala Gly Thr Thr Val Thr Val Ser Ala
          GCA GGG ACC ACG GTC ACC GTC TCT GCA
                   2802        2811        2820
```

*FIG. 5*

THERAPEUTIC APPLICATION OF CHIMERIC AND RADIOLABELED ANTIBODIES TO HUMAN B LYMPHOCYTE RESTRICTED DIFFERENTIATION ANTIGEN FOR TREATMENT OF B CELL LYMPHOMA

This application is a divisional, of application Ser. No. 08/149,099, pending, filed Nov. 3, 1993, which is a continuation-in-part of U.S. Ser. No. 07/978,891, filed Nov. 13, 1992, now abandoned.

37 C.F.R. §1.74(d)/(e) COPYRIGHT NOTICE

A portion of the disclosure of this patent document contains material which is subject to copyright protection. The copyright owner does not object to the reproduction by anyone of the patent document or the patent disclosure, as it appears in the Patent and Trademark Office patent files or records, but otherwise reserves all copyright rights whatsoever.

RELATED APPLICATIONS

This patent document is related to U.S. Ser. No. 07/977,691, now abandoned, entitled "IMPAIRED DOMINANT SELECTABLE MARKER SEQUENCE FOR ENHANCEMENT OF EXPRESSION OF CO-LINKED GENE PRODUCT AND EXPRESSION VECTOR SYSTEMS COMPRISING SAME" having U.S. Ser. No. 07/977,691 (now abandoned; filed Nov. 13, 1992) and "IMPAIRED DOMINANT SELECTABLE MARKER SEQUENCE AND INTRONIC INSERTION STRATEGIES FOR ENHANCEMENT OF EXPRESSION OF GENE PRODUCT AND EXPRESSION VECTOR SYSTEMS COMPRISING SAME," U.S. Ser. No. 08/147,696, now U.S. Pat. No. 5,648,267 (filed simultaneously herewith). The related patent documents are incorporated herein by reference.

FIELD OF THE INVENTION

The references to be discussed throughout this document are set forth merely for the information described therein prior to the filing dates of this document, and nothing herein is to be construed as an admission, either express or implied, that the references are "prior art" or that the inventors are not entitled to antedate such descriptions by virtue of prior inventions or priority based on earlier filed applications.

The present invention is directed to the treatment of B cell lymphoma using chimeric and radiolabeled antibodies to the B cell surface antigen Bp35 ("CD20").

BACKGROUND OF THE INVENTION

The immune system of vertebrates (for example, primates, which include humans, apes, monkeys, etc.) consists of a number of organs and cell types which have evolved to: accurately and specifically recognize foreign microorganisms ("antigen") which invade the vertebrate-host; specifically bind to such foreign microorganisms; and, eliminate/destroy such foreign microorganisms. Lymphocytes, amongst others, are critical to the immune system. Lymphocytes are produced in the thymus, spleen and bone marrow (adult) and represent about 30% of the total white blood cells present in the circulatory system of humans (adult). There are two major sub-populations of lymphocytes: T cells and B cells. T cells are responsible for cell mediated immunity, while B cells are responsible for antibody production (humoral immunity). However, T cells and B cells can be considered as interdependent—in a typical immune response, T cells are activated when the T cell receptor binds to fragments of an antigen that are bound to major histocompatability complex ("MHC") glycoproteins on the surface of an antigen presenting cell; such activation causes release of biological mediators ("interleukins") which, in essence, stimulate B cells to differentiate and produce antibody ("immunoglobulins") against the antigen.

Each B cell within the host expresses A different antibody on its surface-thus, one B cell will express antibody specific for one antigen, while another B cell will express antibody specific for a different antigen. Accordingly, B cells are quite diverse, and this diversity is critical to the immune system. In humans, each B cell can produce an enormous number of antibody molecules (ie, about $10^7$ to $10^8$). Such antibody production most typically ceases (or substantially decreases) when the foreign antigen has been neutralized. Occasionally, however, proliferation of a particular B cell will continue unabated; such proliferation can result in a cancer referred to as "B cell lymphoma."

T cells and B cells both comprise cell surface proteins which can be utilized as "markers" for differentiation and identification. One such human B cell marker is the human B lymphocyte-restricted differentiation antigen Bp35, referred to as "CD20." CD20 is expressed during early pre-B cell development and remains until plasma cell differentiation. Specifically, the CD20 molecule may regulate a step in the activation process which is required for cell cycle initiation and differentiation and is usually expressed at very high levels on neoplastic ("tumor") B cells. CD20, by definition, is present on both "normal" B cells as well as "malignant" B cells, ie, those B cells whose unabated proliferation can lead to B cell lymphoma. Thus, the CD20 surface antigen has the potential of serving as a candidate for "targeting" of B cell lymphomas.

In essence, such targeting can be generalized as follows: antibodies specific to the CD20 surface antigen of B cells are, eg, injected into a patient. These anti-CD20 antibodies specifically bind to the CD20 cell surface antigen of (ostensibly) both normal and malignant B cells; the anti-CD20 antibody bound to the CD20 surface antigen may lead to the destruction and depletion of neoplastic B cells. Additionally, chemical agents or radioactive labels having the potential to destroy the tumor can be conjugated to the anti-CD20 antibody such that the agent is specifically "delivered " to, eg, the neoplastic B cells. Irrespective of the approach, a primary goal is to destroy the tumor: the specific approach can be determined by the particular anti-CD20 antibody which is utilized and, thus, the available approaches to targeting the CD20 antigen can vary considerably.

For example, attempts at such targeting of CD20 surface antigen have been reported. Murine (mouse) monoclonal antibody 1F5 (an anti-CD20 antibody) was reportedly administered by continuous intravenous infusion to B cell lymphoma patients. Extremely high levels (>2 grams) of 1F5 were reportedly required to deplete circulating tumor cells, and the results were described as being "transient." Press et al., "Monoclonal Antibody 1F5 (Anti-CD20) Serotherapy of Human B-Cell Lymphomas." Blood 69/2:584–591 (1987). A potential problem with this approach is that non-human monoclonal antibodies (eg, murine monoclonal antibodies) typically lack human effector functionality, eg, they are unable to, inter alia, mediate complement dependent lysis or lyse human target cells through antibody dependent cellular toxicity or Fc-receptor mediated phagocytosis. Furthermore, non-human monoclonal antibodies can be recognized by the human host as a foreign protein; therefore, repeated injections of such foreign antibodies can lead to the induction of immune responses leading to harmful hypersensitivity reactions. For murine-based monoclonal antibodies, this is often referred to as a Human Anti-Mouse Antibody response, or "HAMA" response. Additionally, these "foreign" antibodies can be attacked by the immune system of the host such that they are, in effect, neutralized before they reach their target site.

Lymphocytes and lymphoma cells are inherently sensitive to radiotherapy for several reasons: the local emission of ionizing radiation of radiolabeled antibodies may kill cells with or without the target antigen (eg, CD20) in close proximity to antibody bound to the antigen; penetrating radiation may obviate the problem of limited access to the antibody in bulky or poorly vascularized tumors; and, the total amount of antibody required may be reduced. The radionuclide emits radioactive particles which can damage cellular DNA to the point where the cellular repair mechanisms are unable to allow the cell to continue living; therefore, if the target cells are tumors, the radioactive label beneficially kills the tumor cells. Radiolabeled antibodies, by definition, include the use of a radioactive substance which may require the need for precautions for both the patient (ie, possible bone marrow transplantation) as well as the health care provider (ie, the need to exercise a high degree of caution when working with the radioactivity).

Therefore, an approach at improving the ability of murine monoclonal antibodies to be effective in the treatment of B-cell disorders has been to conjugate a radioactive label or toxin to the antibody such that the label or toxin is localized at the tumor site. For example, the above-referenced IF5 antibody has been "labeled" with iodine-131 ("$^{131}$I") and was reportedly evaluated for biodistribution in two patients. See Eary, J. F. et al., "Imaging and Treatment of B-Cell Lymphoma" *J. Nuc. Med.* 31/8:1257–1268 (1990); see also, Press, O. W. et al., "Treatment of Refractory Non-Hodgkin's Lymphoma with Radiolabeled MB-1 (Anti-CD37) Antibody" *J. Clin. Onc.* 718:1027–1038 (1989) (indication that one patient treated with $^{131}$I-labeled IF-5 achieved a "partial response"); Goldenberg, D. M. et al., "Targeting, Dosimetry and Radioimmunotherapy of B-Cell Lymphomas with Iodine-131-Labeled LL2 Monoclonal Antibody" *J. Clin. Onc.* 9/4:548–564 (1991) (three of eight patients receiving multiple injections reported to have developed a HAMA response); Appelbaum, F. R. "Radiolabeled Monoclonal Antibodies in the Treatment of Non-Hodgkin's Lymphoma" Hem./Onc. Clinics of N. A. 5/5:1013–1025 (1991) (review article); Press, O. W. et al "Radiolabeled-Antibody Therapy of B-Cell Lymphoma with Autologous Bone Marrow Support." *New England Journal of Medicine* 329/17: 1219–12223 (1993) (iodine-131 labeled anti-CD20 antibody IF5 and B1); and Kaminski, M. G. et al "Radioimmunotherapy of B-Cell Lymphoma with [$^{131}$I] Anti-B1 (Anti-CD20) Antibody". NEJM 329/7 (1993) (iodine-131 labeled anti-CD20 antibody B1; hereinafter "Kaminski").

Toxins (ie chemotherapeutic agents such as doxorubicin or mitomycin C) have also been conjugated to antibodies. See, for example, PCT published application WO 92/07466 (published May 14, 1992).

"Chimeric" antibodies, ie, antibodies which comprise portions from two or more different species (eg, mouse and human) have been developed as an alternative to "conjugated" antibodies. For example, Liu, A. Y. et al., "Production of a Mouse-Human Chimeric Monoclonal Antibody to CD20 with Potent Fc-Dependent Biologic Activity" *J. Immun.* 139 /10:3521–3526 (1987), describes a mouse/human chimeric antibody directed against the CD20 antigen. See also, PCT Publication No. WO 88/04936. However, no information is provided as to the ability, efficacy or practicality of using such chimeric antibodies for the treatment of B cell disorders in the reference. It is noted that in vitro functional assays (eg, complement dependent lysis ("CDC"); antibody dependent cellular cytotoxicity ("ADCC"), etc.) cannot inherently predict the in vivo capability of a chimeric antibody to destroy or deplete target cells expressing the specific antigen. See, for example, Robinson, R. D. et al., "Chimeric mouse-human anti-carcinoma antibodies that mediate different anti-tumor cell biological activities," *Hum. Antibod. Hybridomas* 2:84–93 (1991) (chimeric mouse-human antibody having undetectable ADCC activity). Therefore, the potential therapeutic efficacy of chimeric antibody can only truly be assessed by in vivo experimentation.

What is needed, and what would be a great advance in the art, are therapeutic approaches targeting the CD20 antigen for the treatment of B cell lymphomas in primates, including, but not limited to, humans.

SUMMARY OF THE INVENTION

Disclosed herein are therapeutic methods designed for the treatment of B cell disorders, and in particular, B cell lymphomas. These protocols are based upon the administration of immunologically active chimeric anti-CD20 antibodies for the depletion of peripheral blood B cells, including B cells associated with lymphoma; administration of radiolabeled anti-CD20 antibodies for targeting localized and peripheral B cell associated tumors; and administration of chimeric anti-CD20 antibodies and radiolabeled anti-CD20 antibodies in a cooperative therapeutic strategy.

BRIEF DESCRIPTION OF THE DRAWINGS

FIGS. 2A through 2F are the nucleic acid sequence of the vector of FIG. 1;

FIGS. 3A through 3F are the nucleic acid sequence of the vector of FIG. 1 further comprising murine light and heavy chain variable regions ("anti-CD20 in TCAE 8");

FIG. 4 is the nucleic acid and amino acid sequences (including CDR and framework regions) of murine variable region light chain derived from murine anti-CD20 monoclonal antibody 2B8;

FIG. 5 is the nucleic acid and amino acid sequences (including CDR and framework regions) of murine variable region heavy chain derived from murine anti-CD20 monoclonal antibody 2B8;

DETAILED DESCRIPTION OF PREFERRED EMBODIMENTS

Figure 1:
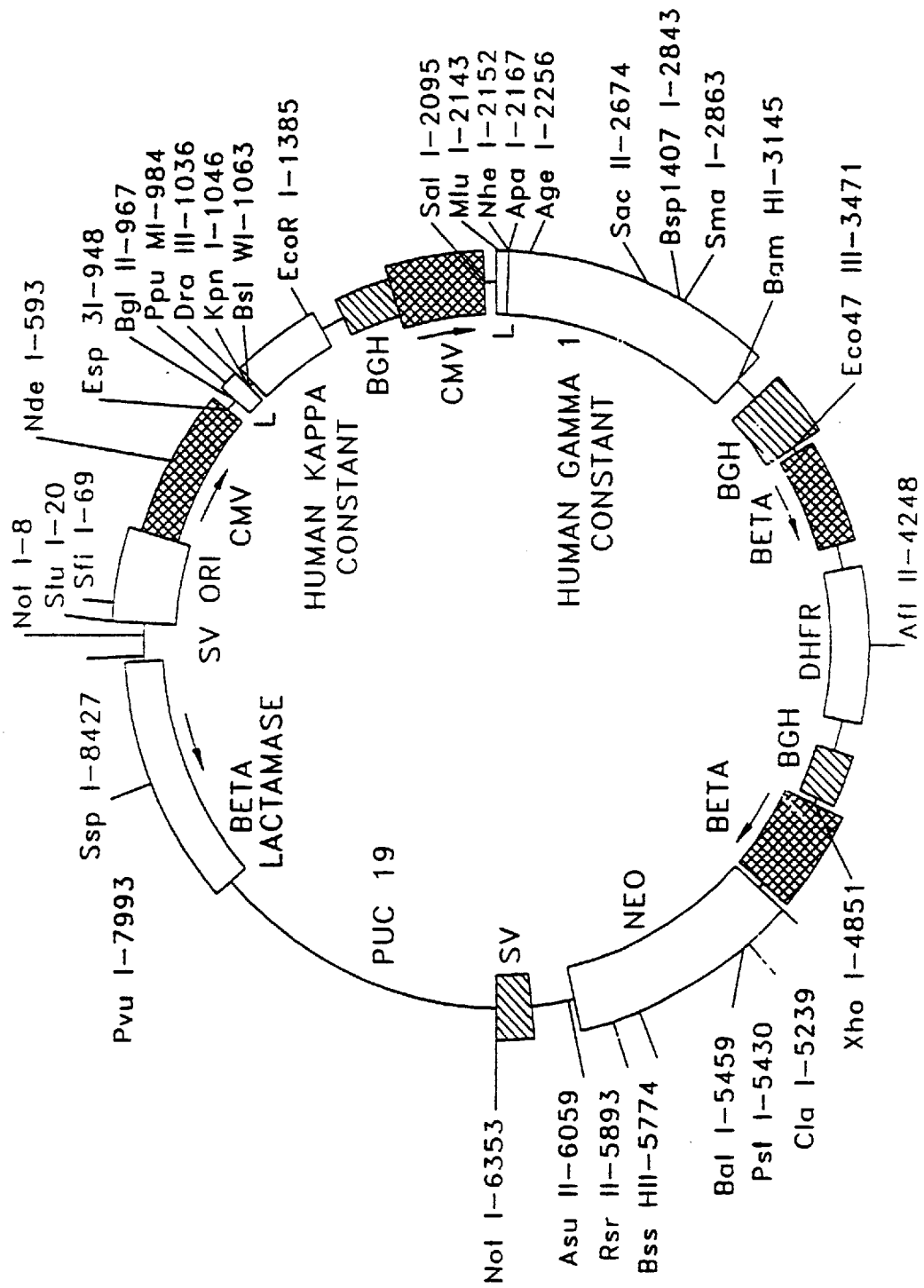
FIG. 1 is a diagrammatic representation of a tandem chimeric antibody expression vector useful in the production of immunologically active chimeric anti-CD20 antibodies ("TCAE 8")

Generally, antibodies are composed of two light chains and two heavy chain molecules; these chains form a general "Y" shape, with both light and heavy chains forming the arms of the Y and the heavy chains forming the base of the Y. Light and heavy chains are divided into domains of structural and functional homology. The variable domains of both the light ("$V_L$") and the heavy ("$V_H$") chains determine recognition and specificity. The constant region domains of light ("$C_L$") and heavy ("$C_H$") chains confer important biological properties, eg antibody chain association, secretion, transplacental mobility, Fc receptor binding complement binding, etc. The series of events leading to immunoglobulin gene expression in the antibody producing cells are complex. The variable domain region gene sequences are located in separate germ line gene segments referred to as "$V_H$," "D," and "$J_H$," or "$V_L$" and "$J_L$." These gene segments are joined by DNA rearrangements to form the complete V regions expressed in heavy and light chains, respectively. The rearranged, joined V segments ($V_L$-$J_L$ and $V_H$-D-$J_H$) then encode the complete variable regions or antigen binding domains of light and heavy chains, respectively.

Serotherapy of human B cell lymphomas using an anti-CD20 murine monoclonal antibody (1F5) has been described by Press et al., (69 *Blood* 584, 1987, supra); the reported therapeutic responses, unfortunately, were transient. Additionally, 25% of the tested patients reportedly developed a human anti-mouse antibody (HAMA) response to the serotherapy. Press et al., suggest that these antibodies, conjugated to toxins or radioisotopes, might afford a more lasting clinical benefit than the unconjugated antibody.

Owing to the debilitating effects of B cell lymphoma and the very real need to provide viable treatment approaches to this disease, we have embarked upon different approaches having a particular antibody, 2B8, as the common link between the approaches. One such approach advantageously exploits the ability of mammalian systems to readily and efficiently recover peripheral blood B cells; using this approach, we seek to, in essence, purge or deplete B cells in peripheral blood and lymphatic tissue as a means of also removing B cell lymphomas. We accomplish this by utilization of, inter alia, immunologically active, chimeric anti-CD20 antibodies. In another approach, we seek to target tumor cells for destruction with radioactive labels.

As used herein, the term "anti-CD20 antibody" is an antibody which specifically recognizes a cell surface non-glycosylated phosphoprotein of 35,000 Daltons, typically designated as the human B lymphocyte restricted differentiation antigen Bp35, commonly referred to as CD20. As used herein, the term "chimeric" when used in reference to anti-CD20 antibodies, encompasses antibodies which are most preferably derived using recombinant deoxyribonucleic acid techniques and which comprise both human (including immunologically "related" species, eg, chimpanzee) and non-human components: the constant region of the chimeric antibody is most preferably substantially identical to the constant region of a natural human antibody; the variable region of the chimeric antibody is most preferably derived from a non-human source and has the desired antigenic and specificity to the CD20 cell surface antigen. The non-human source can be any vertebrate source which can be used to generate antibodies to a human CD20 cell surface antigen or material comprising a human CD20 cell surface antigen. Such non-human source includes, but is not limited to, rodents (eg, rabbit, rat, mouse, etc.) and non-human primates (eg, Old World Monkey, Ape, etc.). Most preferably, the non-human component (variable region) is derived from a murine source. As used herein, the phrase "immunologically active" when used in reference to chimeric anti-CD20 antibodies, means a chimeric antibody which binds human C1q, mediates complement dependent lysis ("CDC") of human B lymphoid cell lines, and lyses human target cells through antibody dependent cellular cytotoxicity ("ADCC"). As used herein, the phrases "indirect labeling" and "indirect labeling approach" both mean that a chelating agent is covalently attached to an antibody and at least one radionuclide is inserted into the chelating agent. Preferred chelating agents and radionuclides are set forth in Srivagtava, S. C. and Mease, R. C.,"Progress in Research on Ligands, Nuclides and Techniques for Labeling Monoclonal Antibodies," *Nucl. Med. Bio.* 18/6: 589–603 (1991) ("Srivagtava") which is incorporated herein by reference. A particularly preferred chelating agent is 1-isothiocycmatobenzyl-3-methyldiothelene triaminepent acetic acid ("MX-DTPA"); particularly preferred radionuclides for indirect labeling include indium [111] and yttrium [90]. As used herein, the phrases "direct labeling" and "direct labeling approach" both mean that a radionuclide is covalently attached directly to an antibody (typically via an amino acid residue). Preferred radionuclides are provided in Srivagtava; a particularly preferred radionuclide for direct labeling is iodine [131] covalently attached via tyrosine residues. The indirect labeling approach is particularly preferred.

The therapeutic approaches disclosed herein are based upon the ability of the immune system of primates to rapidly recover, or rejuvenate, peripheral blood B cells. Additionally, because the principal immune response of primates is occasioned by T cells, when the immune system has a peripheral blood B cell deficiency, the need for "extraordinary" precautions (ie patient isolation, etc.) is not necessary. As a result of these and other nuances of the immune systems of primates, our therapeutic approach to B cell disorders allows for the purging of peripheral blood B cells using immunologically active chimeric anti-CD20 antibodies.

Because peripheral blood B cell disorders, by definition, can indicate a necessity for access to the blood for treatment, the route of administration of the immunologically active chimeric anti-CD20 antibodies and radiolabeled anti-CD20 antibodies is preferably parenteral; as used herein, the term "parenteral" includes intravenous, intramuscular, subcutaneous, rectal, vaginal or intraperitoneal administration. Of these, intravenous administration is most preferred.

The immunologically active chimeric anti-CD20 antibodies and radiolabeled anti-CD20 antibodies will typically be provided by standard technique within a pharmaceutically acceptable buffer, for example, sterile saline, sterile buffered water, propylene glycol, combinations of the foregoing, etc. Methods for preparing parenterally administrable agents are described in *Pharmaceutical Carriers & Formulations*, Martin, Remington's Pharmaceutical Sciences, 15th Ed. (Mack Pub. Co., Easton, Pa. 1975), which is incorporated herein by reference.

The specific, therapeutically effective amount of immunologically active chimeric anti-CD20 antibodies useful to produce a unique therapeutic effect in any given patient can be determined by standard techniques well known to those of ordinary skill in the art.

Effective dosages (ie, therapeutically effective amounts) of the immunologically active chimeric anti-CD20 antibodies range from about 0.001 to about 30 mg/kg body weight, more preferably from about 0.01 to about 25 mg/kg body weight, and most preferably from about 0.4 to about 20.0 mg/kg body weight. Other dosages are viable; factors influencing dosage include, but are not limited to, the severity of the disease; previous treatment approaches; overall health of the patient; other diseases present, etc. The skilled artisan is readily credited with assessing a particular patient and determining a suitable dosage that falls within the ranges, or if necessary, outside of the ranges.

Introduction of the immunologically active chimeric anti-CD20 antibodies in these dose ranges can be carried out as a single treatment or over a series of treatments. With respect to chimeric antibodies, it is preferred that such introduction be carried out over a series of treatments; this preferred approach is predicated upon the treatment methodology associated with this disease. While not wishing to be bound by any particular theory, because the immunologically active chimeric anti-CD20 antibodies are both immunologically active and bind to CD20, upon initial introduction of the immunologically active chimeric anti-CD20 antibodies to the individual, peripheral blood B cell depletion will begin; we have observed a nearly complete depletion within about 24 hours post treatment infusion. Because of this, subsequent introduction(s) of the immunologically active chimeric anti-CD20 antibodies (or radiolabeled anti-CD20 antibodies) to the patient is presumed to: a) clear remaining peripheral blood B cells; b) begin B cell depletion from lymph nodes; c) begin B cell depletion from other tissue sources, eg, bone marrow, tumor, etc. Stated again, by using repeated introductions of the immunologically active chimeric anti-CD20 antibodies, a series of events take place, each event being viewed by us as important to effective treatment of the disease. The first "event" then, can be viewed as principally directed to substantially depleting the patient's peripheral blood B cells; the subsequent "events" can be viewed as either principally directed to simultaneously or serially clearing remaining B cells from the system clearing lymph node B cells, or clearing other tissue B cells.

In effect, while a single dosage provides benefits and can be effectively utilized for disease treatment/management, a preferred treatment course can occur over several stages; most preferably, between about 0.4 and about 20 mg/kg body weight of the immunologically active chimeric anti-CD20 antibodies is introduced to the patient once a week for between about 2 to 10 weeks, most preferably for about 4 weeks.

With reference to the use of radiolabeled anti-CD20 antibodies, a preference is that the antibody is non-chimeric; this preference is predicated upon the significantly longer circulating half-life of chimeric antibodies vis-a-vis murine antibodies (ie, with a longer circulating half-life, the radionuclide is present in the patient for extended periods). However, radiolabeled chimeric antibodies can be beneficially utilized with lower milli-Curries ("mCi") dosages used in conjunction with the chimeric antibody relative to the murine antibody. This scenario allows for a decrease in bone marrow toxicity to an acceptable level, while maintaining therapeutic utility.

A variety of radionuclides are applicable to the present invention and those skilled in the art are credited with the ability to readily determine which radionuclide is most appropriate under a variety of circumstances. For example, iodine [131] is a well known radionuclide used for targeted immunotherapy. However, the clinical usefulness of iodine [131] can be limited by several factors including: eight-day physical half-life; dehalogenation of iodinated antibody both in the blood and at tumor sites; and emission characteristics (eg, large gamma component) which can be suboptimal for localized dose deposition in tumor. With the advent of superior chelating agents, the opportunity for attaching metal chelating groups to proteins has increased the opportunities to utilize other radionuclides such as indium [131] and yttrium [90]. Yttrium [90] provides several benefits for utilization in radioimmunotherapeutic applications: the 64 hour half-life of yttrium [90] is long enough to allow antibody accumulation by tumor and, unlike eg, iodine [131], yttrium [90] is a pure beta emitter of high energy with no accompanying gamma irradiation in its decay, with a range in tissue of 100 to 1000 cell diameters. Furthermore, the minimal amount of penetrating radiation allows for outpatient administration of yttrium [90]-labeled antibodies. Additionally, interalization of labeled antibody is not required for cell killing, and the local emission of ionizing radiation should be lethal for adjacent tumor cells lacking the target antigen.

One non-therapeutic limitation to yttrium [90] is based upon the absence of significant gamma radiation making imaging therewith difficult. To avoid this problem, a diagnostic "imaging" radionuclide, such as indium [111], can be utilized for determining the location and relative size of a tumor prior to the administration of therapeutic does of yttrium [90]-labeled anti-CD20. Indium [111] is particularly preferred as the diagnostic radionuclide because: between about 1 to about 10 mCi can be safely administered without detectable toxicity; and the imaging data is generally predictive of subsequent yttrium [90]-labeled antibody distribution. Most imaging studies utilize 5 mCi indium [111]-labeled antibody because this dose is both safe and has increased imaging efficiency compared with lower doses, with optimal imaging occurring at three to six days after antibody administration. See, for example, Murray J. L., 26 *J. Nuc. Med.* 3328 (1985) and Carraguillo, J. A. et al, 26 *J. Nuc. Med.* 67 (1985).

Effective single treatment dosages (ie, therapeutically effective amounts) of yttrium [90] labeled anti-CD20 antibodies range from between about 5 and about 75 mCi, more preferably between about 10 and about 40 mCi. Effective single treatment non-marrow ablative dosages of iodine [131] labeled anti-CD20 antibodies range from between about 5 and about 70 mCi, more preferably between about 5 and about 40 mCi. Effective single treatment ablative dosages (ie, may require autologous bone marrow transplantation) of iodine [131] labeled anti-CD20 antibodies range from between about 30 and about 600 mCi, more preferably between about 50 and less than about 500 mCi. In conjunction with a chimeric anti-CD20 antibody, owing to the longer circulating half life vis-a-vis murine antibodies, an effective single treatment non-marrow ablative dosages of iodine [131] labeled chimeric anti-CD20 antibodies range from between about 5 and about 40 mCi, more preferably less than about 30 mCi. Imaging criteria for, eg, the indium [111] label, are typically less than about 5 mCi.

With respect to radiolabeled anti-CD20 antibodies, therapy therewith can also occur using a single therapy treatment or using multiple treatments. Because of the radionuclide component, it is preferred that prior to treatment, peripheral stem cells ("PSC") or bone marrow ("BM") be "harvested" for patients experiencing potentially fatal bone marrow toxicity resulting from radiation. BM and/or PSC are harvested using standard techniques, and then purged and frozen for possible reinfusion. Additionally, it is most preferred that prior to treatment a diagnostic dosimetry study using a diagnostic labeled antibody (eg, using indium [111]) be conducted on the patient, a purpose of which is to ensure that the therapeutically labeled antibody (eg, using yttrium [90]) will not become unnecessarily "concentrated" in any normal organ or tissue.

Chimeric mouse/human antibodies have been described. See, for example, Morrison, S. L. et al., *PNAS* I1:6851–6854 (November 1984); European Patent Publication No. 172494; Boulianne, G. L. at al., *Nature* 312:642 (December 1984); Neubeiger, M. S. et al., *Nature* 314:268 (March 1985); European Patent Publication No. 125023; Tan et al., *J. Immunol.* 135:8564 (November 1985); Sun, L. K. et al., *Hybridoma* 5/1:517 (1986); Sahagan et al., *J. Immunol.* 137:1066–1074 (1986). See generally, Muron, *Nature* 312:597 (December 1984); Dickson, *Genetic Engineering News* 5/3 (March 1985); Marx, *Science* 229 455 (August 1985); and Morrison *Science* 229:1202–1207 (September 1985). Robinson et al., in PCT Publication Number WO 88/04936, describe a chimeric antibody with human constant region and murine variable region, having specificity to an epitope of CD20; the murine portion of the chimeric antibody of the Robinson references is derived from the 2H7 mouse monoclonal antibody (gamma 2b, kappa). While the reference notes that the described chimeric antibody is a "prime candidate" for the treatment of B cell disorders, this statement can be viewed as no more than a suggestion to those in the art to determine whether or not this suggestion is accurate for this particular antibody, particularly because the reference lacks any data to support an assertion of therapeutic effectiveness, and importantly, data using higher order mammals such as primates or humans.

Methodologies for generating chimeric antibodies are available to those in the art. For example, the light and heavy chains can be expressed separately, using, for example, immunoglobulin light chain and immunoglobulin heavy chains in separate plasmids. These can then be purified and assembled in vitro into complete antibodies; methodologies for accomplishing such assembly have been described. See, for example, Scharff, M., *Harvey Lectures* 69:125 (1974). In vitro reaction parameters for the formation of IgG antibodies from reduced isolated light and heavy chains have also been described. See, for example, Beychok, S., *Cells of Immunoglobulin Synthesis*, Academic Press, New York, p. 69, 1979. Co-expression of light and heavy chains in the same cells to achieve intracellular association and linkage of heavy and light chains into complete $H_2L_2$ IgG antibodies is also possible. Such co-expression can be accomplished using either the same or different plasmids in the same host cell.

Another approach, and one which is our most preferred approach for developing a chimeric non-human/human anti-CD20 antibody, is based upon utilization of an expression vector which includes, ab initio, DNA encoding heavy and light chain constant regions from a human source. Such a vector allows for inserting DNA encoding non-human variable region such that a variety of non-human anti-CD20 antibodies can be generated, screened and analyzed for various characteristics (eg, type of binding specificity, epitope binding regions, etc.); thereafter, cDNA encoding the light and heavy chain variable regions from a preferred or desired anti-CD20 antibody can be incorporated into the vector. We refer to these types of vectors as Tandem Chimeric Antibody Expression ("TCAE") vectors. A most preferred TCAE vector which was used to generate immunologically active chimeric anti-CD20 antibodies for therapeutic treatment of lymphomas is TCAE 8. TCAE 8 is a derivative of a vector owned by the assignee of this patent document, referred to as TCAE 5.2 the difference being that in TCAE 5.2, the translation initiation start site of the dominant selectable marker (neomycin phosphostransferase, "NEO") is a consensus Kozak sequence, while for TCAE 8, this region is a partially impaired consensus Kozak sequence. Details regarding the impact of the initiation start site of the dominant selectable marker of the TCAE vectors (also referred to as "ANEX vector") vis-a-vis protein expression are disclosed in detail in the co-pending application filed herewith. TCAE 8 comprises four (4) transcriptional cassettes, and these are in tandem order, ie, a human immunoglobulin light chain absent a variable region; a human immunoglobulin heavy chain absent a variable region; DHFR; and NEO. Each transcriptional cassette contains its own eukaryotic promoter and polyadenylation region (reference is made to FIG. 1 which is a diagrammatic representation of the TCAE 8 vector). Specifically:

1) the CMV promoter/enhancer in front of the immunoglobulin heavy chain is a truncated version of the promoter/enhancer in front of the light chain, from the Nhe I site at −350 to the Sst I site at −16 (see, 41 *Cell* 521, 1985).

2) a human immunoglobulin light chain constant region was derived via amplification of cDNA by a PCR reaction. In TCAE 8, this was the human immunoglobulin light chain kappa constant region (Kabat numbering, amino acids 108–214, allotype Km 3, (see, Kabat, E. A. "Sequences of proteins of immunological interest," NIH Publication, Fifth Ed. No. 91–3242, 1991)), and the human immunoglobulin heavy chain gamma 1 constant region (Kabat numbering amino acids 114–478, allotype Gm1a, Gm1z). The light chain was isolated from normal human blood (IDEC Pharmaceuticals Corporation, La Jolla, Calif.); RNA therefrom was used to synthesize cDNA which was then amplified using PCR techniques (primers were derived vis-a-vis the consensus from Kabat). The heavy chain was isolated (using PCR techniques) from cDNA prepared from RNA which was in turn derived from cells transfected with a human IgG1 vector (see, 3 Prot. Eng 531, 1990; vector $pN_{\gamma 1}62$). Two amino acids were changed in the isolated human IgG1 to match the consensus amino acid sequence from Kabat, to wit: amino acid 225 was changed from valine to alanine (GTT to GCA), and amino acid 287 was changed from methionine to lysine (ATG to AAG);

3) The human immunoglobulin light and heavy chain cassettes contain synthetic signal sequences for secretion of the immunoglobulin chains;

4) The human immunoglobulin light and heavy chain cassettes contain specific DNA restriction sites which allow for insertion of light and heavy immunoglobulin variable regions which maintain the transitional reading frame and do not alter the amino acids normally found in immunoglobulin chains;

5) The DHFR cassette contained its own eukaryotic promoter (mouse beta globin major promoter, "BETA") and polyadenylation region (bovine growth hormone polyadenylation, "BGH"); and 6) The NEO cassette contained its own eukaryotic promoter (BETA) and polyadenylation region (SV40 early polyadenylation, "SV").

With respect to the TCAE 8 vector and the NEO cassette, the Kozak region was a partially impaired consensus Kozak sequence (which included an upstream Cla I site):

```
        ClaI      -3    +1
GGGAGCTTGG ATCGAT ccTct ATG Gtt SEQ. ID NO. 1
```

(In the TCAE 5.2 vector, the change is between the Cla I and ATG regions, to wit: ccAcc.)

The complete sequence listing of TCAE 8 (including the specific components of the four transcriptional cassettes) is set forth in FIG. 2 (SEQ. ID. NO. 1).

As will be appreciated by those in the art, the TCAE vectors beneficially allow for substantially reducing the time in generating the immunologically active chimeric anti-CD20 antibodies. Generation and isolation of non-human light and heavy chain variable regions, followed by incorporation thereof within the human light chain constant transcriptional cassette and human heavy chain constant transcriptional cassette, allows for production of immunologically active chimeric anti-CD20 antibodies.

We have derived a most preferred non-human variable region with specificity to the CD20 antigen using a murine source and hybridoma technology. Using polymerase chain reaction ("PCR") techniques, the murine light and heavy variable regions were cloned directly into the TCAE 8 vector—this is the most preferred route for incorporation of the non-human variable region into the TCAE vector. This preference is principally predicated upon the efficiency of the PCR reaction and the accuracy of insertion. However, other equivalent procedures for accomplishing this task are available. For example, using TCAE 8 (or an equivalent vector), the sequence of the variable region of a non-human anti-CD20 antibody can be obtained, followed by oligonucleotide synthesis of portions of the sequence or, if appropriate, the entire sequence; thereafter, the portions or the entire synthetic sequence can be inserted into the appropriate locations within the vector. Those skilled in the art are credited with the ability to accomplish this task.

Our most preferred immunologically active chimeric anti-CD20 antibodies were derived from utilization of TCAE 8 vector which included murine variable regions derived from monoclonal antibody to CD20; this antibody (to be discussed in detail, infra), is referred to as "2B8." The complete sequence of the variable regions obtained from 2B8 in TCAE 8 ("anti-CD20 in TCAE 8") is set forth in FIG. 3 (SEQ. ID. NO. 2).

The host cell line utilized for protein expression is most preferably of mammalian origin; those skilled in the art are credited with ability to preferentially determine particular host cell lines which are best suited for the desired gene product to be expressed therein, Exemplary host cell lines include, but are not limited to, DG44 and DUXBll (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/0 (mouse myeloma), P3x63-Ag3.653 (mouse myeloma), BFA-lclBPT (bovine endothelial cells), RAJI (human lymphocyte) and 293 (human kidney). Host cell lines are typically available from commercial services, the American Tissue Culture Collection or from published literature.

Preferably the host cell line is either DG44 ("CHO") or SP2/0. See Urland, G. et al., "Effect of gamma rays and the dihydrofolate reductase locus: deletions and inversions." *Som. Cell & Mol. Gen.* 12/6:555–566 (1986), and Shulman, M. et al., "A better cell line for making hybridomas secreting specific antibodies." *Nature* 276:269 (1978), respectively. Most preferably, the host cell line is DG44. Transfection of the plasmid into the host cell can be accomplished by any technique available to those in the art. These include, but are not limited to, transfection (including electrophoresis and electroporation), cell fusion with enveloped DNA, microinjection, and infection with intact virus. See, Ridgway, A. A. G. "Mammalian Expression Vectors." Chapter 24.2, pp. 470–472 *Vectors*, Rodriguez and Denhardt, Eds. (Butterworths, Boston, Mass. 1988). Most preferably, plasmid introduction into the host is via electroporation.

EXAMPLES

The following examples are not intended, nor are they to be construed, as limiting the invention. The examples are intended to evidence; dose-imaging using a radiolabeled anti-CD20 antibody ("I2B8"); radiolabeled anti-CD20 antibody ("Y2B8"); and immunologically active, chimeric anti-CD20 antibody ("C2B8") derived utilizing a specific vector ("TCAE 8") and variable regions derived from murine anti-CD20 monoclonal antibody ("2B8").

I. RADIOLABELED ANTI-CD20 ANTIBODY 2B8

A. Anti-CD20 Monoclonal Antibody (Murine) Production ("2B8")

BALB/C mice were repeatedly immunized with the human lymphoblastoid cell line SB (see, Adams, R. A. et al., "Direct implantation and serial transplantation of human acute lymphoblastic leukemia in hamsters, SB-2." *Can Res* 28:1121–1125 (1968); this cell line is available from the American Tissue Culture Collection, Rockville, Md., under ATCC accession number ATCC CCL 120), with weekly injections over a period of 3–4 months. Mice evidencing high serum titers of anti-CD20 antibodies, as determined by inhibition of known CD20-specific antibodies (anti-CD20 antibodies utilized were Leu 16, Beckton Dickinson, San Jose, Calif, Cat. No. 7670; and Bl, Coulter Corp., Hialeah, Fla., Cat. No. 6602201) were identified; the spleens of such mice were then removed. Spleen cells were fused with the mouse myeloma SP2/0 in accordance with the protocol described in Einfeld, D. A. et al., (1988) EMBO 7:711 (SP2/0 has ATCC accession no. ATCC CRL 8006).

Assays for CD20 specificity were accomplished by radioimmunoassay. Briefly, purified anti-CD20 Bl was radiolabeled with $I^{125}$ by the iodobead method as described in Valentine, M. A. et al., (1989) *J. Biol. Chem.* 264:11282. ($I^{125}$ Sodium Iodide, ICN, Irvine, Calif., Cat. No. 28665H). Hybridomas were screened by co-incubation of 0.05 ml of media from each of the fusion wells together with 0.05 ml of $I^{125}$ labeled anti-CD20 Bl (10 ng) in 1% BSA, PBS (pH 7.4), and 0.5 ml of the same buffer containing 100,000 SB cells. After incubation for 1 hr at room temperature, the cells were harvested by transferring to 96 well titer plates (V&P Scientific, San Diego, Calif.), and washed thoroughly. Duplicate wells containing unlabeled anti-CD20 Bl and wells containing no inhibiting antibody were used as positive and negative controls, respectively. Wells containing greater than 50% inhibition were expanded and cloned. The antibody demonstrating the highest inhibition was derived from the cloned cell line designated herein as "2B8."

B. Preparation of 2B8-MX-DTPA Conjugate i. MX-DTPA

Carbon-14-labeled 1-isothiocyanatobenzyl-3-methyldiethylene triaminepentaacetic acid ("carbon-14 labeled MX-DTPA") was used as a chelating agent for conjugation of radiolabel to 2B8. Manipulations of MX-DTPA were conducted to maintain metal-free conditions, ie, metal-free reagents were utilized and, when possible, polypropylene plastic containers (flasks, beakers, graduated cylinders, pipette tips) washed with ALCONOX® (a detergent) and rinsed with MILLI-Q® water (purified water), were similarly utilized. MX-DTPA was obtained as a dry solid from Dr. Otto Gansow (National Institute of Health, Bethesda, Md.) and stored desiccated at 4° C. (protected from light), with stock solutions being prepared in Milli-Q® water at a concentration of 2–5 mM, with storage at −70° C. MX-DTPA was also obtained from Coulter Immunology (Hialeah, Fla.) as the disodium salt in water and stored at −70° C.

ii. Preparation of 2B8

Purified 2B8 was prepared for conjugation with MX-DTPA by transferring the antibody into metal-free 50 mM bicine-NaOff, pH 8.6, containing 150 mM NaCl, using repetitive buffer exchange with CENTRICON 30™ spin filters (30,000D, MWCO; Amicon). Generally, 50–200 μL of protein (10 mg/nl) was added to the filter unit, followed by 2 mL of bicine buffer. The filter was centrifuged at 4° C. in a Sorval SS-34 rotor (6,000 rpm, 45 min.). Retentate volume was approximately 50–100 μL; this process was repeated twice using the same filter. Retentate was transferred to a polypropylene 1.5 mL screw cap tube, assayed for protein, diluted to 10.0 mg/mL and stored at 4° C. until utilized; protein was similarly transferred into 50 mM sodium citrate, pH 5.5, containing 150 mM NaCl and 0.05% sodium azide, using the foregoing protocol.

iii. Conjugation of 2B8 with MX-DTPA

Conjugation of 2B8 with MX-DTPA was performed in polypropylene tubes at ambient temperature. Frozen MX-DTPA stock solutions were thawed immediately prior to use. 50–200 mL of protein at 10 mg/mL were reacted with MX-DTPA at a molar ratio of MX-DTPA-to-2B8 of 4:1. Reactions were initiated by adding the MX-DTPA stock solution and gently mixing; the conjugation was allowed to proceed overnight (14 to 20 hr), at ambient temperature. Unreacted MX-DTPA was removed from the conjugate by dialysis or repetitive ultrafiltration, as described above in Example I.B.ii, into metal-free normal saline (0.9% w/v) containing 0.05% sodium azide. The protein concentration was adjusted to 10 mg/mL and stored at 4° C. in a polypropylene tube until radiolabeled.

iv. Determination of MX-DTPA Incorporation

MX-DTPA incorporation was determined by scintillation counting and comparing the value obtained with the purified conjugate to the specific activity of the carbon-[14]-labeled MX-DTPA. For certain studies, in which non-radioactive MX-DTPA (Coulter Immunology) was utilized, MX-DTPA incorporation was assessed by incubating the conjugate with an excess of a radioactive carrier solution of yttrium-[90] of known concentration and specific activity.

A stock solution of yttrium chloride of known concentration was prepared in metal-free 0.05N HCl to which carrier-free yttrium-[90] (chloride salt) was added. An aliquot of this solution was analyzed by liquid scintillation counting to determine an accurate specific activity for this reagent. A volume of the yttrium chloride reagent equal to 3-times the number of mols of chelate expected to be attached to the antibody, (typically 2 mol/mol antibody), was added to a polypropylene tube, and the pH adjusted to 4.0–4.5 with 2M sodium acetate. Conjugated antibody was subsequently added and the mixture incubated 15–30 min. at ambient temperature. The reaction was quenched by adding 20 mM EDTA to a final concentration of 1 mM and the pH of the solution adjusted to approximately pH 6 with 2M sodium acetate.

After a 5 min. incubation, the entire volume was purified by high-performance, size-exclusion chromatography (described infra). The eluted protein-containing fractions were combined, the protein concentration determined, and an aliquot assayed for radioactivity. The chelate incorporation was calculated using the specific activity of the yttrium-[90] chloride preparation and the protein concentration.

v. Immunoreactivity of 2B8-MX-DTPA

The immunoreactivity of conjugated 2B8 was assessed using whole-cell ELISA. Mid-log phase SB cells were harvested from culture by centrifugation and washed two times with 1X HBSS. Cells were diluted to 1–2×10$^6$ cells/mL in HBSS and aliquoted into 96-well polystyrene microtiter plates at 50,000–100,000 cells/well. The plates were dried under vacuum for 2 h. at 40°–45° C. to fix the cells to the plastic; plates were stored dry at −20° C. until utilized. For assay, the plates were warmed to ambient temperature immediately before use, then blocked with 1× PBS, pH 7.2–7.4 containing 1% BSA (2 h). Samples for assay were diluted in 1× PBS/1% BSA, applied to plates and serially diluted (1:2) into the same buffer. After incubating plates for 1 h. at ambient temperature, the plates were washed three times with 1× PBS. Secondary antibody (goat anti-mouse IgG1-specific HRP conjugate 50 μL) was added to wells (1:1500 dilution in 1× PBS/1% BSA) and incubated 1 h. at ambient temperature. Plates were washed four times with 1× PBS followed by the addition of ABTS substrate solution (50 mM sodium citrate, pH 4.5 containing 0.01% ATBS and 0.001% H202). Plates were read at 405 nm after 15–30 min. incubation. Antigen-negative HSB cells were included in assays to monitor non-specific binding. Immunoreactivity of the conjugate was calculated by plotting the absorbance values vs. the respective dilution factor and comparing these to values obtained using native antibody (representing 100% immunoreactivity) tested on the same plate; several values on the linear portion of the titration profile were compared and a mean value determined (data not shown).

vi. Preparation of Indium-[111]-Labeled 2B8-MX-DTPA ("I2B8")

Conjugates were radiolabeled with carrier-free indium-[111]. An aliquot of isotope (0.1–2 mCi/mg antibody) in 0.05M HCL was transferred to a polypropylene tube and approximately one-tenth volume of metal-free 2M HCl added. After incubation for 5 min., metal-free 2M sodium acetate was added to adjust the solution to pH 4.0–4.4. Approximately 0.5 mg of 2B8-MX-DTPA was added from a stock solution of 10.0 mg/mL DTPA in normal saline, or 50 mM sodium citrate/150 mM NaCl containing 0.05% sodium azide, and the solution gently mixed immediately. The pH solution was checked with pH paper to verify a value of 4.0–4.5 and the mixture incubated at ambient temperature for 15–30 min. Subsequently, the reaction was quenched by adding 20 mM EDTA to a final concentration of 1 mM and the reaction mixture was adjusted to approximately pH 6.0 using 2M sodium acetate.

After a 5–10 min. incubation, uncomplexed radioisotope was removed by size-exclusion chromatography. The HPLC unit consisted of Waters Model 6000 or TosoHaas Model TSK-6110 solvent delivery system fitted, respectively, with a Waters U6K or Rheodyne 700 injection valve. Chromatographic separations were performed using a gel permeation column (BioRad SEC-250; 7.5×300 mm or comparable TosoHaas column) and a SEC-250 guard column (7.5×100 mm). The system was equipped with a fraction collector (Pharmacia Frac200) and a UV monitor fitted with a 280 nm filter (Pharmacia model UV-1). Samples were applied and eluted isocratically using 1× PBS, pH 7.4, at 1.0 mL/min flow rate. One-half milliliter fractions were collected in glass tubes and aliquots of these counted in a gamma counter. The lower and upper windows were set to 100 and 500 KeV respectively.

The radioincorporation was calculated by summing the radioactivity associated with the eluted protein peak and dividing this number by the total radioactivity eluted from the column; this value was then expressed as a percentage (data not shown). In some cases, the radioincorporation was determined using instant thin-layer chromatography ("ITLC"). Radiolabeled conjugate was diluted 1:10 or 1:20 in 1× PBS containing or 1× PBS/1 mM DTPA, then 1 $\mu$L was spotted 1.5 cm from one end of a 1×5 cm strip of ITLC SG paper. The paper was developed by ascending chromatography using 10% ammonium acetate in methanol:water (1:1;v/v). The strip was dried, cut in half crosswise, and the radioactivity associated with each section determined by gamma counting. The radioactivity associated with the bottom half of the strip (protein-associated radioactivity) was expressed as a percentage of the total radioactivity, determined by summing the values for both top and bottom halves (data not shown).

Specific activities were determined by measuring the radioactivity of an appropriate aliquot of the radiolabeled conjugate. This value was corrected for the counter efficiency (typically 75%) and related to the protein concentration of the conjugate, previously determined by absorbance at 280 nm, and the resulting value expressed as mCi/mg protein.

For some experiments, 2B8-MX-DTPA was radiolabeled with indium [111] following a protocol similar to the one described above but without purification by HPLC; this was referred to as the "mix-and-shoot" protocol.

vii. Preparation of Yttrium-[90]-Labeled 2B8-M-DTPA ("Y2B8")

The same protocol described for the preparation of I2B8 was followed for the preparation of the yttrium-[90]-labeled 2B8-MX-DTPA ("Y2B8") conjugate except that 2 ng HCl was not utilized; all preparations of yttrium-labeled conjugates were purified by size-exclusion chromatography as described above.

C. Non-Human Animal Studies.

i. Biodistribution of Radiolabeled 2B8-MX-DTPA

I2B8 was evaluated for tissue biodistribution in six-to-eight week old BALB/c mice. The radiolabeled conjugate was prepared using clinical-grade 2B8-MX-DTPA following the "mix and shoot" protocol described above. The specific activity of the conjugate was 2.3 mCi/mg and the conjugate was formulated in PBS, pH 7.4 containing 50 mg/mL HSA. Mice were injected intravenously with 100 $\mu$L of I2B8 (approximately 21$\mu$ Ci) and groups of three mice were sacrificed by cervical dislocation at 0, 24, 48, and 72 hours. After sacrifice, the tail, heart, lungs, liver, kidney, spleen, muscle, and femur were removed, washed and weighed; a sample of blood was also removed for analysis. Radioactivity associated with each specimen was determined by gamma counting and the percent injected dose par gram tissue subsequently determined. No attempt was made to discount the activity contribution represented by the blood associated with individual organs.

In a separate protocol, aliquots of 2B8-MX-DTPA incubated at 4° C. and 30° C. for 10 weeks were radiolabeled with indium-[111] to a specific activity of 2.1 mCi/mg for both preparations. These conjugates were then used in biodistribution studies in mice as described above.

For dosimetry determinations, 2B8-MX-DTPA was radiolabeled with indium-[111] to a specific activity of 2.3 mCi/mg and approximately 1.1$\mu$ Ci was injected into each of 20 BALB/c mice. Subsequently, groups of five mice each were sacrificed at 1, 24, 48 and 72 hours and their organs removed and prepared for analysis. In addition, portions of the skin, muscle and bone were removed and processed for analysis; the urine and feces were also collected and analyzed for the 24–72 hour time points.

Using a similar approach, 2B8-MX-DTPA was also radiolabeled with yttrium-[90] and its biological distribution evaluated in BALB/c mice over a 72-hour time period. Following purification by HPLC size exclusion chromatography, four groups of five mice each were injected intravenously with approximately 1$\mu$ Ci of clinically-formulated conjugate (specific activity:12.2 mCi/mg); groups were subsequently sacrificed at 1, 24, 48 and 72 hours and their organs and tissues analyzed as described above. Radioactivity associated with each tissue specimen was determined by measuring bremstrahlung energy with a gamma scintillation counter. Activity values were subsequently expressed as percent injected dose per gram tissue or percent injected dose per organ. While organs and other tissues were rinsed repeatedly to remove superficial blood, the organs were not perfused. Thus, organ activity values were not discounted for the activity contribution represented by internally associated blood.

ii. Tumor Localization of I2B8

The localization of radiolabeled 2B8-MX-DTPA was determined in athymic mice bearing Ramos B cell tumors. Six-to-eight week old athymic mice were injected subcutaneously (left-rear flank) with 0.1 mL of RPMI-1640 containing 1.2×10$^7$ Ramos tumor cells which had been previously adapted for growth in athymic mice. Tumors arose within two weeks and ranged in weight from 0.07 to 1.1 grams. Mice were injected intravenously with 100 $\mu$L of indium-[111]-labeled 2B8-MX-DTPA (16.7$\mu$ Ci) and groups of three mice were sacrificed by cervical dislocation at 0, 24, 48, and 72 hours. After sacrifice the tail, heart, lungs, liver, kidney, spleen, muscle, femur, and tumor were removed, washed, weighed; a sample of blood was also removed for analysis. Radioactivity associated with each specimen was determined by gamma counting and the percent injected dose per gram tissue determined.

iii. Biodistribution and Tumor Localization Studies with Radiolabeled 2B8-MX-DTPA Following the preliminary biodistribution experiment described above (Example I.B.viii.a.), conjugated 2B8 was radiolabeled with indium-[111] to a specific activity of 2.3 mCi/mg and roughly 1.1$\mu$ Ci was injected into each of twenty BALB/c mice to determine biodistribution of the radiolabeled material. Subsequentially, groups of five mice each were sacrificed at 1, 24, 48 and 72 hours and their organs and a portion of the skin, muscle and bone were removed and processed for analysis. In addition, the urine and feces were collected and analyzed for the 24–72 hour time-points. The level of radioactivity in the blood dropped from 40.3% of the injected dose per gram at 1 hour to 18.9% at 72 hours (data not shown). Values for the heart, kidney, muscle and spleen remained in the range of 0.7–9.8% throughout the experiment. Levels of radioactivity found in the lungs decreased from 14.2% at 1 hour to 7.6% at 72 hours; similarly the respective liver injected-dose per gram values were 10.3% and 9.9%. These data were used in determining radiation absorbed dose estimates I2B8 described below.

The biodistribution of yttrium-[90]-labeled conjugate, having a specific activity of 12.2 mCi/mg antibody, was evaluated in BALB/c mice. Radioincorporations of >90% were obtained and the radiolabeled antibody was purified by HPLC. Tissue deposition of radioactivity was evaluated in the major organs, and the skin, muscle, bone, and urine and feces over 72 hours and expressed as percent injected dose/g tissue. Results (not shown) evidenced that while the levels of radioactivity associated with the blood dropped from approximately 39.2% injected dose per gram at 1 hour to roughly 15.4% after 72 hours the levels of radioactivity associated with tail, heart, kidney, muscle and spleen remained fairly constant at 10.2% or less throughout the course of the experiment. Importantly, the radioactivity associated with the bone ranged from 4.4% of the injected dose per gram bone at 1 hour to 3.2% at 72 hours. Taken together, these results suggest that little free yttrium was associated with the conjugate and that little free radiometal was released during the course of the study. These data were used in determining radiation absorbed dose estimates for Y2B8 described below.

For tumor localization studies, 2B8-MX-DTPA was prepared and radiolabeled with $^{111}$Indium to a specific activity of 2.7 mCi/mg. One hundred microliters of labeled conjugate (approximately 24$\mu$ Ci) were subsequently injected into each of 12 athymic mice bearing Ramos B cell tumors. Tumors ranged in weight from 0.1 to 1.0 grams. At time points of 0, 24, 48, and 72 hours following injection, 50 $\mu$L of blood was removed by retro-orbital puncture, the mice sacrificed by cervical dislocation, and the tail, heart, lungs, liver, kidney, spleen, muscle, femur, and tumor removed. After processing and weighing the tissues, the radioactivity assiocated with each tissue specimen was determined using a gammma counter and the values expressed as percent injected dose per gram.

The results (not shown) evidenced that the tumor concentrations of the $^{111}$In-2B8-MX-DTPA increased steadily throughout the course of the experiment. Thirteen percent of the injected dose was accumulated in the tumor after 72 hours. The blood levels, by contrast, dropped during the experiment from over 30% at time zero to 13% at 72 hours. All other tissues (except muscle) contained between 1.3 and 6.0% of the injected dose per gram tissue by the end of the experiment; muscle tissue contained approximately 13% of the injected dose per gram.

D. Humnan Studies i. 2B8 and 2B8-MX-DTPA: Immunohistology Studies with Human Tissues The tissue reactivity of murine monoclonal antibody 2B8 was evaluated using a panel of 32 different human tissues fixed with acetone. Antibody 2B8 reacts with the anti-CD20 antigen which had a very restricted pattern of tissue distribution, being observed only in a subset of cells in lymphoid tissues including those of hematopoietic origin.

In the lymph node, immunoreactivity was observed in a population of mature cortical B-lymphocytes as well as proliferating cells in the germinal centers. Positive reactivity was also observed in the peripheral blood, B-cell areas of the tonsils, white pulp of the spleen, and with 40–70% of the medullary lymphocytes found in the thymus. Positive reactivity was also seen in the follicles of the lamina propria (Peyer's Patches) of the large intestines. Finally, aggregates or scattered lymphoid cells in the stroma of various organs, including the bladder, breast, cervix, esophagus, lung, parotid, prostate, small intestine, and stomach, were also positive with antibody 2B8 (data not shown).

All simple epithelial cells, as well as the stratified epithelia and epithelia of different organs, were found to be unreactive. Similarly, no reactivity was seen with neuroectodermal cells, including those in the brain, spinal cord and peripheral nerves. Mesenchymal elements, such as skeletal and smooth muscle cells, fibroblasts, endothelial cells, and polymorphonuclear inflammatory cells were also found to be negative (data not shown).

The tissue reactivity of the 2B8-MX-DTPA conjugate was evaluated using a panel of sixteen human tissues which had been fixed with acetone. As previously demonstrated with the native antibody (data not shown), the 2B8-MX-DTPA conjugate recognized the CD20 antigen which exhibited a highly restricted pattern of distribution, being found only on a subset of cells of lymphoid origin. In the lymph node, immunoreactivity was observed in the B cell population. Strong reactivity was seen in the white pulp of the spleen and in the medullary lymphocytes of the thymus. Immunoreactivity was also observed in scattered lymphocytes in the bladder, heart, large intestines, liver, lung, and uterus, and was attributed to the presence of inflammatory cells present in these tissues. As with the native antibody, no reactivity was observed with neuroectodermal cells or with mesenchymal elements (data not shown).

ii. Clinical Analysis of I2B8 (Imaging) and Y2B8 (Therapy)

a. Phase I/II Clinical Trial Single Dose Therapy Study

A Phase I/II clinical analysis of I2B8 (imaging) followed by treatment with a single therapeutic dose of Y2B8 is currently being conducted, For the single-dose study, the following schema is being followed:
1. Peripheral Stem Cell (PSC) or Bone Marrow (BM) Harvest with Purging;
2. I2B8 Imaging;
3. Y2B8 Therapy (three Dose Levels); and
4. PSC or Autologous BM Transplantation (if necessary based upon absolute neutrophil count below 500/mm$^3$ for three consecutive days or platelets below 20,000/mm$^3$ with no evidence of marrow recovery on bone marrow examination).

The Dose Levels of Y2B8 are as follows:

| Dose Level | Dose (mCi) |
|---|---|
| 1. | 20 |
| 2. | 30 |
| 3. | 40 |

Three patients are to be treated at each of the dose levels for determination of a Maximum Tolerated Dose ("MTD").

Imaging (Dosimetry) Studies are conducted as follows: each patient is involved in two in vivo biodistribution studies using I2B8. In the first study, 2 mg of I2B8 (5 mCi), is administered as an intravenous (i.v.) infusion over one hour; one week later 2B8 (ie, unconjugated antibody) is administered by i.v. at a rate not to exceed 250 mg/hr followed immediately by 2 mg of I2B8 (5 mCi) administered by i.v. over one hour. In both studies, immediately following the I2B8 infusion, each patient is imaged and imaging is repeated at time t=14–18 hr (if indicated), t=24 hr; t=72 hr; and t=96 hr (if indicated). Whole body average retention times for the indium [111] label are determined; such determinations are also made for recognizable organs or tumor lesions ("regions of interest").

The regions of interest are compared to the whole body concentrations of the label; based upon this comparison, an estimate of the localization and concentration of Y2B8 can be determined using standard protocols. If the estimated cumulative dose of Y2B8 is greater than eight (8) times the estimated whole body dose, or if the estimated cumulative dose for the liver exceeds 1500 $_c$Gy, no treatment with Y2B8 should occur.

If the imaging studies are acceptable, either 0.0 or 1.0 mg/kg patient body weight of 2B8 is administered by i.v. infusion at a rate not to exceed 250 mg/h. This is followed by administration of Y2B8 (10,20 or 40 mCi) at an i.v. infusion rate of 20 mCi/hr.

b. Phase I/II Clinical Trial: Multiple Dose Therapy Study

A Phase I/II clinical analysis of Y2B8 is currently being conducted. For the multiple-dose study, the following schema is being followed:
1. PSC or BM Harvest;
2. I2B8 Imaging;
3. Y2B8 Therapy (three Dose Levels) for four doses or a total cumulative dose of 80 mCi; and
4. PSC or Autologous BM Transplantation (based upon decision of medical practitioner).

The Dose Levels of Y2B8 are as follows:

| Dose Level | Dose (mCi) |
|---|---|
| 1. | 10 |
| 2. | 15 |
| 3. | 20 |

Three patients are to be treated at each of the dose levels for determination of an MTD.

Imaging (Dosimetry) Studies are conducted as follows: A preferred imaging dose for the unlabeled antibody (ie 2B8) will be determined with the first two patients. The first two patients will receive 100 mg of unlabeled 2B8 in 250 cc of normal saline over 4 hrs followed by 0.5 mCi of I2B8—blood will be sampled for biodistribution data at times t=0, t=10 min., t=120 min., t=24 hr, and t=48 hr. Patients will be scanned with multiple regional gamma camera images at times t=2 hr, t=24 hr and t=48 hr. After scanning at t=48 hr, the patients will receive 250 mg of 2B8 as described, followed by 4.5 mCi of I2B8—blood and scanning will then follow as described. If 100 mg of 2B8 produces superior imaging, then the next two patients will receive 50 mg of 2B8 as described, followed by 0.5 mCi of I2B8 followed 48 hrs later by 100 mg 2B8 and then with 4.5 mCi of I2B8. If 250 mg of 2B8 produces superior imaging, then the next two patients will receive 250 mg of 2B8 as described, followed by 0.5 mCi of I2B8 followed 48 hrs later with 500 mg 2B8 and then with 4.5 mCi of I2B8. Subsequent patients will be treated with the lowest amount of 2B8 that provides optimal imaging. Optimal imaging will be defined by: (1) best effective imaging with the slowest disappearance of antibody; (2) best distribution minimizing compartmentalization in a single organ; and (3) best subjective resolution of the lesion (tumor/background comparison).

For the first four patients, the first therapeutic dose of Y2B8 will begin 14 days after the last dose of I2B8; for subsequent patients, the first therapeutic dose of Y2B8 will begin between two to seven days after the I2B8.

Prior to treatment with Y2B8, for the patients other than the first four, 2B8 will be administered as described, followed by i.v. infusion of Y2B8 over 5–10 min. Blood will be sampled for biodistribution at times t=0, t=10 min., t=120 min., t=24 hr and t=48 hr. Patients will receive repetitive doses of Y2B8 (the same dose administered as with the first dose) approximately every six to eight weeks for a maximum of four doses, or total cumulative dose of 80 mCi. It is most preferred that patients not receive a subsequent dose of Y2B8 until the patients' WBC is greater than/equal to 3,000 and AGC is greater than/equal to 100,000.

Following completion of the three-dose level study, an MTD will be defined. Additional patients will then be enrolled in the study and these will receive the MTD.

II. CHIMERIC ANTI-CD20 ANTIBODY PRODUCTION ("C2B8")

A. Construction of Chimeric Anti-CD20 Immunoglobulin DNA Expression Vector

RNA was isolated from the 2B8 mouse hybridoma cell (as described in Chomczynki, P. et al., "Single step method of RNA isolation by acid guanidinium thiocyanate-phenol-chloroform extraction." Anal. Biochem. 162:156–159 (1987)). and cDNA was prepared therefrom. The mouse immunoglobulin light chain variable region DNA was isolated from the cDNA by polymerase chain reaction using a set of DNA primers with homology to mouse light chain signal sequences at the 5' end and mouse light chain J region at the 3' end. Primer sequences were as follows:

1. $V_L$ Sense (SEQ. ID. NO. 3)

5' ATC AC AGATCT CTC ACC ATG GAT TTT CAG GTG CAG ATT ATC AGC TTC 3'

(The underlined portion is a Bgl II site; the above-lined portion is the start codon.)

2. $V_L$ Antisense (SEQ. ID. NO. 4)

5' TGC AGC ATC CGTACG TTT GAT TTC CAG CTT 3'

(The underlined portion is a Bsi WI site.)

See, FIGS. 1 and 2A–E for the corresponding Bgl II and Bsi WI sites in TCAE 8, and FIGS. 3A–F for the corresponding sites in anti-CD20 in TCAE 8.

These resulting DNA fragment was cloned directly into the TCAE 8 vector in front of the human kappa light chain constant domain and sequenced. The determined DNA sequence for the murine variable region light chain is set forth in FIGS. 3A-F (SEQ. ID. NO. 5); see also FIG. 3, nucleotides 978 through 1362. FIG. 4 further provides the amino acid sequence from this murine variable region, and the CDR and framework regions. The mouse light chain variable region from 2B8 is in the mouse kappa VI family. See, Kabat, supra.

The mouse heavy chain variable region was similarly isolated and cloned in front of the human IgGl constant domains. Primers were as follows: p 1. $V_H$ Sense (SEQ. ID. NO. 6)

5' GCG GCT CCC ACGCGT GTC CTG TCC CAG 3'

(The underlined portion is an Mlu I site.)

2. $V_H$ Antisense (SEQ. ID. NO. 7)

5' GG(G/C) TGT TGT GCTAGC TG(A/C) (A/G)GA GAC (G/A)GT GA 3'

(The underlined portion is an Nhe I site.)

See, FIGS. 1 and 2A–E for corresponding Mlu I and Nhe I sites in TCAE 8, and FIGS. 3A–F for corresponding sites in anti-CD20 in TCAE 8.

The sequence for this mouse heavy chain is set forth in FIG. 5 (SEQ. ID. NO. 8); see also FIGS. 3A–F, nucleotide 2401 through 2820. FIG. 5 also provides the amino acid sequence from this murine variable region, and the CDR and framework regions. The mouse heavy chain variable region from 2B8 is in the mouse VH 2B family. See, Kabat, supra.

B. Creation of Chimeric Anti- CD20 Producing CHO and SP2/0 Transfectomas

Chinese hamster ovary ("CHO") cells DG44 were grown in SSFM II minus hypoxanthine and thymidine media (Gibco, Grand Island, N.Y., Form No. 91-0456PK); SP2/0 mouse myeloma cells were grown in Dulbecco's Modified Eagles Medium media ("DMEM") (Irvine Scientific, Santa Ana, Calif., Cat. No. 9024) with 5% fetal bovine serum and 20 ml/L glutamine added. Four million cells were electroporated with either 25 µg CHO or 50 µg SP2/0 plasmid DNA that had been restricted with Not I using a BTX 600 electroporation system (BTX, San Diego, Calif.) in 0.4 ml disposable cuvettes. Conditions were either 210 volts for CHO or 180 volts for SP2/0, 400 microfaradays, 13 ohms. Each electroporation was plated into six 96 well dishes (about 7,000 cells/well). Dishes were fed with media containing G418 (GENETICIN, Gibco, Cat. No. 860-1811) at 400 µg/ml active compound for CHO (media further included 50 µM hypoxanthine and 8 µM thymidine) or 800 µg/ml for SP2/0, two days following electroporation and thereafter 2 or 3 days until colonies arose. Supernatant from colonies was assayed for the presence of chimeric immunoglobulin via an ELISA specific for human antibody. Colonies producing the highest amount of immunoglobulin were expanded and plated into 96 well plates containing media plus methotrexate (25 nM for SP2/0 and 5 nM for CHO) and fed every two or three days. Supernatants were assayed as above and colonies producing the highest amount of immunoglobulin were examined. Chimeric anti-CD20 antibody was purified from supernatant using protein A affinity chromatography.

Purified chimeric anti-CD20 was analyzed by electrophoresis in polyacrylamide gels and estimated to be greater than about 95% pure. Affinity and specificity of the chimeric antibody was determined based upon 2B8. Chimeric anti-CD20 antibody tested in direct and competitive binding assays, when compared to murine anti-CD20 monoclonal antibody 2B8, evidenced comparable affinity and specificity on a number of CD20 positive B cells lines (data not presented). The apparent affinity constant ("Kap") of the chimeric antibody was determined by direct binding of $I^{125}$ radiolabeled chimeric anti-CD20 and compared to radiolabeled 2B8 by Scatchard plot; estimated Kap for CHO produced chimeric anti-CD20 was $5.2 \times 10^{-9}$M and for SP2/0 produced antibody, $7.4 \times 10^{-9}$M. The estimated Kap for 2B8 was $3.5 \times 10^{-9}$M. Direct competition by radioimmunoassay was utilized to confirm both the specificity and retention of immunoreactivity of the chimeric antibody by comparing its ability to effectively compete with 2B8. Substantially equivalent amounts of chimeric anti-CD20 and 2B8 antibodies were required to produce 50% inhibition of binding to CD20 antigens on B cells (data not presented), ie, there was a minimal loss of inhibiting activity of the anti-CD20 antibodies, presumably due to chimerization.

The results of Example II.B indicate, inter alia, that chimeric anti-CD20 antibodies were generated from CHO and SP2/0 transfectomas using the TCAE 8 vectors, and these chimeric antibodies had substantially the same specificity and binding capability as murine anti-CD20 monoclonal antibody 2B8.

C. Determination of Immunological Activity of Chimeric Anti-CD20 Antibodies i. Human C1q Analysis Chimeric anti-CD20 antibodies produced by both CHO and SP2/0 cell lines were evaluated for human C1q binding in a flow cytometry assay using fluorescein labeled C1q (C1q was obtained from Quidel, Mira Mesa, Calif., Prod. No. A400 and FITC label from Sigma, St. Louis Mo., Prod. No. F-7250; FITC. Labeling of C1q was accomplished in accordance with the protocol described in *Selected Methods In Cellular Immunology*, Michell & Shiigi, Ed. (W. H. Freeman & Co., San Francisco, Calif., 1980, p. 292). Analytical results were derived using a Becton Dickinson FACScan™ flow cytometer (fluorescein measured over a range of 515–545 nm). Equivalent amounts of chimeric anti-CD20 antibody, human IgG1,K myeloma protein (Binding Site, San Diego, Calif., Prod. No. BP078), and 2B8 were incubated with an equivalent number of CD20-positive SB cells, followed by a wash step with FACS buffer (0.2% BSA in PBS, pH 7.4, 0.02% sodium azide) to remove unattached antibody, followed by incubation with FITC labeled C1q. Following a 30–60 min. incubation, cells were again washed. The three conditions, including FITC-labeled C1q as a control, were analyzed on the FACScan™ following manufacturing instructions. Results are presented in FIG. 6.

Figure 6:
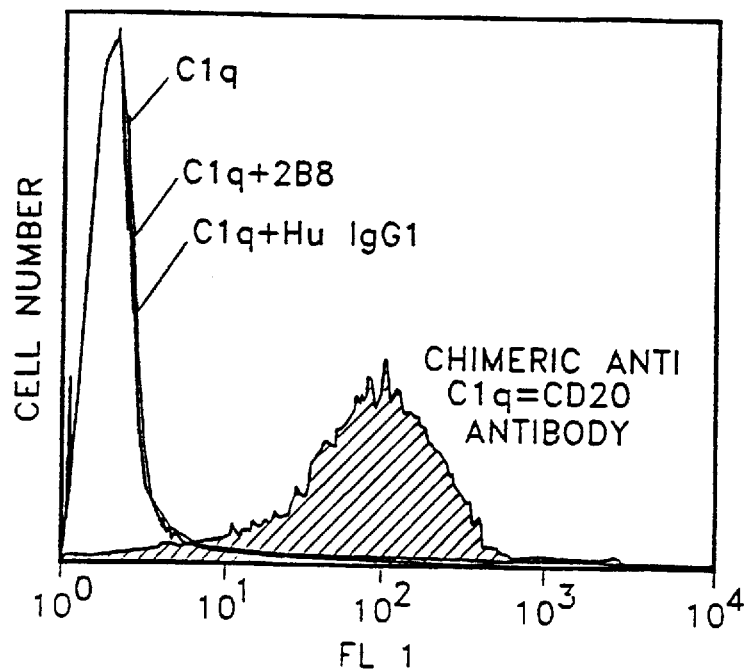
FIG. 6 are flow cytometry results evidencing binding of fluorescent-labeled human C1q to chimeric anti-CD20 antibody, including, as controls labeled C1q; labeled C1q and murine anti-CD20 monoclonal antibody 2B8; and labeled C1q and human IgG1,k.

As the results of FIG. 6 evidence, a significant increase in fluorescence was observed only for the chimeric anti-CD20 antibody condition; ie, only SB cells with adherent chimeric anti-CD20 antibody were C1q positive, while the other conditions produced the same pattern as the control.

ii. Complement Dependent Cell Lyses

Chimeric anti-CD20 antibodies were analyzed for their ability to lyse lymphoma cell lines in the presence of human serum (complement source). CD20 positive SB cells were labeled with $^{51}$Cr by admixing 100µ Ci of $^{51}$Cr with $1 \times 10^6$ SB cells for 1 hr at 37° C.; labeled SB cells were then incubated in the presence of equivalent amounts of human complement and equivalent amounts (0–50 µg/ml) of either chimeric anti-CD20 antibodies or 2B8 for 4 hrsat 37° C. (see, Brunner, K. T. et al., "Quantitative assay of the lytic action of immune lymphoid cells on $^{51}$Cr-labeled allogeneic target cells in vitro." *Immunology* 14:181–189 (1968). Results are presented in FIG. 7.

Figure 7:
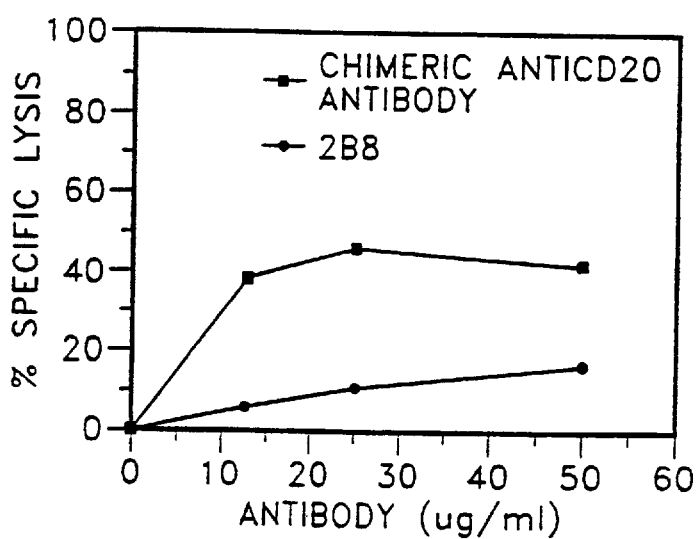
FIG. 7 represents the results of complement related lysis comparing chimeric anti-CD20 antibody and murine anti-CD20 monoclonal antibody 2B8.

The results of FIG. 7 indicate, inter alia, that chimeric anti-CD20 antibodies produced significant lysis (49%) under these conditions.

ii. Antibody Dependent Cellular Cytotoxicity Effector Assay

Figure 8:
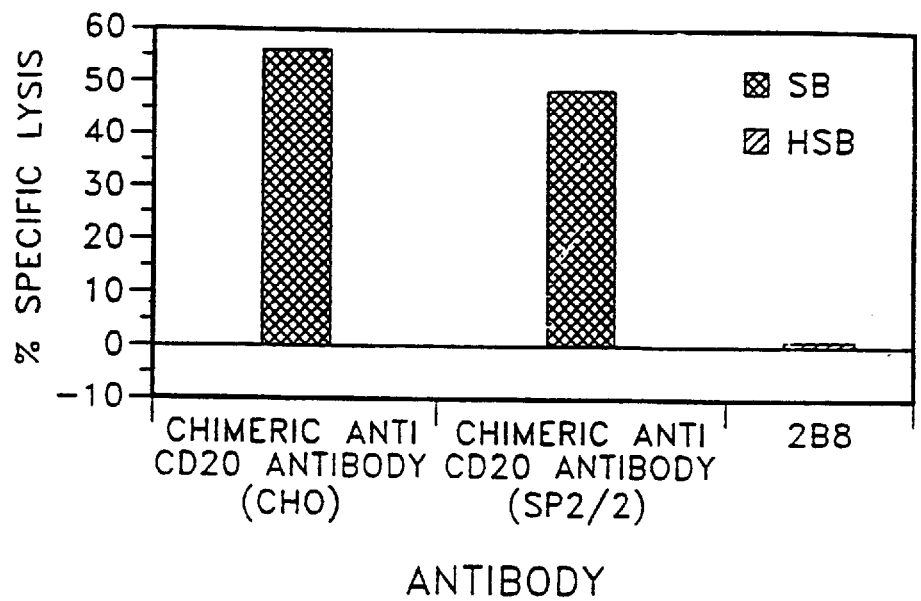
FIG. 8 represents the results of antibody mediated cellular cytotoxicity with in vivo human effector cells comparing chimeric anti-CD20 antibody and 2B8.

For this study, CD20 positive cells (SB) and CD20 negative cells (T cell leukemia line HSB; see, Adams, Richard, "Formal Discussion," Can. Res. 27:2479–2482 (1967); ATCC deposit no. ATCC CCL 120.1) were utilized; both were labeled with $^{51}$Cr. Analysis was conducted following the protocol described in Brunner, K. T. et al., "Quantitative assay of the lytic action of immune lymphoid cells on $^{51}$Cr-labeled allogeneic target cells in vitro; inhibition by isoantibody and drugs." *Immunology* 14:181–189 (1968); a substantial chimeric anti-CD20 antibody dependent cell mediated lysis of CD20 positive SB target cells ($^{51}$Cr-labeled) at the end of a 4 hr, 37° C. incubation, was observed and this effect was observed for both CHO and SP2/0 produced antibody (effector cells were human peripheral lymphocytes; ratio of effector cells:target was 100:1). Efficient lysis of target cells was obtained at 3.9 µg/ml. In contrast, under the same conditions, the murine anti-CD20 monoclonal antibody 2B8 had a statistically insignificant effect, and CD20 negative HSB cells were not lysed. Results are presented in FIG. 8.

The results of Example II indicate, inter alia, that the chimeric anti-CD20 antibodies of Example I were immunologically active.

III. DEPLETION OF B CELLS IN VIVO USING CHIMERIC ANTI-CD20

A Non-Human Primate Study

Three separate non-human primate studies were conducted. For convenience, these are referred to herein as "Chimeric Anti-CD20: CHO & SP2/0;" "Chimeric Anti-CD20: CHO;" and "High Dosage Chimeric Anti-CD20." Conditions were as follows:

Chimeric Anti-CD20: CHO & SP2/0

Six cynomolgus monkeys ranging in weight from 4.5 to 7 kilograms (White Sands Research Center, Alamogordo, N.Mex.) were divided into three groups of two monkeys each. Both animals of each group received the same dose of immunologically active chimeric anti-CD20 antibody. One animal in each group received purified antibody produced by the CHO transfectoma; the other received antibody produced by the SP2/0 transfectoma. The three groups received antibody dosages corresponding to 0.1 mg/kg, 0.4 mg/kg, and 1.6 mg/kg each day for four (4) consecutive days. The chimeric immunologically active anti-CD20 antibody, which was admixed with sterile saline, was administered by intravenous infusion; blood samples were drawn prior to each infusion. Additional blood samples were drawn beginning 24 hrs after the last injection (T=O) and thereafter on days 1, 3, 7, 14 and 28; blood samples were also taken thereafter at biweekly intervals until completion of the study at day 90.

Approximately 5 ml of whole blood from each animal was centrifuged at 2000 RPM for 5 min. Plasma was removed for assay of soluble chimeric anti-CD20 antibody levels. The pellet (containing peripheral blood leukocytes and red blood cells) was resuspended in fetal calf serum for fluorescent-labeled antibody analysis (see, "Fluorescent Antibody Labeling of Lymphoid Cell Population," infra.).

Chimeric Anti-CD20: CHO

Six cynomolgus monkeys ranging in weight from 4 to 6 kilograms (White Sands) were divided into three groups of two monkeys each. All animals were injected with immunologically active chimeric anti-CD20 antibodies produced from the CHO transfectoma (in sterile saline). The three groups were separated as follows: subgroup 1 received daily intravenous injections of 0.01 mg/kg of the antibody over a four (4) day period; subgroup 2 received daily intravenous injections of 0.4 mg/kg of the antibody over a four (4) day period; subgroup 3 received a single intravenous injection of 6.4 mg/kg of the antibody. For all three subgroups, a blood sample was obtained prior to initiation of treatment; additionally, blood samples were also drawn at T=0, 1, 3, 7, 14 and 28 days following the last injection, as described above, and these samples were processed for fluorescent labeled antibody analysis (see, "Fluorescent Antibody Labeling," infra.). In addition to peripheral blood B cell quantitation, lymph node biopsies were taken at days 7, 14 and 28 following the last injection, and a single cell preparation stained for quantitation of lymphocyte populations by flow cytometry.

High Dosage Chimeric Anti-CD20

Two cynomolgus monkeys (White Sands) were infused with 16.8 mg/kg of the immunologically active chimeric anti-CD20 antibodies from the CHO transfectomas (in sterile saline) weekly over a period of four consecutive weeks. At the conclusion of the treatment, both animals were anesthetized for removal of bone marrow; lymph node biopsies were also taken. Both sets of tissue were stained for the presence of B lymphocytes using Leu 16 by flow cytometry following the protocol described in Ling, N. R. et al., "B-cell and plasma cell antigens." *Leucocyte Typing III White Cell Differentiations Antigens*, A. J. McMichael, Ed. (Oxford University Press, Oxford UK, 1987), p. 302.

Fluorescent Antibody Labeling of Lymphoid Cell Population

After removal of plasma, leukocytes were washed twice with Hanks Balanced Salt Solution ("HBSS") and resuspended in a plasma equivalent volume of fetal bovine serum (heat inactivated at 56° C. for 30 min.). A 0.1 ml volume of the cell preparation was distributed to each of six (6), 15 ml conical centrifuge tubes Fluorescein labeled monoclonal antibodies with specificity for the human lymphocyte surface markers CD2 (AMAC, Westbrook, Me.), CD20 (Becton Dickinson) and human IgM (Binding Site, San Diego, Calif.) were added to 3 of the tubes for identifying T and B lymphocyte populations. All reagents had previously tested positive to the corresponding monkey lymphocyte antigens. Chimeric anti-CD20 antibody bound to monkey B cell surface CD20 was measured in the fourth tube using polyclonal goat anti-human IgG coupled with phycoerythrin (AMAC). This reagent was pre-adsorbed on a monkey Ig-sepharose column to prevent cross-reactivity to monkey Ig, thus allowing specific detection and quantitation of chimeric anti-CD20 antibody bound to cells. A fifth tube included both anti-IgM and anti-human IgG reagents for double stained B cell population. A sixth sample was included with no reagents for determination of autofluorescence. Cells were incubated with fluorescent antibodies for 30 min., washed and fixed with 0.5 ml of fixation buffer (0.15M NaCl, 1% paraformaldehyde, pH7.4) and analyzed on a Becton Dickinson FACScan™ instrument. Lymphocyte populations were initially identified by forward versus right angle light scatter in a dot-plot bitmap with unlabeled leucocytes. The total lymphocyte population was then isolated by gating out all other events. Subsequent fluorescence measurements reflected only gated lymphocyte specific events.

Depletion of Peripheral Blood B Lymphocytes

Figure 9A:
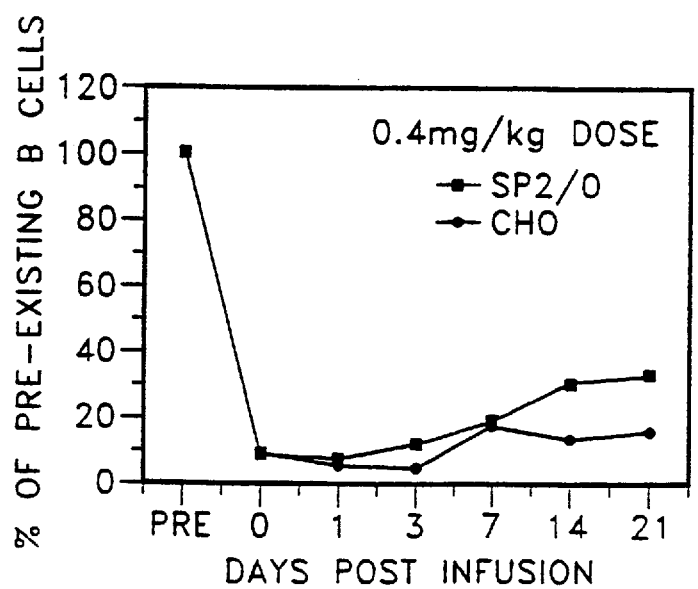
FIG. 9A, 9B and 9C provide the results of non-human primate peripheral blood B lymphocyte depletion after infusion of 0.4 mg/kg (A); 1.6 mg/kg (B); and 6.4 mg/kg (C) of immunologically active chimeric anti-CD20 antibody.
Figure 9B:
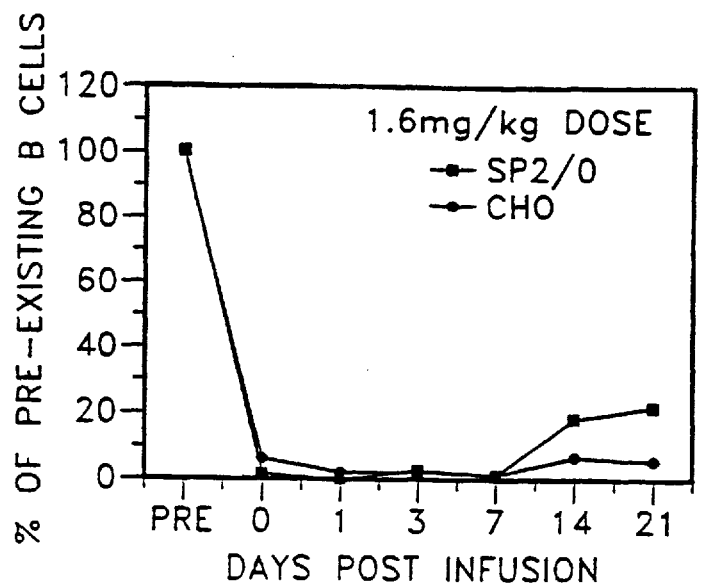

No observable difference could be ascertained between the efficacy of CHO and SP2/0 produced antibodies in depleting B cells in vivo, although a slight increase in B cell recovery beginning after day 7 for monkeys injected with chimeric anti-CD20 antibodies derived from CHO transfectomas at dosage levels 1.6 mg/kg and 6.4 mg/kg was observed and for the monkey injected with SP2/0 producing antibody at the 0.4 mg/kg dose level. FIGS. 9A, B and C. provide the results derived from the chimeric anti-CD20:CHO & SP2/0 study, with FIG. 9A directed to the 0.4 mg/kg dose level; FIG. 9B directed to the 1.6 mg/kg dose level; and FIG. 9C directed to the 6.4 mg/kg dose level.

Figure 9C:
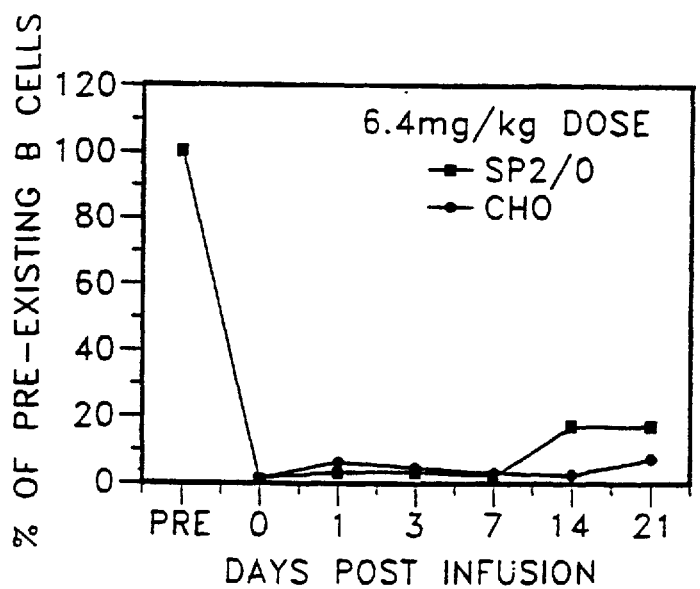

As is evident from FIGS. 9A–C, there was a dramatic decrease (>95%) in peripheral B cell levels after the therapeutic treatment across all tested dose ranges, and these levels were maintained up to seven (7) days post infusion; after this period, B cell recovery began, and, the time of recovery initiation was independent of dosage levels.

Figure 10:
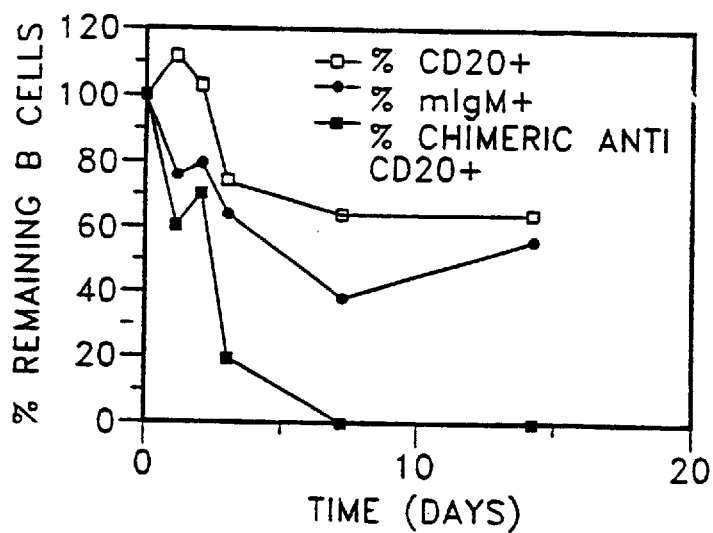
FIG. 10 provides the results of, inter alia, non-human primate peripheral blood B lymphocyte depletion after infusion of 0.01 mg/kg of immunologically active chimeric anti-CD20 antibody.

In the Chimeric Anti-CD20: CHO study, a 10-fold lower antibody dosage concentration (0.01 mg/kg) over a period of four daily injections (0.04 mg/kg total) was utilized. FIG. 10 provides the results of this study. This dosage depleted the peripheral blood B cell population to approximately 50% of normal levels estimated with either the anti-surface IgM or the Leu 16 antibody. The results also indicate that saturation of the CD20 antigen on the B lymphocyte population was not achieved with immunologically active chimeric anti-CD20 antibody at this dose concentration over this period of time for non-human primates; B lymphocytes coated with the antibody were detected in the blood samples during the initial three days following therapeutic treatment. However, by day 7, antibody coated cells were undetectable.

Table I summarizes the results of single and multiple doses of immunologically active chimeric anti-CD20 antibody on the peripheral blood populations; single dose condition was 6.4 mg/kg; multiple dose condition was 0.4 mg/kg over four (4) consecutive days (there results were derived from the monkeys described above).

TABLE I

PERIPHERAL BLOOD POPULATION FROM C2B8 PRIMATE STUDY

| Monkey | Dose | Day | CD2 | Anti-Hu IgG |
|---|---|---|---|---|
| A | 0.4 mg/kg | Prebleed | 81.5 | — |
|   | (4 doses) | 0 | 86.5 | 0.2 |
|   |   | 7 | 85.5 | 0.0 |
|   |   | 21 | 93.3 | — |
|   |   | 28 | 85.5 | — |
| B | 0.4 mg/kg | Prebleed | 81.7 | — |
|   | (4 doses) | 0 | 94.6 | 0.1 |
|   |   | 7 | 92.2 | 0.1 |
|   |   | 21 | 84.9 | — |
|   |   | 28 | 84.1 | — |
| C | 6.4 mg/kg | Prebleed | 77.7 | 0.0 |
|   | (1 dose) | 7 | 85.7 | 0.1 |
|   |   | 21 | 86.7 | — |
|   |   | 28 | 76.7 | — |
| D | 6.4 mg/kg | Prebleed | 85.7 | 0.1 |
|   | (1 dose) | 7 | 94.7 | 0.1 |
|   |   | 21 | 85.2 | — |
|   |   | 28 | 85.9 | — |

| Monkey | Anti-Hu IgG + Anti-Hu IgM* | Leu-16 | % B Cell Depletion |
|---|---|---|---|
| A | — | 9.4 | 0 |
|   | 0.3 | 0.0 | 97 |
|   | 0.1 | 1.2 | 99 |
|   | — | 2.1 | 78 |
|   | — | 4.1 | 66 |
| B | — | 14.8 | 0 |
|   | 0.2 | 0.1 | 99 |
|   | 0.1 | 0.1 | 99 |
|   | — | 6.9 | 53 |
|   | — | 8.7 | 41 |
| C | 0.2 | 17.0 | 0 |
|   | 0.1 | 0.0 | 99 |
|   | — | 14.7 | 15 |
|   | — | 8.1 | 62 |
| D | 0.1 | 14.4 | 0 |
|   | 0.2 | 0.0 | 99 |
|   | — | 9.2 | 46 |
|   | — | 6.7 | 53 |

*Double staining population which indicates extent of chimeric anti-CD20 coated B cells.

The data summarized in Table I indicates that depletion of B cells in peripheral blood under conditions of antibody excess occurred rapidly and effectively, regardless of single or multiple dosage levels. Additionally, depletion was observed for at least seven (7) days following the last injection, with partial B cell recovery observed by day 21.

Table II summarizes the effect of immunologically active, chimeric anti-CD20 antibodies on cell populations of lymph nodes using the treatment regimen of Table I (4 daily doses of 0.4 mg/kg; 1 dose of 6.4 mg/kg); comparative values for normal lymph nodes (control monkey, axillary and inguinal) and normal bone marrow (two monkeys) are also provided.

TABLE II

CELL POPULATIONS OF LYMPH NODES

| Monkey | Dose | Day | CD2 | Anti-Hu IgG |
|---|---|---|---|---|
| A | 0.4 mg/kg | 7 | 66.9 | — |
|   | (4 doses) | 14 | 76.9 | 19.6 |
|   |   | 28 | 61.6 | 19.7 |
| B | 0.4 mg/kg | 7 | 59.4 | — |
|   | (4 doses) | 14 | 83.2 | 9.9 |
|   |   | 28 | 84.1 | 15.7 |
| C | 6.4 mg/kg | 7 | 75.5 | — |
|   | (1 dose) | 14 | 74.1 | 17.9 |
|   |   | 28 | 66.9 | 23.1 |
| D | 6.4 mg/kg | 7 | 83.8 | — |
|   | (1 dose) | 14 | 74.1 | 17.9 |
|   |   | 28 | 84.1 | 12.8 |

| Monkey | Anti-Hu IgG + Anti-Hu IgM | Leu-16 | % B Lymphocyte Depletion |
|---|---|---|---|
| A | 7.4 | 40.1 | 1 |
|   | 0.8 | 22.6 | 44 |
|   | — | 26.0 | 36 |
| B | 29.9 | 52.2 | 0 |
|   | 0.7 | 14.5 | 64 |
|   | — | 14.6 | 64 |
| C | 22.3 | 35.2 | 13 |
|   | 1.1 | 23.9 | 41 |
|   | — | 21.4 | 47 |
| D | 12.5 | 19.7 | 51 |
|   | 0.2 | 8.7 | 78 |
|   | — | 12.9 | 68 |

|  | CD2 | Anti-Hu IgG + Anti-Hu IgM | Anti-Hu IgM | Leu-16 | % B Lymphocyte Depletion |
|---|---|---|---|---|---|
| Normal Lymph Nodes |  |  |  |  |  |
| Control 1 |  |  |  |  |  |
| Axillary | 55.4 | 25.0 | — | 41.4 | NA |
| Inguinal | 52.1 | 31.2 | — | 39.5 | NA |
| Normal Bone Marrow |  |  |  |  |  |
| Control 2 | 65.3 | 19.0 | — | 11.4 | NA |
| Control 3 | 29.8 | 28.0 | — | 16.6 | NA |

The results of Table II evidence effective depletion of B lymphocytes for both treatment regimens. Table II further indicates that for the non-human primates, complete saturation of the B cells in the lymphatic tissue with immunologically active, chimeric anti-CD20 antibody was not achieved; additionally, antibody coated cells were observed seven (7) days after treatment, followed by a marked depletion of lymph node B cells, observed on day 14.

Based upon this data, the single High Dosage Chimeric Anti-CD20 study referenced above was conducted, principally with an eye toward pharmacology/toxicology determination. Ie this study was conducted to evaluate any toxicity associated with the administration of the chimeric antibody, as well as the efficacy of B cell depletion from peripheral blood lymph nodes and bone marrow. Additionally, because the data of Table II indicates that for that study, the majority of lymph node B cells were depleted between 7 and 14 days following treatment, a weekly dosing regimen might evidence more efficacious results. Table III summarizes the results of the High Dosage Chimeric Anti-CD20 study.

TABLE III

CELL POPULATIONS OF LYMPH NODES AND BONE MARROW

| Monkey | CD2 | CD20[a] | mIgM + anti-C2B8[b] | C2B8[c] | Day[d] |
|---|---|---|---|---|---|
| *Inguinal Lymph Node* | | | | | |
| E | 90.0 | 5.3 | 4.8 | 6.5 | 22 |
| F | 91.0 | 6.3 | 5.6 | 6.3 | 22 |
| G | 89.9 | 5.0 | 3.7 | 5.8 | 36 |
| H | 85.4 | 12.3 | 1.7 | 1.8 | 36 |
| *Bone Marrow* | | | | | |
| E | 46.7 | 4.3 | 2.6 | 2.8 | 22 |
| F | 41.8 | 3.0 | 2.1 | 2.2 | 22 |
| G | 35.3 | 0.8 | 1.4 | 1.4 | 36 |
| H | 25.6 | 4.4 | 4.3 | 4.4 | 36 |

[a]Indicates population stained with Leu 16.
[b]Indicates double staining population, positive for surface IgM cells and chimeric antibody coated cells.
[c]Indicates total population staining for chimeric antibody including double staining surface IgM positive cells and single staining (surface IgM negative) cells.
[d]Days after injection of final 16.8 mg/kg dose.

Both animals evaluated at 22 days post treatment cessation contained less than 5% B cells, as compared to 40% in control lymph nodes (see, Table II, supra). Similarly, in the bone marrow of animals treated with chimeric anti-CD20 antibody, the levels of CD20 positive cells were less than 3% as compared to 11–15% in the normal animals (see, Table II, supra). In the animals evaluated at 36 days post treatment cessation, one of the animals (H) had approximately 12% B cells in the lymph node and 4.4% B cells in bone marrow, while the other (G) had approximately 5% B cells in the lymph node and 0.8% in the bone marrow—the data is indicative of significant B cell depletion.

The results of Example III, A indicate, inter alia, that low doses of immunologically active, chimeric anti-CD20 leads to long-term peripheral blood B cell depletion in primates. The data also indicates that significant depletion of B cell populations was achieved in peripheral lymph nodes and bone marrow when repetitive high doses of the antibody were administered. Continued follow-up on the test animals has indicated that even with such severe depletion of peripheral B lymphocytes during the first week of treatment, no adverse health effects have been observed. Furthermore, as recovery of B cell population was observed, a conclusion to be drawn is that the pluripotent stem cells of these primates were not adversely affected by the treatment.

B. Clinical Analysis of C2B8 i. Phase I/II Clinical Trial of C2B8: Single Dose Therapy Study

Fifteen patients having histologically documented relapsed B cell lymphoma have been treated with C2B8 in a Phase I/II Clinical Trial. Each patient received a single dose of C2B8 in a dose-escalating study; there were three patients per dose: 10 mg/m$^2$; 50 mg/m$^2$; 100 mg/m$^2$; 250 mg/m$^2$ and 500 mg/m$^2$. Treatment was by i.v. infusion through an 0.22 micron in-line filter with C2B8 being diluted in a final volume of 250 cc or a maximal concentration of 1 mg/ml of normal saline. Initial rate was 50 cc/hr for the first hour; if no toxicity was seen, dose rate was able to be escalated to a maximum of 200 cc/hr.

Toxicity (as indicated by the clinician) ranged from "none", to "fever" to "moderate" (two patients) to "severe" (one patient); all patients completed the therapy treatment. Peripheral Blood Lymphocytes were analyzed to determine, inter alia, the impact of C2B8 on T-cells and B-cells. Consistently for all patients, Peripheral Blood B Lymphocytes were depleted after infusion with C2B8 and such depletion was maintained for in excess of two weeks.

Figure 14A:
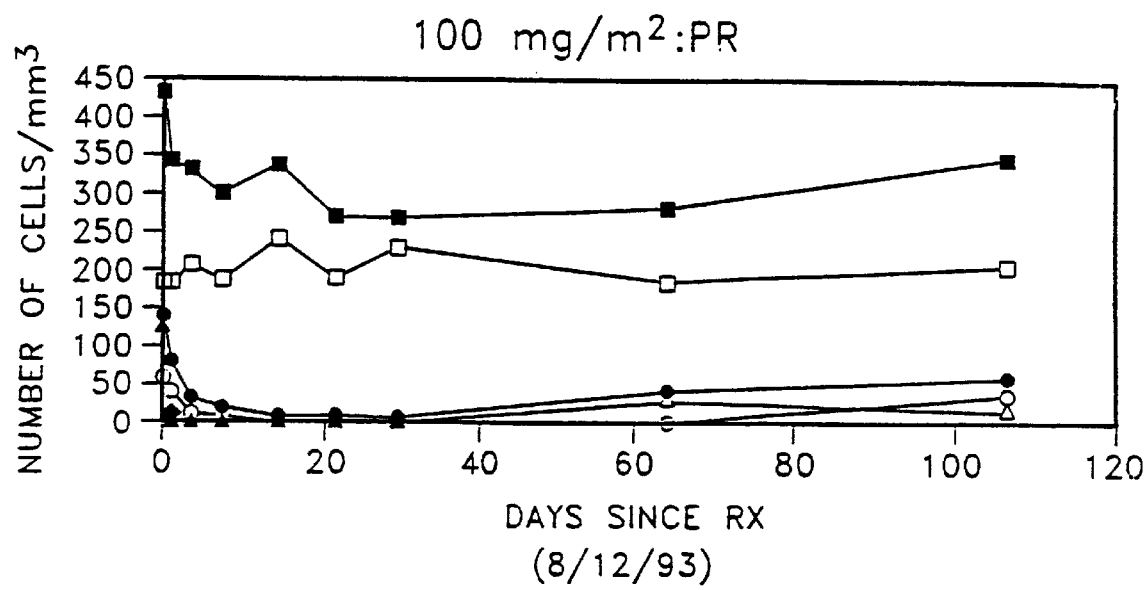
FIGS. 14A and 14B provide results from a Phase I/II clinical analysis of C2B8 evidencing B-cell population depletion over time for patients evidencing a partial remission of the disease (14A) and a minor remission of the disease (14B).
Figure 14B:
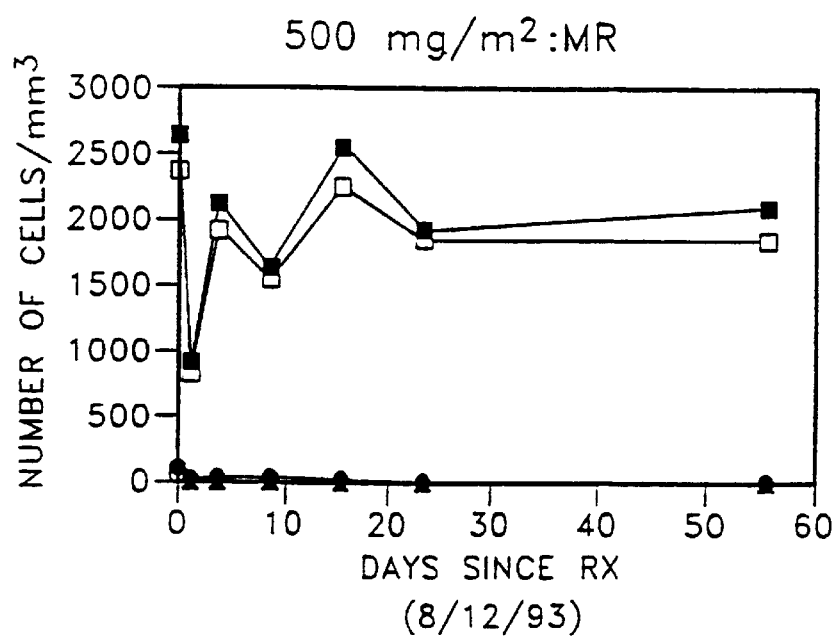

One patient (receiving 100 mg/$^2$ of C2B8) evidenced a Partial Response to the C2B8 treatment (reduction of greater than 50% in the sum of the products of the perpendicular diameters of all measurable indicator lesions lasting greater than four weeks, during which no new lesions may appear and no existing lesions may enlarge); at least one other patient (receiving 500 mg/m$^2$) evidenced a Minor Response to the C2B8 treatment (reduction of less than 50% but at least 25% in the sum of the products of the two longest perpendicular diameters of all measurable indicator lesions). For presentational efficiency, results of the PBLs are set forth in FIGS. 14A and B; data for the patient evidencing a PR is set forth in FIG. 14; for the patient evidencing an MR, data is set forth in FIG. 14B. In FIGS. 14A and B, the following are applicable: ■=Lymphocytes; ⊟=CD3+ cells (T cells); ▲=CD20$^+$ cells; ●=CD19$^+$ cells; ⊖=Kappa; ▲=lambda; and ♦=C2B8. As evidenced, the B cell markers CD20 and CD 19, Kappa and Lambda, were depleted for a period in excess of two weeks; while there was a slight, initial reduction in T-cell counts, these returned to an approximate base-line level in a relatively rapid time-frame.

ii. Phase I/II Clinical Trial of C2B8: Multiple Dose Therapy Study

Patients having histologically confirmed B cell lymphoma with measurable progressive disease are eligible for this study which is separated into two parts: in Phase I, consisting of a dose escalation to characterize dose limiting toxicities and determination of biologically active tolerated dose level, groups of three patients will receive weekly i.v. infusions of C2B8 for a total of four (4) separate infusions. Cumulative dose at each of the three levels will be as follows: 500 mg/m$^2$ (125 mg/m$^2$/infusion); 1000 mg/m$^2$ (250 mg/m$^2$/infusion);

1500 mg/m$^2$ (375 mg/m$^2$/infusion. A biologically active tolerated dose is defined, and will be determined, as the lowest dose with both tolerable toxicity and adequate activity); in Phase II, additional patients will receive the biologically active tolerated dose with an emphasis on determining the activity of the four doses of C2B8.

IV. COMBINATION THERAPY: C2B8 AND Y2B8

A combination therapeutic approach using C2B8 and Y2B8 was investigated in a mouse xenographic model (nu/nu mice, female, approximately 10 weeks old) utilizing a B cell lymphoblastic tumor (Ramos tumor cells). For comparative purposes, additional mice were also treated with C2B8 and Y2B8.

Ramos tumor cells (ATCC, CRL 1596) were maintained in culture using RPMI-1640 supplemented with 10% fetal calf serum and glutamine at 37° C. and 5% CO$_2$. Tumors were initiated in nine female nude mice approximately 7–10 weeks old by subcutaneous injection of 1.7×10$^6$ Ramos cells in a volume of 0.10 ml (HBSS) using a 1 cc syringe fitted with 25 g needle. All animals were manipulated in a laminar flow hood and all cages, bedding, food and water were autoclaved. Tumor cells were passaged by excising tumors and passing these through a 40 mesh screen; cells were washed twice with 1× HBSS (50 ml) by centrifugation (1300 RPM), resuspended in Ix HBSS to 10×10$^6$ cells/ml, and frozen at −70° C. until used.

For the experimental conditions, cells from several frozen lots were thawed, pelleted by centrifugation (1300 RPM)

and washed twice with 1× HBSS. Cells were then resuspended to approximately $2.0 \times 10^6$ cells/ml. Approximately 9 to 12 mice were injected with 0.10 ml of the cell suspension (s.c.) using a 1 cc syringe fitted with a 25 g needle; injections were made on the animal's left side, approximately mid-region. Tumors developed in approximately two weeks. Tumors were excised and processed as described above. Study mice were injected as described above with $1.67 \times 10^6$ cells in 0.10 ml HBSS.

Based on preliminary dosing experiments, it was determined that 200 mg of C2B8 and 100μ Ci of Y2B8 would be utilized for the study. Ninety female nu/nu mice (approximately 10 weeks old) were injected with the tumor cells. Approximately ten days later, 24 mice were assigned to four study groups (six mice/group) while attempting to maintain a comparable tumor size distribution in each group (average tumor size, expressed as a product of length×width of the tumor, was approximately 80 mm$^2$). The following groups were treated as indicated via tail-vain injections using a 100 μl Hamilton syringe fitted with a 25 g needle:

A. Normal Saline
B. Y2B8 (100μ Ci)
C. C2B8 (200 μg); and
D. Y2B8 (100μ Ci)+C2B8 (200 μg)

Groups tested with C2B8 were given a second C2B8 injection (200 μg/mouse) seven days after the initial injection. Tumor measurements were made every two or three days using a caliper.

Preparation of treatment materials were in accordance with the following protocols:

A Preparation of Y2B8

Yttrium-[90] chloride (6 mCi) was transformed to a polypropylene tube and adjusted to pH 4.1–4.4 using metal free 2M sodium acetate. 2B8-MX-DTPA (0.3 mg in normal saline; see above for preparation of 2B8-MX-DTPA) was added and gently mixed by vortexing. After 15 min. incubation, the reaction was quenched by adding 0.05× volume 20 mM EDTA and 0.05×volume 2M sodium acetate. Radioactivity concentration was determined by diluting 5.0 μl of the reaction mixture in 2.5 ml 1× PBS containing 75 mg/ml HSA And 1 mM DTPA ("formulation buffer"); counting was accomplished by adding 10.0 μl to 20 ml of Ecolume™ scintillation cocktail. The remainder of the reactive mixture was added to 3.0 ml formulation buffer, sterile filtered and stored at 2°–8° C. until used. Specific activity (14 mCi/mg at time of injection) was calculated using the radioactivity concentration and the calculated protein concentration based upon the amount of antibody added to the reaction mixture. Protein-associated radioactivity was determined using instant thin-layer chromatography. Radioincorporation was 95%. Y2B8 was diluted in formulation buffer immediately before use and sterile-filtered (final radioactivity concentration was 1.0 mCi/ml).

B. Preparation of C2B8

C2B8 was prepared as described above. C2B8 was provided as a sterile reagent in normal saline at 5.01 mg/ml. Prior to injection, the C2B8 was diluted in normal saline to 2.0 mg/ml and sterile filtered.

C. Results

Figure 11:
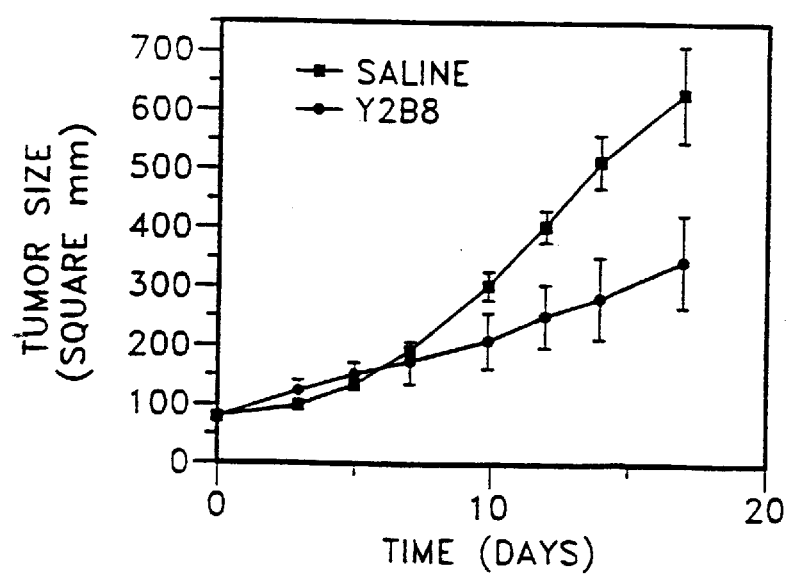
FIG. 11 provides results of the tumoricidal impact of Y2B8 in a mouse xenographic model utilizing a B cell lymphoblastic tumor.
Figure 12:
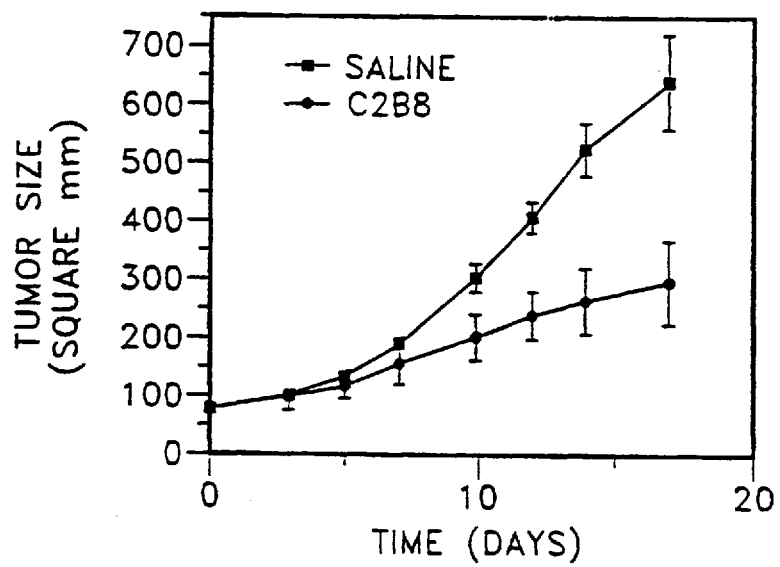
FIG. 12 provides results of the tumoricidal impact of C2B8 in a mouse xenographic model utilizing a B cell lymphoblastic tumor.

Following treatment, tumor size was expressed as a product of length and width, and measurements were taken on the days indicated in FIG. 11 (Y2B8 vs. Saline); FIG. 12 (C2B8 vs. Saline); and FIG. 13 (Y2B8+C2B8 vs. Saline). Standard error was also determined.

Figure 13:
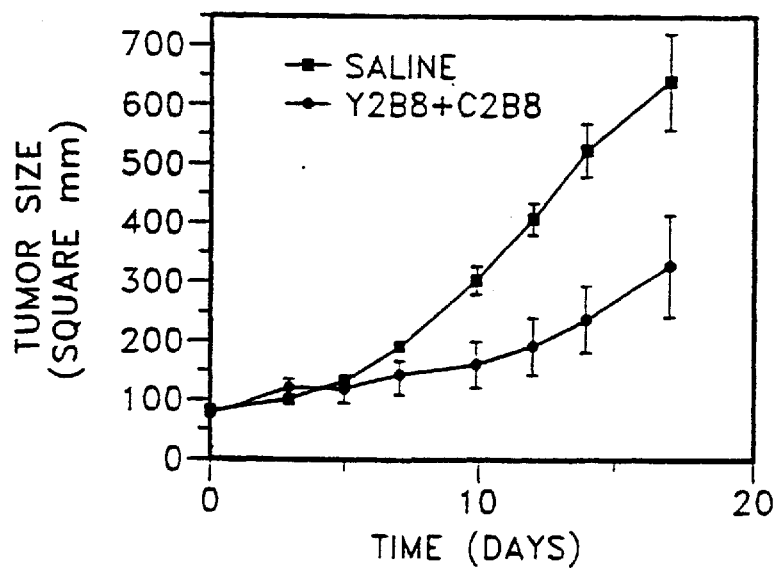
FIG. 13 provides results of the tumoricidal impact of a combination of Y2B8 and C2B8 in a mouse xenographic model utilizing a B cell lymphoblastic tumor.

As indicated in FIG. 13, the combination of Y2B8 and C2B8 exhibited tumoricidal effects comparable to the effects evidenced by either Y2B8 or C2B8.

V. ALTERNATIVE THERAPY STRATEGIES

Alternative therapeutic strategies recognized in view of the foregoing examples are evident. One such strategy employs the use of a therapeutic dose of C2B8 followed within about one week with a combination of either 2B8 and radioabeled 2B8 (eg, Y2B8); or 2B8, C2B8 and, eg Y2B8; or C2B8 and, eg Y2B8. An additional strategy is utilization of radiolabeled C2B8—such a strategy allows for utilization of the benefits of the immunologically active portion of C2B8 plus those benefits associated with a radiolabel. Preferred radiolabels include yttrium-90 given the larger circulating half-life of C2B8 versus the murine antibody 2B8. Because of the ability of C2B8 to deplete B-cells, and the benefits to be derived from the use of a radiolabel, a preferred alternative strategy is to treat the patient with C2B8 (either with a single dose or multiple doses) such that most, if not all, peripheral B cells have been depleted. This would then be followed with the use of radiolabeled 2B8; because of the depletion of peripheral B cells, the radiolabeled 2B8 stands an increased chance of targeting tumor cells. Iodine [131] labeled 2B8 is preferably utilized, given the types of results reported in the literature with this label (see Kaminski). An alternative preference involves the use of a radiolabeled 2B8 (or C2B8) first in an effort to increase the permeability of a tumor, followed by single or multiple treatments with C2B8; the intent of this strategy is to increase the chances of the C2B8 in getting both outside and inside the tumor mass. A further strategy involved the use of chemotherapeutic agenst in combination with C2B8. These strategies include so-called "staggered" treatments, ie, treatment with chemotherapeutic agent, followed by treatment with C2B8, followed by a repetition of this protocol. Alternatively, initial treatment with a single or multiple doses of C2B8, thereafter followed with chemotherapeutic treatement, is viable. Preferred chemotherapeutic agents include, but are not limited to: cyclophlsphamide; doxorubicin; vincristine; and prednisone, See Armitage, J. O. et al., Cancer 50:1695 (1982), incorporated herein by reference.

The foregoing alternative therapy strategies are not intended to be limiting, but rather are presented as being representative.

VI. DEPOSIT INFORMATION

Anti-CD20 in TCAE 8 (transformed in *E. coli* for purposes of deposit) was deposited with the American Type Culture Collection (ATCC), 12301 Parklawn Drive, Rockville, Md., 20852, under the provisions of the Budapest Treaty for the International Recognition of the Deposit of Microorganisms for the Purpose of Patent Procedure ("Budapest Treaty"). The microorganism was deposited with the ATCC on Nov. 4, 1992 and tested by the ATCC on Nov. 9, 1992, and determined to be viable on that date. The ATCC has assigned this microorganism for the following ATCC deposit number: ATCC 69119 (anti-CD20 in TCAE 8). Hybridoma 2B8 was deposited with the ATCC on Jun. 22, 1993 under the provisions of the Budapest Treaty. The viability of the culture was determined on Jun. 25, 1993 and the ATCC has assigned this hybridoma the following ATCC deposit number: HB 11388.

What is claimed is:

1. A method of treating B-cell lymphoma which includes the following steps: (i) administering, at a first administration period, a radiolabeled anti-CD20 antibody, wherein said antibody is selected from the group consisting of the chimeric anti-CD20 antibody produced by transfectoma TCAE 8, which has been accorded American Type Culture Collection Deposit No. ATCC 69119, and the murine anti-CD20 antibody secreted by a hybridoma identified by American Type Culture Collection Deposit No. HB 11388; and (ii) subsequently administering after step (i) at least one dosage of a chimeric anti-CD20 antibody produced by transfectoma TCAE 8, which has been accorded American Type Culture Collection Deposit No. ATCC 69119.

2. The method of claim 1, wherein multiple dosages of said chimeric anti-CD20 antibodies are administered after said initial administration (i) of said radiolabeled anti-CD20 antibody.

3. The method of claim 1, wherein said radiolabeled antibody administered in step (i) is a radiolabeled murine anti-CD20 antibody, and said murine anti-CD20 antibody is secreted by the hybridoma identified by American Type Culture Collection Deposit No. HB 11388.

4. The method of claim 1, wherein said radiolabeled antibody administered in step (i) is a radiolabeled chimeric anti-CD20 antibody, wherein said chimeric anti-CD20 antibody is produced by transfectoma TCAE 8, which has been accorded American Type Culture Collection Deposit No. ATCC 69119.

5. The method of claim 1, which further includes harvesting of peripheral stem cells (PSC's) or bone marrow (BM) prior to treatment.

6. The method of claim 5, wherein said harvested PSC's or BM is reinfused after treatment.

7. The method of claim 1, wherein the radiolabel contained in said radiolabeled antibody administered in step (i) is selected from the group consisting of iodine (131), indium (131), indium (111), and yttrium (90).

* * * * *

UNITED STATES PATENT AND TRADEMARK OFFICE
Certificate

Patent No. 5,843,439                                                      Patented: December 1, 1998

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Darrell R. Anderson, Escondido, CA (US); Nabil Hanna, Olivehain, CA (US); John E. Leonard, Encinitas, CA (US); Roland A. Newman, San Diego, CA (US); Mitchell Reff, San Diego, CA (US); William H. Rastetter, Rancho Santa Fe, CA (US); and Paul C. Chinn, Carlsbad, CA (US).

Signed and Sealed this Twenty-fifth Day of March 2008.

JEAN F. VOLLANO
*Quality Assurance Specialist*
Technology Center 1600

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:1:

| | |
|---|---|
| GGGAGCTTGG ATCGATCCTC TATGGTT | 27 |

( 2 ) INFORMATION FOR SEQ ID NO:2:

( i ) SEQUENCE CHARACTERISTICS:
    ( A ) LENGTH: 8540 base pairs
    ( B ) TYPE: nucleic acid
    ( C ) STRANDEDNESS: single
    ( D ) TOPOLOGY: circular ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

| | | | | | | |
|---|---|---|---|---|---|---|
| GACGTCGCGG | CCGCTCTAGG | CCTCCAAAAA | AGCCTCCTCA | CTACTTCTGG | AATAGCTCAG | 60 |
| AGGCCGAGGC | GGCCTCGGCC | TCTGCATAAA | TAAAAAAAAT | TAGTCAGCCA | TGCATGGGGC | 120 |
| GGAGAATGGG | CGGAACTGGG | CGGAGTTAGG | GGCGGGATGG | GCGGAGTTAG | GGGCGGGACT | 180 |
| ATGGTTGCTG | ACTAATTGAG | ATGCATGCTT | TGCATACTTC | TGCCTGCTGG | GGAGCCTGGG | 240 |
| GACTTTCCAC | ACCTGGTTGC | TGACTAATTG | AGATGCATGC | TTTGCATACT | TCTGCCTGCT | 300 |
| GGGGAGCCTG | GGGACTTTCC | ACACCCTAAC | TGACACACAT | TCCACAGAAT | TAATTCCCCT | 360 |
| AGTTATTAAT | AGTAATCAAT | TACGGGGTCA | TTAGTTCATA | GCCCATATAT | GGAGTTCCGC | 420 |
| GTTACATAAC | TTACGGTAAA | TGGCCCGCCT | GGCTGACCGC | CCAACGACCC | CCGCCCATTG | 480 |
| ACGTCAATAA | TGACGTATGT | TCCCATAGTA | ACGCCAATAG | GGACTTTCCA | TTGACGTCAA | 540 |
| TGGGTGGACT | ATTTACGGTA | AACTGCCCAC | TTGGCAGTAC | ATCAAGTGTA | TCATATGCCA | 600 |
| AGTACGCCCC | CTATTGACGT | CAATGACGGT | AAATGGCCCG | CCTGGCATTA | TGCCCAGTAC | 660 |
| ATGACCTTAT | GGGACTTTCC | TACTTGGCAG | TACATCTACG | TATTAGTCAT | CGCTATTACC | 720 |
| ATGGTGATGC | GGTTTTGGCA | GTACATCAAT | GGGCGTGGAT | AGCGGTTTGA | CTCACGGGGA | 780 |
| TTTCCAAGTC | TCCACCCCAT | TGACGTCAAT | GGGAGTTTGT | TTTGGCACCA | AAATCAACGG | 840 |
| GACTTTCCAA | AATGTCGTAA | CAACTCCGCC | CCATTGACGC | AAATGGGCGG | TAGGCGTGTA | 900 |
| CGGTGGGAGG | TCTATATAAG | CAGAGCTGGG | TACGTGAACC | GTCAGATCGC | CTGGAGACGC | 960 |
| CATCACAGAT | CTCTCACCAT | GAGGGTCCCC | GCTCAGCTCC | TGGGGCTCCT | GCTGCTCTGG | 1020 |
| CTCCCAGGTG | CACGATGTGA | TGGTACCAAG | GTGGAAATCA | AACGTACGGT | GGCTGCACCA | 1080 |
| TCTGTCTTCA | TCTTCCCGCC | ATCTGATGAG | CAGTTGAAAT | CTGGAACTGC | CTCTGTTGTG | 1140 |
| TGCCTGCTGA | ATAACTTCTA | TCCCAGAGAG | GCCAAAGTAC | AGTGGAAGGT | GGATAACGCC | 1200 |
| CTCCAATCGG | GTAACTCCCA | GGAGAGTGTC | ACAGAGCAGG | ACAGCAAGGA | CAGCACCTAC | 1260 |

```
AGCCTCAGCA  GCACCCTGAC  GCTGAGCAAA  GCAGACTACG  AGAAACACAA  AGTCTACGCC    1320
TGCGAAGTCA  CCCATCAGGG  CCTGAGCTCG  CCCGTCACAA  AGAGCTTCAA  CAGGGGAGAG    1380
TGTTGAATTC  AGATCCGTTA  ACGGTTACCA  ACTACCTAGA  CTGGATTCGT  GACAACATGC    1440
GGCCGTGATA  TCTACGTATG  ATCAGCCTCG  ACTGTGCCTT  CTAGTTGCCA  GCCATCTGTT    1500
GTTTGCCCCT  CCCCCGTGCC  TTCCTTGACC  CTGGAAGGTG  CCACTCCCAC  TGTCCTTTCC    1560
TAATAAAATG  AGGAAATTGC  ATCGCATTGT  CTGAGTAGGT  GTCATTCTAT  TCTGGGGGGT    1620
GGGGTGGGGC  AGGACAGCAA  GGGGGAGGAT  TGGGAAGACA  ATAGCAGGCA  TGCTGGGGAT    1680
GCGGTGGGCT  CTATGGAACC  AGCTGGGGCT  CGACAGCTAT  GCCAAGTACG  CCCCCTATTG    1740
ACGTCAATGA  CGGTAAATGG  CCCGCCTGGC  ATTATGCCCA  GTACATGACC  TTATGGGACT    1800
TTCCTACTTG  GCAGTACATC  TACGTATTAG  TCATCGCTAT  TACCATGGTG  ATGCGGTTTT    1860
GGCAGTACAT  CAATGGGCGT  GGATAGCGGT  TTGACTCACG  GGGATTTCCA  AGTCTCCACC    1920
CCATTGACGT  CAATGGGAGT  TTGTTTTGGC  ACCAAAATCA  ACGGGACTTT  CCAAAATGTC    1980
GTAACAACTC  CGCCCCATTG  ACGCAAATGG  GCGGTAGGCG  TGTACGGTGG  GAGGTCTATA    2040
TAAGCAGAGC  TGGGTACGTC  CTCACATTCA  GTGATCAGCA  CTGAACACAG  ACCCGTCGAC    2100
ATGGGTTGGA  GCCTCATCTT  GCTCTTCCTT  GTCGCTGTTG  CTACGCGTGT  CGCTAGCACC    2160
AAGGGCCCAT  CGGTCTTCCC  CCTGGCACCC  TCCTCCAAGA  GCACCTCTGG  GGGCACAGCG    2220
GCCCTGGGCT  GCCTGGTCAA  GGACTACTTC  CCCGAACCGG  TGACGGTGTC  GTGGAACTCA    2280
GGCGCCCTGA  CCAGCGGCGT  GCACACCTTC  CCGGCTGTCC  TACAGTCCTC  AGGACTCTAC    2340
TCCCTCAGCA  GCGTGGTGAC  CGTGCCCTCC  AGCAGCTTGG  GCACCCAGAC  CTACATCTGC    2400
AACGTGAATC  ACAAGCCCAG  CAACACCAAG  GTGGACAAGA  AAGCAGAGCC  CAAATCTTGT    2460
GACAAAACTC  ACACATGCCC  ACCGTGCCCA  GCACCTGAAC  TCCTGGGGGG  ACCGTCAGTC    2520
TTCCTCTTCC  CCCCAAAACC  CAAGGACACC  CTCATGATCT  CCCGGACCCC  TGAGGTCACA    2580
TGCGTGGTGG  TGGACGTGAG  CCACGAAGAC  CCTGAGGTCA  AGTTCAACTG  GTACGTGGAC    2640
GGCGTGGAGG  TGCATAATGC  CAAGACAAAG  CCGCGGGAGG  AGCAGTACAA  CAGCACGTAC    2700
CGTGTGGTCA  GCGTCCTCAC  CGTCCTGCAC  CAGGACTGGC  TGAATGGCAA  GGACTACAAG    2760
TGCAAGGTCT  CCAACAAAGC  CCTCCCAGCC  CCCATCGAGA  AAACCATCTC  CAAAGCCAAA    2820
GGGCAGCCCC  GAGAACCACA  GGTGTACACC  CTGCCCCCAT  CCCGGGATGA  GCTGACCAGG    2880
AACCAGGTCA  GCCTGACCTG  CCTGGTCAAA  GGCTTCTATC  CAGCGACAT   CGCCGTGGAG    2940
TGGGAGAGCA  ATGGGCAGCC  GGAGAACAAC  TACAAGACCA  CGCCTCCCGT  GCTGGACTCC    3000
GACGGCTCCT  TCTTCCTCTA  CAGCAAGCTC  ACCGTGGACA  AGAGCAGGTG  GCAGCAGGGG    3060
AACGTCTTCT  CATGCTCCGT  GATGCATGAG  GCTCTGCACA  ACCACTACAC  GCAGAAGAGC    3120
CTCTCCCTGT  CTCCGGGTAA  ATGAGGATCC  GTTAACGGTT  ACCAACTACC  TAGACTGGAT    3180
TCGTGACAAC  ATGCGGCCGT  GATATCTACG  TATGATCAGC  CTCGACTGTG  CCTTCTAGTT    3240
GCCAGCCATC  TGTTGTTTGC  CCCTCCCCCG  TGCCTTCCTT  GACCCTGGAA  GGTGCCACTC    3300
CCACTGTCCT  TTCCTAATAA  AATGAGGAAA  TTGCATCGCA  TTGTCTGAGT  AGGTGTCATT    3360
CTATTCTGGG  GGGTGGGGTG  GGCAGGACA   GCAAGGGGGA  GGATTGGGAA  GACAATAGCA    3420
GGCATGCTGG  GGATGCGGTG  GGCTCTATGG  AACCAGCTGG  GGCTCGACAG  CGCTGGATCT    3480
CCCGATCCCC  AGCTTTGCTT  CTCAATTTCT  TATTTGCATA  ATGAGAAAAA  AGGAAAATT     3540
AATTTTAACA  CCAATTCAGT  AGTTGATTGA  GCAAATGCGT  TGCCAAAAAG  GATGCTTTAG    3600
AGACAGTGTT  CTCTGCACAG  ATAAGGACAA  ACATTATTCA  GAGGGAGTAC  CCAGAGCTGA    3660
```

```
GACTCCTAAG CCAGTGAGTG GCACAGCATT CTAGGGAGAA ATATGCTTGT CATCACCGAA     3720
GCCTGATTCC GTAGAGCCAC ACCTTGGTAA GGGCCAATCT GCTCACACAG GATAGAGAGG     3780
GCAGGAGCCA GGGCAGAGCA TATAAGGTGA GGTAGGATCA GTTGCTCCTC ACATTTGCTT     3840
CTGACATAGT TGTGTTGGGA GCTTGGATAG CTTGGACAGC TCAGGGCTGC GATTTCGCGC     3900
CAAACTTGAC GGCAATCCTA GCGTGAAGGC TGGTAGGATT TTATCCCCGC TGCCATCATG     3960
GTTCGACCAT TGAACTGCAT CGTCGCCGTG TCCCAAAATA TGGGGATTGG CAAGAACGGA     4020
GACCTACCCT GGCCTCCGCT CAGGAACGAG TTCAAGTACT TCCAAAGAAT GACCACAACC     4080
TCTTCAGTGG AAGGTAAACA GAATCTGGTG ATTATGGGTA GGAAAACCTG GTTCTCCATT     4140
CCTGAGAACA ATCGACCTTT AAAGGACAGA ATTAATATAG TTCTCAGTAG AGAACTCAAA     4200
GAACCACCAC GAGGAGCTCA TTTTCTTGCC AAAAGTTTGG ATGATGCCTT AAGACTTATT     4260
GAACAACCGG AATTGGCAAG TAAAGTAGAC ATGGTTTGGA TAGTCGGAGG CAGTTCTGTT     4320
TACCAGGAAG CCATGAATCA ACCAGGCCAC CTTAGACTCT TTGTGACAAG GATCATGCAG     4380
GAATTTGAAA GTGACACGTT TTTCCCAGAA ATTGATTTGG GGAAATATAA ACTTCTCCCA     4440
GAATACCCAG GCGTCCTCTC TGAGGTCCAG GAGGAAAAAG GCATCAAGTA TAAGTTTGAA     4500
GTCTACGAGA AGAAAGACTA ACAGGAAGAT GCTTTCAAGT TCTCTGCTCC CCTCCTAAAG     4560
TCATGCATTT TTATAAGACC ATGGGACTTT TGCTGGCTTT AGATCAGCCT CGACTGTGCC     4620
TTCTAGTTGC CAGCCATCTG TTGTTTGCCC CTCCCCCGTG CCTTCCTTGA CCCTGGAAGG     4680
TGCCACTCCC ACTGTCCTTT CCTAATAAAA TGAGGAAATT GCATCGCATT GTCTGAGTAG     4740
GTGTCATTCT ATTCTGGGGG GTGGGGTGGG GCAGGACAGC AAGGGGGAGG ATTGGGAAGA     4800
CAATAGCAGG CATGCTGGGG ATGCGGTGGG CTCTATGGAA CCAGCTGGGG CTCGAGCTAC     4860
TAGCTTTGCT TCTCAATTTC TTATTTGCAT AATGAGAAAA AAGGAAAAT TAATTTTAAC      4920
ACCAATTCAG TAGTTGATTG AGCAAATGCG TTGCCAAAAA GGATGCTTTA GAGACAGTGT     4980
TCTCTGCACA GATAAGGACA AACATTATTC AGAGGGAGTA CCCAGAGCTG AGACTCCTAA     5040
GCCAGTGAGT GGCACAGCAT TCTAGGGAGA AATATGCTTG TCATCACCGA AGCCTGATTC     5100
CGTAGAGCCA CACCTTGGTA AGGGCCAATC TGCTCACACA GGATAGAGAG GCAGGAGCC      5160
AGGGCAGAGC ATATAAGGTG AGGTAGGATC AGTTGCTCCT CACATTTGCT TCTGACATAG     5220
TTGTGTTGGG AGCTTGGATC GATCCTCTAT GGTTGAACAA GATGGATTGC ACGCAGGTTC     5280
TCCGGCCGCT TGGGTGGAGA GGCTATTCGG CTATGACTGG GCACAACAGA CAATCGGCTG     5340
CTCTGATGCC GCCGTGTTCC GGCTGTCAGC GCAGGGGCGC CCGGTTCTTT TTGTCAAGAC     5400
CGACCTGTCC GGTGCCCTGA ATGAACTGCA GGACGAGGCA GCGCGGCTAT CGTGGCTGGC     5460
CACGACGGGC GTTCCTTGCG CAGCTGTGCT CGACGTTGTC ACTGAAGCGG GAAGGGACTG     5520
GCTGCTATTG GGCGAAGTGC CGGGGCAGGA TCTCCTGTCA TCTCACCTTG CTCCTGCCGA     5580
GAAAGTATCC ATCATGGCTG ATGCAATGCG GCGGCTGCAT ACGCTTGATC CGGCTACCTG     5640
CCCATTCGAC CACCAAGCGA AACATCGCAT CGAGCGAGCA CGTACTCGGA TGGAAGCCGG     5700
TCTTGTCGAT CAGGATGATC TGGACGAAGA GCATCAGGGG CTCGCGCCAG CCGAACTGTT     5760
CGCCAGGCTC AAGGCGCGCA TGCCCGACGG CGAGGATCTC GTCGTGACCC ATGGCGATGC     5820
CTGCTTGCCG AATATCATGG TGGAAAATGG CCGCTTTTCT GGATTCATCG ACTGTGGCCG     5880
GCTGGGTGTG GCGGACCGCT ATCAGGACAT AGCGTTGGCT ACCCGTGATA TTGCTGAAGA     5940
GCTTGGCGGC GAATGGGCTG ACCGCTTCCT CGTGCTTTAC GGTATCGCCG CTTCCCGATT     6000
CGCAGCGCAT CGCCTTCTAT CGCCTTCTTG ACGAGTTCTT CTGAGCGGGA CTCTGGGGTT     6060
```

```
CGAAATGACC GACCAAGCGA CGCCCAACCT GCCATCACGA GATTTCGATT CCACCGCCGC    6120
CTTCTATGAA AGGTTGGGCT TCGGAATCGT TTTCCGGGAC GCCGGCTGGA TGATCCTCCA    6180
GCGCGGGGAT CTCATGCTGG AGTTCTTCGC CCACCCCAAC TTGTTTATTG CAGCTTATAA    6240
TGGTTACAAA TAAAGCAATA GCATCACAAA TTTCACAAAT AAAGCATTTT TTTCACTGCA    6300
TTCTAGTTGT GGTTTGTCCA AACTCATCAA TCTATCTTAT CATGTCTGGA TCGCGGCCGC    6360
GATCCCGTCG AGAGCTTGGC GTAATCATGG TCATAGCTGT TTCCTGTGTG AAATTGTTAT    6420
CCGCTCACAA TTCCACACAA CATACGAGCC GGAGCATAAA GTGTAAAGCC TGGGGTGCCT    6480
AATGAGTGAG CTAACTCACA TTAATTGCGT TGCGCTCACT GCCCGCTTTC CAGTCGGGAA    6540
ACCTGTCGTG CCAGCTGCAT TAATGAATCG GCCAACGCGC GGGGAGAGGC GGTTTGCGTA    6600
TTGGGCGCTC TTCCGCTTCC TCGCTCACTG ACTCGCTGCG CTCGGTCGTT CGGCTGCGGC    6660
GAGCGGTATC AGCTCACTCA AAGGCGGTAA TACGGTTATC CACAGAATCA GGGGATAACG    6720
CAGGAAAGAA CATGTGAGCA AAAGGCCAGC AAAAGGCCAG GAACCGTAAA AAGGCCGCGT    6780
TGCTGGCGTT TTTCCATAGG CTCCGCCCCC CTGACGAGCA TCACAAAAAT CGACGCTCAA    6840
GTCAGAGGTG GCGAAACCCG ACAGGACTAT AAAGATACCA GGCGTTTCCC CCTGGAAGCT    6900
CCCTCGTGCG CTCTCCTGTT CCGACCCTGC CGCTTACCGG ATACCTGTCC GCCTTTCTCC    6960
CTTCGGGAAG CGTGGCGCTT TCTCAATGCT CACGCTGTAG GTATCTCAGT TCGGTGTAGG    7020
TCGTTCGCTC CAAGCTGGGC TGTGTGCACG AACCCCCCGT TCAGCCCGAC CGCTGCGCCT    7080
TATCCGGTAA CTATCGTCTT GAGTCCAACC CGGTAAGACA CGACTTATCG CCACTGGCAG    7140
CAGCCACTGG TAACAGGATT AGCAGAGCGA GGTATGTAGG CGGTGCTACA GAGTTCTTGA    7200
AGTGGTGGCC TAACTACGGC TACACTAGAA GGACAGTATT TGGTATCTGC GCTCTGCTGA    7260
AGCCAGTTAC CTTCGGAAAA AGAGTTGGTA GCTCTTGATC CGGCAAACAA ACCACCGCTG    7320
GTAGCGGTGG TTTTTTTGTT TGCAAGCAGC AGATTACGCG CAGAAAAAAA GGATCTCAAG    7380
AAGATCCTTT GATCTTTTCT ACGGGGTCTG ACGCTCAGTG GAACGAAAAC TCACGTTAAG    7440
GGATTTTGGT CATGAGATTA TCAAAAGGA TCTTCACCTA GATCCTTTTA AATTAAAAAT    7500
GAAGTTTTAA ATCAATCTAA AGTATATATG AGTAAACTTG GTCTGACAGT TACCAATGCT    7560
TAATCAGTGA GGCACCTATC TCAGCGATCT GTCTATTTCG TTCATCCATA GTTGCCTGAC    7620
TCCCCGTCGT GTAGATAACT ACGATACGGG AGGGCTTACC ATCTGGCCCC AGTGCTGCAA    7680
TGATACCGCG AGACCCACGC TCACCGGCTC CAGATTTATC AGCAATAAAC CAGCCAGCCG    7740
GAAGGGCCGA GCGCAGAAGT GGTCCTGCAA CTTTATCCGC CTCCATCCAG TCTATTAATT    7800
GTTGCCGGGA AGCTAGAGTA AGTAGTTCGC CAGTTAATAG TTTGCGCAAC GTTGTTGCCA    7860
TTGCTACAGG CATCGTGGTG TCACGCTCGT CGTTTGGTAT GGCTTCATTC AGCTCCGGTT    7920
CCCAACGATC AAGGCGAGTT ACATGATCCC CCATGTTGTG CAAAAAAGCG GTTAGCTCCT    7980
TCGGTCCTCC GATCGTTGTC AGAAGTAAGT TGGCCGCAGT GTTATCACTC ATGGTTATGG    8040
CAGCACTGCA TAATTCTCTT ACTGTCATGC CATCCGTAAG ATGCTTTTCT GTGACTGGTG    8100
AGTACTCAAC CAAGTCATTC TGAGAATAGT GTATGCGGCG ACCGAGTTGC TCTTGCCCGG    8160
CGTCAATACG GGATAATACC GCGCCACATA GCAGAACTTT AAAAGTGCTC ATCATTGGAA    8220
AACGTTCTTC GGGGCGAAAA CTCTCAAGGA TCTTACCGCT GTTGAGATCC AGTTCGATGT    8280
AACCCACTCG TGCACCCAAC TGATCTTCAG CATCTTTTAC TTTCACCAGC GTTTCTGGGT    8340
GAGCAAAAAC AGGAAGGCAA AATGCCGCAA AAAAGGGAAT AAGGGCGACA CGGAAATGTT    8400
GAATACTCAT ACTCTTCCTT TTTCAATATT ATTGAAGCAT TTATCAGGGT TATTGTCTCA    8460
```

-continued

| TGAGCGGATA | CATATTTGAA | TGTATTTAGA | AAAATAAACA | AATAGGGGTT | CCGCGCACAT | 8520 |
| TTCCCCGAAA | AGTGCCACCT | | | | | 8540 |

( 2 ) INFORMATION FOR SEQ ID NO:3:

( i ) SEQUENCE CHARACTERISTICS:
        ( A ) LENGTH: 9209 base pairs
        ( B ) TYPE: nucleic acid
        ( C ) STRANDEDNESS: single
        ( D ) TOPOLOGY: circular ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

| GACGTCGCGG | CCGCTCTAGG | CCTCCAAAAA | AGCCTCCTCA | CTACTTCTGG | AATAGCTCAG | 60 |
| AGGCCGAGGC | GGCCTCGGCC | TCTGCATAAA | TAAAAAAAAT | TAGTCAGCCA | TGCATGGGGC | 120 |
| GGAGAATGGG | CGGAACTGGG | CGGAGTTAGG | GGCGGGATGG | GCGGAGTTAG | GGGCGGGACT | 180 |
| ATGGTTGCTG | ACTAATTGAG | ATGCATGCTT | TGCATACTTC | TGCCTGCTGG | GGAGCCTGGG | 240 |
| GACTTTCCAC | ACCTGGTTGC | TGACTAATTG | AGATGCATGC | TTTGCATACT | TCTGCCTGCT | 300 |
| GGGGAGCCTG | GGACTTTCC | ACACCCTAAC | TGACACACAT | TCCACAGAAT | TAATTCCCT | 360 |
| AGTTATTAAT | AGTAATCAAT | TACGGGGTCA | TTAGTTCATA | GCCCATATAT | GGAGTTCCGC | 420 |
| GTTACATAAC | TTACGGTAAA | TGGCCCGCCT | GGCTGACCGC | CCAACGACCC | CCGCCCATTG | 480 |
| ACGTCAATAA | TGACGTATGT | TCCCATAGTA | ACGCCAATAG | GGACTTTCCA | TTGACGTCAA | 540 |
| TGGGTGGACT | ATTTACGGTA | AACTGCCCAC | TTGGCAGTAC | ATCAAGTGTA | TCATATGCCA | 600 |
| AGTACGCCCC | CTATTGACGT | CAATGACGGT | AAATGGCCCG | CCTGGCATTA | TGCCCAGTAC | 660 |
| ATGACCTTAT | GGGACTTTCC | TACTTGGCAG | TACATCTACG | TATTAGTCAT | CGCTATTACC | 720 |
| ATGGTGATGC | GGTTTTGGCA | GTACATCAAT | GGGCGTGGAT | ACCGGTTTGA | CTCACGCGGA | 780 |
| TTTCCAAGTC | TCCACCCCAT | TGACGTCAAT | GGGAGTTTGT | TTTGGCACCA | AAATCAACGG | 840 |
| GACTTTCCAA | AATGTCGTAA | CAACTCCGCC | CCATTGACGC | AAATGGGCGG | TAGGCGTGTA | 900 |
| CGGTGGGAGG | TCTATATAAG | CAGAGCTGGG | TACGTGAACC | GTCAGATCGC | CTGGAGACGC | 960 |
| CATCACAGAT | CTCTCACTAT | GGATTTTCAG | GTGCAGATTA | TCAGCTTCCT | GCTAATCAGT | 1020 |
| GCTTCAGTCA | TAATGTCCAG | AGGACAAATT | GTTCTCTCCC | AGTCTCCAGC | AATCCTGTCT | 1080 |
| GCATCTCCAG | GGGAGAAGGT | CACAATGACT | TGCAGGGCCA | GCTCAAGTGT | AAGTTACATC | 1140 |
| CACTGGTTCC | AGCAGAAGCC | AGGATCCTCC | CCCAAACCCT | GGATTTATGC | CACATCCAAC | 1200 |
| CTGGCTTCTG | GAGTCCCTGT | TCGCTTCAGT | GGCAGTGGGT | CTGGGACTTC | TTACTCTCTC | 1260 |
| ACAATCAGCA | GAGTGGAGGC | TGAAGATGCT | GCCACTTATT | ACTGCCAGCA | GTGGACTAGT | 1320 |
| AACCCACCCA | CGTTCGGAGG | GGGGACCAAG | CTGGAAATCA | AACGTACGGT | GGCTGCACCA | 1380 |
| TCTGTCTTCA | TCTTCCCGCC | ATCTGATGAG | CAGTTGAAAT | CTGGAACTGC | CTCTGTTGTG | 1440 |
| TGCCTGCTGA | ATAACTTCTA | TCCCAGAGAG | GCCAAAGTAC | AGTGGAAGGT | GGATAACGCC | 1500 |
| CTCCAATCGG | GTAACTCCCA | GGAGAGTGTC | ACAGAGCAGG | ACAGCAAGGA | CAGCACCTAC | 1560 |
| AGCCTCAGCA | GCACCCTGAC | GCTGAGCAAA | GCAGACTACG | AGAAACACAA | AGTCTACGCC | 1620 |
| TGCGAAGTCA | CCCATCAGGG | CCTGAGCTCG | CCCGTCACAA | AGAGCTTCAA | CAGGGGAGAG | 1680 |
| TGTTGAATTC | AGATCCGTTA | ACGGTTACCA | ACTACCTAGA | CTGGATTCGT | GACAACATGC | 1740 |

| | | | | | | |
|---|---|---|---|---|---|---|
| GGCCGTGATA | TCTACGTATG | ATCAGCCTCG | ACTGTGCCTT | CTAGTTGCCA | GCCATCTGTT | 1800 |
| GTTTGCCCCT | CCCCCGTGCC | TTCCTTGACC | CTGGAAGGTG | CCACTCCCAC | TGTCCTTTCC | 1860 |
| TAATAAAATG | AGGAAATTGC | ATCGCATTGT | CTGAGTAGGT | GTCATTCTAT | TCTGGGGGT | 1920 |
| GGGGTGGGGC | AGGACAGCAA | GGGGGAGGAT | TGGAAGACA | ATAGCAGGCA | TGCTGGGGAT | 1980 |
| GCGGTGGGCT | CTATGGAACC | AGCTGGGGCT | CGACAGCTAT | GCCAAGTACG | CCCCTATTG | 2040 |
| ACGTCAATGA | CGGTAAATGG | CCCGCCTGGC | ATTATGCCCA | GTACATGACC | TTATGGGACT | 2100 |
| TTCCTACTTG | GCAGTACATC | TACGTATTAG | TCATCGCTAT | TACCATGGTG | ATGCGGTTTT | 2160 |
| GGCAGTACAT | CAATGGGCGT | GGATAGCGGT | TTGACTCACG | GGGATTTCCA | AGTCTCCACC | 2220 |
| CCATTGACGT | CAATGGGAGT | TTGTTTTGGC | ACCAAAATCA | ACGGGACTTT | CCAAAATGTC | 2280 |
| GTAACAACTC | CGCCCCATTG | ACGCAAATGG | GCGGTAGGCG | TGTACGGTGG | GAGGTCTATA | 2340 |
| TAAGCAGAGC | TGGGTACGTC | CTCACATTCA | GTGATCAGCA | CTGAACACAG | ACCCGTCGAC | 2400 |
| ATGGGTTGGA | GCCTCATCTT | GCTCTTCCTT | GTCGCTGTTG | CTACGCGTGT | CCTGTCCCAG | 2460 |
| GTACAACTGC | AGCAGCCTGG | GGCTGAGCTG | GTGAAGCCTG | GGGCCTCAGT | GAAGATGTCC | 2520 |
| TGCAAGGCTT | CTGGCTACAC | ATTACCAGT | TACAATATGC | ACTGGGTAAA | ACAGACACCT | 2580 |
| GGTCGGGGCC | TGGAATGGAT | TGGAGCTATT | TATCCCGGAA | ATGGTGATAC | TTCCTACAAT | 2640 |
| CAGAAGTTCA | AAGGCAAGGC | CACATTGACT | GCAGACAAAT | CCTCCAGCAC | AGCCTACATG | 2700 |
| CAGCTCAGCA | GCCTGACATC | TGAGGACTCT | GCGGTCTATT | ACTGTGCAAG | ATCGACTTAC | 2760 |
| TACGGCGGTG | ACTGGTACTT | CAATGTCTGG | GGCGCAGGGA | CCACGGTCAC | CGTCTCTGCA | 2820 |
| GCTAGCACCA | AGGGCCCATC | GGTCTTCCCC | CTGGCACCCT | CCTCCAAGAG | CACCTCTGGG | 2880 |
| GGCACAGCGG | CCCTGGGCTG | CCTGGTCAAG | GACTACTTCC | CCGAACCGGT | GACGGTGTCG | 2940 |
| TGGAACTCAG | GCGCCCTGAC | CAGCGGCGTG | CACACCTTCC | CGGCTGTCCT | ACAGTCCTCA | 3000 |
| GGACTCTACT | CCCTCAGCAG | CGTGGTGACC | GTGCCCTCCA | GCAGCTTGGG | CACCCAGACC | 3060 |
| TACATCTGCA | ACGTGAATCA | CAAGCCCAGC | AACACCAAGG | TGGACAAGAA | AGCAGAGCCC | 3120 |
| AAATCTTGTG | ACAAAACTCA | CACATGCCCA | CCGTGCCCAG | CACCTGAACT | CCTGGGGGGA | 3180 |
| CCGTCAGTCT | TCCTCTTCCC | CCCAAAACCC | AAGGACACCC | TCATGATCTC | CCGGACCCCT | 3240 |
| GAGGTCACAT | GCGTGGTGGT | GGACGTGAGC | CACGAAGACC | CTGAGGTCAA | GTTCAACTGG | 3300 |
| TACGTGGACG | GCGTGGAGGT | GCATAATGCC | AAGACAAAGC | CGCGGGAGGA | GCAGTACAAC | 3360 |
| AGCACGTACC | GTGTGGTCAG | CGTCCTCACC | GTCCTGCACC | AGGACTGGCT | GAATGGCAAG | 3420 |
| GAGTACAAGT | GCAAGGTCTC | CAACAAAGCC | CTCCCAGCCC | CCATCGAGAA | AACCATCTCC | 3480 |
| AAAGCCAAAG | GGCAGCCCCG | AGAACCACAG | GTGTACACCC | TGCCCCCATC | CCGGGATGAG | 3540 |
| CTGACCAAGA | ACCAGGTCAG | CCTGACCTGC | CTGGTCAAAG | GCTTCTATCC | CAGCGACATC | 3600 |
| GCCGTGGAGT | GGGAGAGCAA | TGGGCAGCCG | GAGAACAACT | ACAAGACCAC | GCCTCCCGTG | 3660 |
| CTGGACTCCG | ACGGCTCCTT | CTTCCTCTAC | AGCAAGCTCA | CCGTGGACAA | GAGCAGGTGG | 3720 |
| CAGCAGGGGA | ACGTCTTCTC | ATGCTCCGTG | ATGCATGAGG | CTCTGCACAA | CCACTACACG | 3780 |
| CAGAAGAGCC | TCTCCCTGTC | TCCGGGTAAA | TGAGGATCCG | TTAACGGTTA | CCAACTACCT | 3840 |
| AGACTGGATT | CGTGACAACA | TGCGGCCGTG | ATATCTACGT | ATGATCAGCC | TCGACTGTGC | 3900 |
| CTTCTAGTTG | CCAGCCATCT | GTTGTTTGCC | CCTCCCCCGT | GCCTTCCTTG | ACCCTGGAAG | 3960 |
| GTGCCACTCC | CACTGTCCTT | TCCTAATAAA | ATGAGGAAAT | TGCATCGCAT | TGTCTGAGTA | 4020 |
| GGTGTCATTC | TATTCTGGGG | GGTGGGGTGG | GCAGGACAG | CAAGGGGGAG | GATTGGGAAG | 4080 |
| ACAATAGCAG | GCATGCTGGG | GATGCGGTGG | GCTCTATGGA | ACCAGCTGGG | GCTCGACAGC | 4140 |

```
GCTGGATCTC CCGATCCCCA GCTTTGCTTC TCAATTTCTT ATTTGCATAA TGAGAAAAAA   4200
AGGAAAATTA ATTTTAACAC CAATTCAGTA GTTGATTGAG CAAATGCGTT GCCAAAAAGG   4260
ATGCTTTAGA GACAGTGTTC TCTGCACAGA TAAGGACAAA CATTATTCAG AGGGAGTACC   4320
CAGAGCTGAG ACTCCTAAGC CAGTGAGTGG CACAGCATTC TAGGGAGAAA TATGCTTGTC   4380
ATCACCGAAG CCTGATTCCG TAGAGCCACA CCTTGGTAAG GGCCAATCTG CTCACACAGG   4440
ATAGAGAGGG CAGGAGCCAG GGCAGAGCAT ATAAGGTGAG GTAGGATCAG TTGCTCCTCA   4500
CATTTGCTTC TGACATAGTT GTGTTGGAG CTTGGATAGC TTGGACAGCT CAGGGCTGCG    4560
ATTTCGCGCC AAACTTGACG GCAATCCTAG CGTGAAGGCT GGTAGGATTT TATCCCCGCT   4620
GCCATCATGG TTCGACCATT GAACTGCATC GTCGCCGTGT CCCAAAATAT GGGGATTGGC   4680
AAGAACGGAG ACCTACCCTG GCCTCCGCTC AGGAACGAGT TCAAGTACTT CCAAAGAATG   4740
ACCACAACCT CTTCAGTGGA AGGTAAACAG AATCTGGTGA TATGGGTAG GAAAACCTGG    4800
TTCTCCATTC CTGAGAAGAA TCGACCTTTA AAGGACAGAA TTAATATAGT TCTCAGTAGA   4860
GAACTCAAAG AACCACCACG AGGAGCTCAT TTTCTTGCCA AAAGTTTGGA TGATGCCTTA   4920
AGACTTATTG AACAACCGGA ATTGGCAAGT AAAGTAGACA TGGTTTGGAT AGTCGGAGGC   4980
AGTTCTGTTT ACCAGGAAGC CATGAATCAA CCAGGCCACC TTAGACTCTT TGTGACAAGG   5040
ATCATGCAGG AATTTGAAAG TGACACGTTT TTCCCAGAAA TTGATTGGG GAAATATAAA    5100
CTTCTCCCAG AATACCCAGG CGTCCTCTCT GAGGTCCAGG AGGAAAAAGG CATCAAGTAT   5160
AAGTTTGAAG TCTACGAGAA GAAAGACTAA CAGGAAGATG CTTTCAAGTT CTCTGCTCCC   5220
CTCCTAAAGC TATGCATTTT TATAAGACCA TGGGACTTTT GCTGGCTTTA GATCAGCCTC   5280
GACTGTGCCT TCTAGTTGCC AGCCATCGT TGTTTGCCCC TCCCCCGTGC CTTCCTTGAC    5340
CCTGGAAGGT GCCACTCCCA CTGTCCTTTC CTAATAAAAT GAGGAAATTG CATCGCATTG   5400
TCTGAGTAGG TGTCATTCTA TTCTGGGGGG TGGGGTGGGG CAGGACAGCA AGGGGGAGGA   5460
TTGGGAAGAC AATAGCAGGC ATGCTGGGGA TGCGGTGGGC TCTATGGAAC CAGCTGGGGC   5520
TCGAGCTACT AGCTTTGCTT CTCAATTTCT TATTTGCATA ATGAGAAAAA AAGGAAAATT   5580
AATTTTAACA CCAATTCAGT AGTTGATTGA GCAAATGCGT TGCCAAAAAG GATGCTTTAG   5640
AGACAGTGTT CTCTGCACAG ATAAGGACAA ACATTATTCA GAGGGAGTAC CCAGAGCTGA   5700
GACTCCTAAG CCAGTGAGTG GCACAGCATT CTAGGGAGAA ATATGCTTGT CATCACCGAA   5760
GCCTGATTCC GTAGAGCCAC ACCTTGGTAA GGGCCAATCT GCTCACACAG GATAGAGAGG   5820
GCAGGAGCCA GGGCAGAGCA TATAAGGTGA GGTAGGATCA GTTGCTCCTC ACATTTGCTT   5880
CTGACATAGT TGTGTTGGGA GCTTGGATCG ATCCTCTATG GTTGAACAAG ATGGATTGCA   5940
CGCAGGTTCT CCGGCCGCTT GGGTGGAGAG GCTATTCGGC TATGACTGGG CACAACAGAC   6000
AATCGGCTGC TCTGATGCCG CCGTGTTCCG GCTGTCAGCG CAGGGGCGCC CGGTTCTTTT   6060
TGTCAAGACC GACCTGTCCG GTGCCCTGAA TGAACTGCAG GACGAGGCAG CGCGGCTATC   6120
GTGGCTGGCC ACGACGGGCG TTCCTTGCGC AGCTGTGCTC GACGTTGTCA CTGAAGCGGG   6180
AAGGGACTGG CTGCTATTGG GCGAAGTGCC GGGGCAGGAT CTCCTGTCAT CTCACCTTGC   6240
TCCTGCCGAG AAAGTATCCA TCATGGCTGA TGCAATGCGG CGGCTGCATA CGCTTGATCC   6300
GGCTACCTGC CCATTCGACC ACCAAGCGAA ACATCGCATC GAGCGAGCAC GTACTCGGAT   6360
GGAAGCCGGT CTTGTCGATC AGGATGATCT GGACGAAGAG CATCAGGGGC TCGCGCCAGC   6420
CGAACTGTTC GCCAGGCTCA AGGCGCGCAT GCCCGACGGC GAGGATCTCG TCGTGACCCA   6480
TGGCGATGCC TGCTTGCCGA ATATCATGGT GGAAAATGGC CGCTTTTCTG GATTCATCGA   6540
```

| | | | | | | |
|---|---|---|---|---|---|---|
| CTGTGGCCGG | CTGGGTGTGG | CGGACCGCTA | TCAGGACATA | GCGTTGGCTA | CCCGTGATAT | 6600 |
| TGCTGAAGAG | CTTGGCGGCG | AATGGGCTGA | CCGCTTCCTC | GTGCTTTACG | GTATCGCCGC | 6660 |
| TCCCGATTCG | CAGCGCATCG | CCTTCTATCG | CCTTCTTGAC | GAGTTCTTCT | GAGCGGGACT | 6720 |
| CTGGGGTTCG | AAATGACCGA | CCAAGCGACG | CCCAACCTGC | CATCACGAGA | TTTCGATTCC | 6780 |
| ACCGCCGCCT | TCTATGAAAG | GTTGGGCTTC | GGAATCGTTT | TCCGGGACGC | CGGCTGGATG | 6840 |
| ATCCTCCAGC | GCGGGGATCT | CATGCTGGAG | TTCTTCGCCC | ACCCCAACTT | GTTTATTGCA | 6900 |
| GCTTATAATG | GTTACAAATA | AAGCAATAGC | ATCACAAATT | TCACAAATAA | AGCATTTTTT | 6960 |
| TCACTGCATT | CTAGTTGTGG | TTTGTCCAAA | CTCATCAATC | TATCTTATCA | TGTCTGGATC | 7020 |
| GCGGCCGCGA | TCCCGTCGAG | AGCTTGGCGT | AATCATGGTC | ATAGCTGTTT | CCTGTGTGAA | 7080 |
| ATTGTTATCC | GCTCACAATT | CCACACAACA | TACGAGCCGG | AAGCATAAAG | TGTAAAGCCT | 7140 |
| GGGGTGCCTA | ATGAGTGAGC | TAACTCACAT | TAATTGCGTT | GCGCTCACTG | CCCGCTTTCC | 7200 |
| AGTCGGGAAA | CCTGTCGTGC | CAGCTGCATT | AATGAATCGG | CCAACGCGCG | GGGAGAGGCG | 7260 |
| GTTTGCGTAT | TGGGCGCTCT | TCCGCTTCCT | CGCTCACTGA | CTCGCTGCGC | TCGGTCGTTC | 7320 |
| GGCTGCGGCG | AGCGGTATCA | GCTCACTCAA | AGGCGGTAAT | ACGGTTATCC | ACAGAATCAG | 7380 |
| GGGATAACGC | AGGAAAGAAC | ATGTGAGCAA | AAGGCCAGCA | AAAGGCCAGG | AACCGTAAAA | 7440 |
| AGGCCGCGTT | GCTGGCGTTT | TTCCATAGGC | TCCGCCCCCC | TGACGAGCAT | CACAAAAATC | 7500 |
| GACGCTCAAG | TCAGAGGTGG | CGAAACCCGA | CAGGACTATA | AAGATACCAG | GCGTTTCCCC | 7560 |
| CTGGAAGCTC | CCTCGTGCGC | TCTCCTGTTC | CGACCCTGCC | GCTTACCGGA | TACCTGTCCG | 7620 |
| CCTTTCTCCC | TTCGGGAAGC | GTGGCGCTTT | CTCAATGCTC | ACGCTGTAGG | TATCTCAGTT | 7680 |
| CGGTGTAGGT | CGTTCGCTCC | AAGCTGGGCT | GTGTGCACGA | ACCCCCCGTT | CAGCCCGACC | 7740 |
| GCTGCGCCTT | ATCCGGTAAC | TATCGTCTTG | AGTCCAACCC | GGTAAGACAC | GACTTATCGC | 7800 |
| CACTGGCAGC | AGCCACTGGT | AACAGGATTA | GCAGAGCGAG | GTATGTAGGC | GGTGCTACAG | 7860 |
| AGTTCTTGAA | GTGGTGGCCT | AACTACGGCT | ACACTAGAAG | GACAGTATTT | GGTATCTGCG | 7920 |
| CTCTGCTGAA | GCCAGTTACC | TTCGGAAAAA | GAGTTGGTAG | CTCTTGATCC | GGCAAACAAA | 7980 |
| CCACCGCTGG | TAGCGGTGGT | TTTTTTGTTT | GCAAGCAGCA | GATTACGCGC | AGAAAAAAAG | 8040 |
| GATCTCAAGA | AGATCCTTTG | ATCTTTTCTA | CGGGGTCTGA | CGCTCAGTGG | AACGAAAACT | 8100 |
| CACGTTAAGG | GATTTTGGTC | ATGAGATTAT | CAAAAAGGAT | CTTCACCTAG | ATCCTTTTAA | 8160 |
| ATTAAAAATG | AAGTTTTAAA | TCAATCTAAA | GTATATATGA | GTAAACTTGG | TCTGACAGTT | 8220 |
| ACCAATGCTT | AATCAGTGAG | GCACCTATCT | CAGCGATCTG | TCTATTTCGT | TCATCCATAG | 8280 |
| TTGCCTGACT | CCCCGTCGTG | TAGATAACTA | CGATACGGGA | GGGCTTACCA | TCTGGCCCCA | 8340 |
| GTGCTGCAAT | GATACCGCGA | GACCCACGCT | CACCGGCTCC | AGATTTATCA | GCAATAAACC | 8400 |
| AGCCAGCCGG | AAGGGCCGAG | CGCAGAAGTG | GTCCTGCAAC | TTTATCCGCC | TCCATCCAGT | 8460 |
| CTATTAATTG | TTGCCGGGAA | GCTAGAGTAA | GTAGTTCGCC | AGTTAATAGT | TTGCGCAACG | 8520 |
| TTGTTGCCAT | TGCTACAGGC | ATCGTGGTGT | CACGCTCGTC | GTTTGGTATG | GCTTCATTCA | 8580 |
| GCTCCGGTTC | CCAACGATCA | AGGCGAGTTA | CATGATCCCC | CATGTTGTGC | AAAAAAGCGG | 8640 |
| TTAGCTCCTT | CGGTCCTCCG | ATCGTTGTCA | GAAGTAAGTT | GGCCGCAGTG | TTATCACTCA | 8700 |
| TGGTTATGGC | AGCACTGCAT | AATTCTCTTA | CTGTCATGCC | ATCCGTAAGA | TGCTTTTCTG | 8760 |
| TGACTGGTGA | GTACTCAACC | AAGTCATTCT | GAGAATAGTG | TATGCGGCGA | CCGAGTTGCT | 8820 |
| CTTGCCCGGC | GTCAATACGG | GATAATACCG | CGCCACATAG | CAGAACTTTA | AAAGTGCTCA | 8880 |
| TCATTGGAAA | ACGTTCTTCG | GGGCGAAAAC | TCTCAAGGAT | CTTACCGCTG | TTGAGATCCA | 8940 |

```
GTTCGATGTA  ACCCACTCGT  GCACCCAACT  GATCTTCAGC  ATCTTTTACT  TTCACCAGCG     9000

TTTCTGGGTG  AGCAAAAACA  GGAAGGCAAA  ATGCCGCAAA  AAAGGGAATA  AGGGCGACAC     9060

GGAAATGTTG  AATACTCATA  CTCTTCCTTT  TTCAATATTA  TTGAAGCATT  TATCAGGGTT     9120

ATTGTCTCAT  GAGCGGATAC  ATATTTGAAT  GTATTTAGAA  AAATAAACAA  ATAGGGGTTC     9180

CGCGCACATT  TCCCCGAAAA  GTGCCACCT                                          9209
```

( 2 ) INFORMATION FOR SEQ ID NO:4:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

```
ATCACAGATC  TCTCACCATG  GATTTTCAGG  TGCAGATTAT  CAGCTTC                    47
```

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:5:

```
TGCAGCATCC  GTACGTTTGA  TTTCCAGCTT                                         30
```

( 2 ) INFORMATION FOR SEQ ID NO:6:

( i ) SEQUENCE CHARACTERISTICS:
        ( A ) LENGTH: 384 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..384

( i x ) FEATURE:
        ( A ) NAME/KEY: mat_peptide
        ( B ) LOCATION: 67..384

( x i ) SEQUENCE DESCRIPTION: SEQ ID NO:6:

```
ATG  GAT  TTT  CAG  GTG  CAG  ATT  ATC  AGC  TTC  CTG  CTA  ATC  AGT  GCT  TCA     48
Met  Asp  Phe  Gln  Val  Gln  Ile  Ile  Ser  Phe  Leu  Leu  Ile  Ser  Ala  Ser
-22       -20                 -15                      -10

GTC  ATA  ATG  TCC  AGA  GGG  CAA  ATT  GTT  CTC  TCC  CAG  TCT  CCA  GCA  ATC     96
Val  Ile  Met  Ser  Arg  Gly  Gln  Ile  Val  Leu  Ser  Gln  Ser  Pro  Ala  Ile
      -5              -1    1                 5                            10
```

| | | | | | | | | | | | | | | | | |
|---|---|---|---|---|---|---|---|---|---|---|---|---|---|---|---|---|
| CTG | TCT | GCA | TCT | CCA | GGG | GAG | AAG | GTC | ACA | ATG | ACT | TGC | AGG | GCC | AGC | 144 |
| Leu | Ser | Ala | Ser | Pro | Gly | Glu | Lys | Val | Thr | Met | Thr | Cys | Arg | Ala | Ser | |
| | | | | 15 | | | | | 20 | | | | | 25 | | |
| TCA | AGT | GTA | AGT | TAC | ATC | CAC | TGG | TTC | CAG | CAG | AAG | CCA | GGA | TCC | TCC | 192 |
| Ser | Ser | Val | Ser | Tyr | Ile | His | Trp | Phe | Gln | Gln | Lys | Pro | Gly | Ser | Ser | |
| | | | 30 | | | | | 35 | | | | | 40 | | | |
| CCC | AAA | CCC | TGG | ATT | TAT | GCC | ACA | TCC | AAC | CTG | GCT | TCT | GGA | GTC | CCT | 240 |
| Pro | Lys | Pro | Trp | Ile | Tyr | Ala | Thr | Ser | Asn | Leu | Ala | Ser | Gly | Val | Pro | |
| | | 45 | | | | | 50 | | | | | 55 | | | | |
| GTT | CGC | TTC | AGT | GGC | AGT | GGG | TCT | GGG | ACT | TCT | TAC | TCT | CTC | ACA | ATC | 288 |
| Val | Arg | Phe | Ser | Gly | Ser | Gly | Ser | Gly | Thr | Ser | Tyr | Ser | Leu | Thr | Ile | |
| | 60 | | | | | 65 | | | | | 70 | | | | | |
| AGC | AGA | GTG | GAG | GCT | GAA | GAT | GCT | GCC | ACT | TAT | TAC | TGC | CAG | CAG | TGG | 336 |
| Ser | Arg | Val | Glu | Ala | Glu | Asp | Ala | Ala | Thr | Tyr | Tyr | Cys | Gln | Gln | Trp | |
| 75 | | | | 80 | | | | | 85 | | | | | | 90 | |
| ACT | AGT | AAC | CCA | CCC | ACG | TTC | GGA | GGG | GGG | ACC | AAG | CTG | GAA | ATC | AAA | 384 |
| Thr | Ser | Asn | Pro | Pro | Thr | Phe | Gly | Gly | Gly | Thr | Lys | Leu | Glu | Ile | Lys | |
| | | | | 95 | | | | | 100 | | | | | 105 | | |

(2) INFORMATION FOR SEQ ID NO:7:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

GCGGCTCCCA CGCGTGTCCT GTCCCAG                              27

(2) INFORMATION FOR SEQ ID NO:8:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: YES (ix) FEATURE:
      (A) NAME/KEY: misc_feature
      (B) LOCATION: 3
      (D) OTHER INFORMATION: /note= "Nucleotide 3 is N wherein N
         is G or C."

(ix) FEATURE:
      (A) NAME/KEY: misc_feature
      (B) LOCATION: 18
      (D) OTHER INFORMATION: /note= "Nucleotide 18 is N wherein
         N is A or C."

(ix) FEATURE:
      (A) NAME/KEY: misc_feature
      (B) LOCATION: 19
      (D) OTHER INFORMATION: /note= "Nucleotide 19 is N wherein
         N is A or G."

(ix) FEATURE:
      (A) NAME/KEY: misc_feature
      (B) LOCATION: 25

(D) OTHER INFORMATION: /note= "Nucleotide 25 is N wherein N is G or A."

(x i) SEQUENCE DESCRIPTION: SEQ ID NO:8:

GGNTGTTGTG CTAGCTGNNG AGACNGTGA                                                29

(2) INFORMATION FOR SEQ ID NO:9:

(i) SEQUENCE CHARACTERISTICS:
        (A) LENGTH: 420 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (i x) FEATURE:
        (A) NAME/KEY: CDS
        (B) LOCATION: 1..420

(i x) FEATURE:
        (A) NAME/KEY: mat_peptide
        (B) LOCATION: 58..420

(x i) SEQUENCE DESCRIPTION: SEQ ID NO:9:

```
ATG  GGT  TGG  AGC  CTC  ATC  TTG  CTC  TTC  CTT  GTC  GCT  GTT  GCT  ACG  CGT        48
Met  Gly  Trp  Ser  Leu  Ile  Leu  Leu  Phe  Leu  Val  Ala  Val  Ala  Thr  Arg
-19            -15                      -10                      -5

GTC  CTG  TCC  CAG  GTA  CAA  CTG  CAG  CAG  CCT  GGG  GCT  GAG  CTG  GTG  AAG        96
Val  Leu  Ser  Gln  Val  Gln  Leu  Gln  Gln  Pro  Gly  Ala  Glu  Leu  Val  Lys
          -1    1                 5                      10

CCT  GGG  GCC  TCA  GTG  AAG  ATG  TCC  TGC  AAG  GCT  TCT  GGC  TAC  ACA  TTT       144
Pro  Gly  Ala  Ser  Val  Lys  Met  Ser  Cys  Lys  Ala  Ser  Gly  Tyr  Thr  Phe
     15                      20                      25

ACC  AGT  TAC  AAT  ATG  CAC  TGG  GTA  AAA  CAG  ACA  CCT  GGT  CGG  GGC  CTG       192
Thr  Ser  Tyr  Asn  Met  His  Trp  Val  Lys  Gln  Thr  Pro  Gly  Arg  Gly  Leu
30                       35                      40                           45

GAA  TGG  ATT  GGA  GCT  ATT  TAT  CCC  GGA  AAT  GGT  GAT  ACT  TCC  TAC  AAT       240
Glu  Trp  Ile  Gly  Ala  Ile  Tyr  Pro  Gly  Asn  Gly  Asp  Thr  Ser  Tyr  Asn
               50                           55                           60

CAG  AAG  TTC  AAA  GGC  AAG  GCC  ACA  TTG  ACT  GCA  GAC  AAA  TCC  TCC  AGC       288
Gln  Lys  Phe  Lys  Gly  Lys  Ala  Thr  Leu  Thr  Ala  Asp  Lys  Ser  Ser  Ser
               65                      70                      75

ACA  GCC  TAC  ATG  CAG  CTC  AGC  AGC  CTG  ACA  TCT  GAG  GAC  TCT  GCG  GTC       336
Thr  Ala  Tyr  Met  Gln  Leu  Ser  Ser  Leu  Thr  Ser  Glu  Asp  Ser  Ala  Val
               80                      85                      90

TAT  TAC  TGT  GCA  AGA  TCG  ACT  TAC  TAC  GGC  GGT  GAC  TGG  TAC  TTC  AAT       384
Tyr  Tyr  Cys  Ala  Arg  Ser  Thr  Tyr  Tyr  Gly  Gly  Asp  Trp  Tyr  Phe  Asn
     95                      100                          105

GTC  TGG  GGC  GCA  GGG  ACC  ACG  GTC  ACC  GTC  TCT  GCA                            420
Val  Trp  Gly  Ala  Gly  Thr  Thr  Val  Thr  Val  Ser  Ala
110                      115                      120
```